United States Patent
Shipp et al.

(10) Patent No.: US 9,890,429 B2
(45) Date of Patent: Feb. 13, 2018

(54) COMPOSITIONS, KITS, AND METHODS FOR THE IDENTIFICATION, ASSESSMENT, PREVENTION, AND THERAPY OF CANCER

(71) Applicants: Dana-Farber Cancer Institute, Inc., Boston, MA (US); The Broad Institute, Inc., Cambridge, MA (US)

(72) Inventors: Margaret A. Shipp, Wellesley, MA (US); Stefano Monti, Somerville, MA (US); Bjoern Chapuy, Boston, MA (US); Scott J. Rodig, Westwood, MA (US); Todd R. Golub, Newton, MA (US)

(73) Assignees: Dana-Farber Cancer Institute, Inc., Boston, MA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 14/381,004

(22) PCT Filed: Feb. 28, 2013

(86) PCT No.: PCT/US2013/028297
§ 371 (c)(1),
(2) Date: Aug. 26, 2014

(87) PCT Pub. No.: WO2013/130791
PCT Pub. Date: Sep. 6, 2013

(65) Prior Publication Data
US 2015/0004158 A1 Jan. 1, 2015

Related U.S. Application Data

(60) Provisional application No. 61/604,709, filed on Feb. 29, 2012.

(51) Int. Cl.
| | | |
|---|---|---|
| *G01N 33/574* | (2006.01) | |
| *A61K 31/00* | (2006.01) | |
| *A61K 31/33* | (2006.01) | |
| *C12Q 1/68* | (2006.01) | |
| *G06F 19/24* | (2011.01) | |
| *G06F 19/20* | (2011.01) | |
| *G06F 19/22* | (2011.01) | |

(52) U.S. Cl.
CPC ..... *C12Q 1/6886* (2013.01); *G01N 33/57484* (2013.01); *G06F 19/24* (2013.01); *A61K 31/00* (2013.01); *A61K 31/33* (2013.01); *C12Q 2600/112* (2013.01); *C12Q 2600/136* (2013.01); *C12Q 2600/158* (2013.01); *G01N 2500/04* (2013.01); *G01N 2800/50* (2013.01); *G01N 2800/52* (2013.01); *G01N 2800/56* (2013.01); *G06F 19/20* (2013.01); *G06F 19/22* (2013.01)

(58) Field of Classification Search
None
See application file for complete search history.

(56) References Cited

U.S. PATENT DOCUMENTS

| | | | |
|---|---|---|---|
| 6,974,672 B2 * | 12/2005 | Powers | C12Q 1/6886 435/187 |
| 2007/0105133 A1 * | 5/2007 | Clarke | C12N 5/0693 435/6.12 |
| 2009/0269744 A1 | 10/2009 | Krause et al. | |

FOREIGN PATENT DOCUMENTS

| | | | | |
|---|---|---|---|---|
| WO | WO 2006112483 A1 * | 10/2006 | | C12Q 1/6886 |
| WO | WO 2012159030 A1 * | 11/2012 | | C12Q 1/6886 |

OTHER PUBLICATIONS

Saintigny et al., Cancer Prev. Res., 2011, 4(2):218-29.*
Cancer information from National Institute of Cancer, Apr. 29, 2010, pp. 1-2.*
Vogelstein et al. Nature Medicine, 2004, 10(8): 789-799.*
Malumbres et al.,Trends in Pharmacological Sciences, 2007, 29 (1): 16-21.*
Lin et al, Leukemia & Lymphoma, 2002, 43(4): 793-797.*
International Search Report dated Jul. 26, 2013, from PCT/US2013/028297.

* cited by examiner

*Primary Examiner* — Hong Sang
(74) *Attorney, Agent, or Firm* — Foley Hoag LLP

(57) ABSTRACT

The present invention relates to compositions, kits, and methods for detecting, characterizing, preventing, and treating cancer (e.g., hematological malignancies in humans). A variety of biomarker chromosomal number alterations (CNAs) and biomarkers corresponding thereto, are provided, wherein alterations in the copy number of one or more of the biomarker CNAs and/or alterations in the amount, structure, and/or activity of one or more of the biomarkers comprised within the CNAs is associated with cancer status.

20 Claims, 27 Drawing Sheets

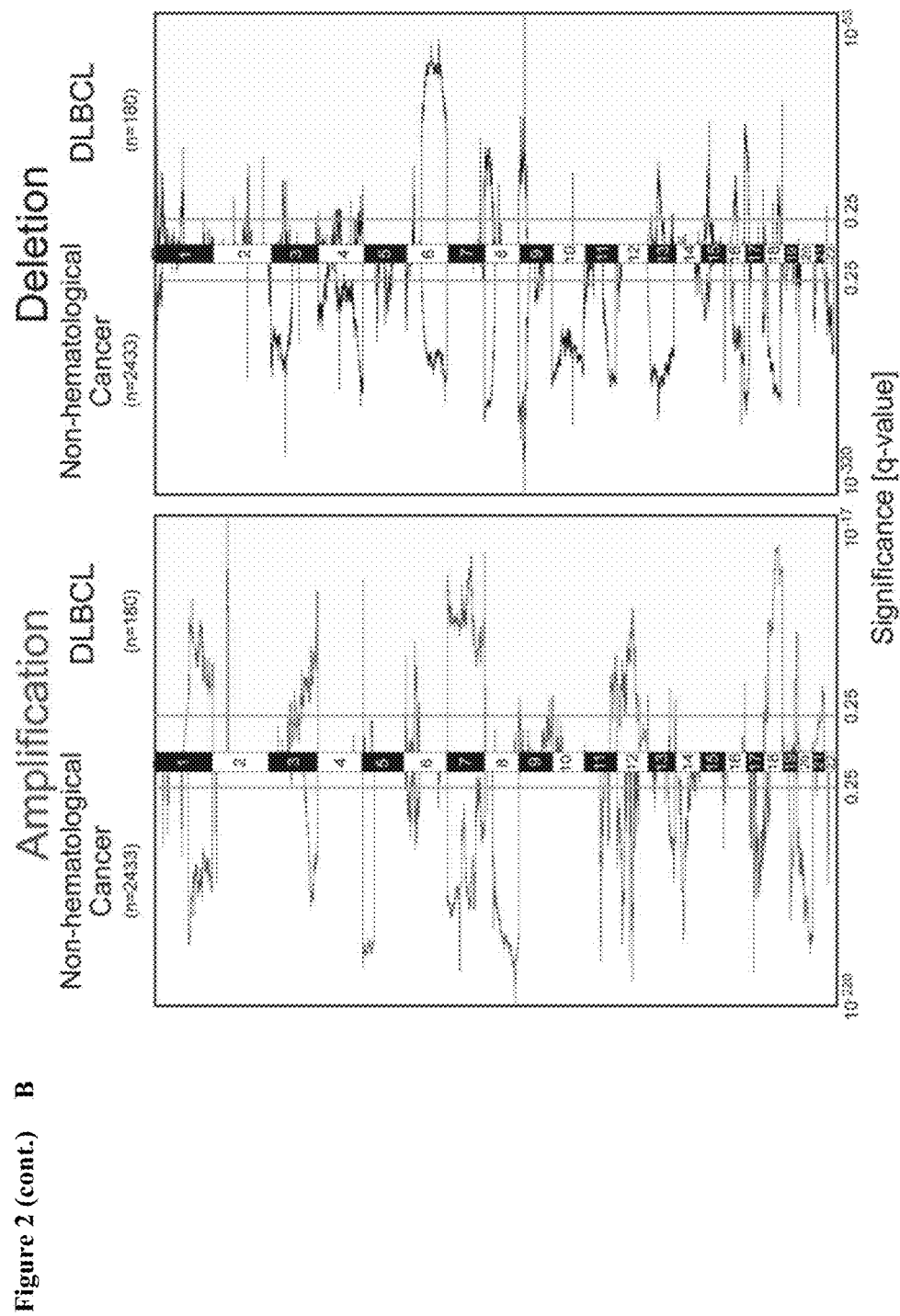
Figure 2 (cont.) B

Figure 2 (cont.)  B (cont.)

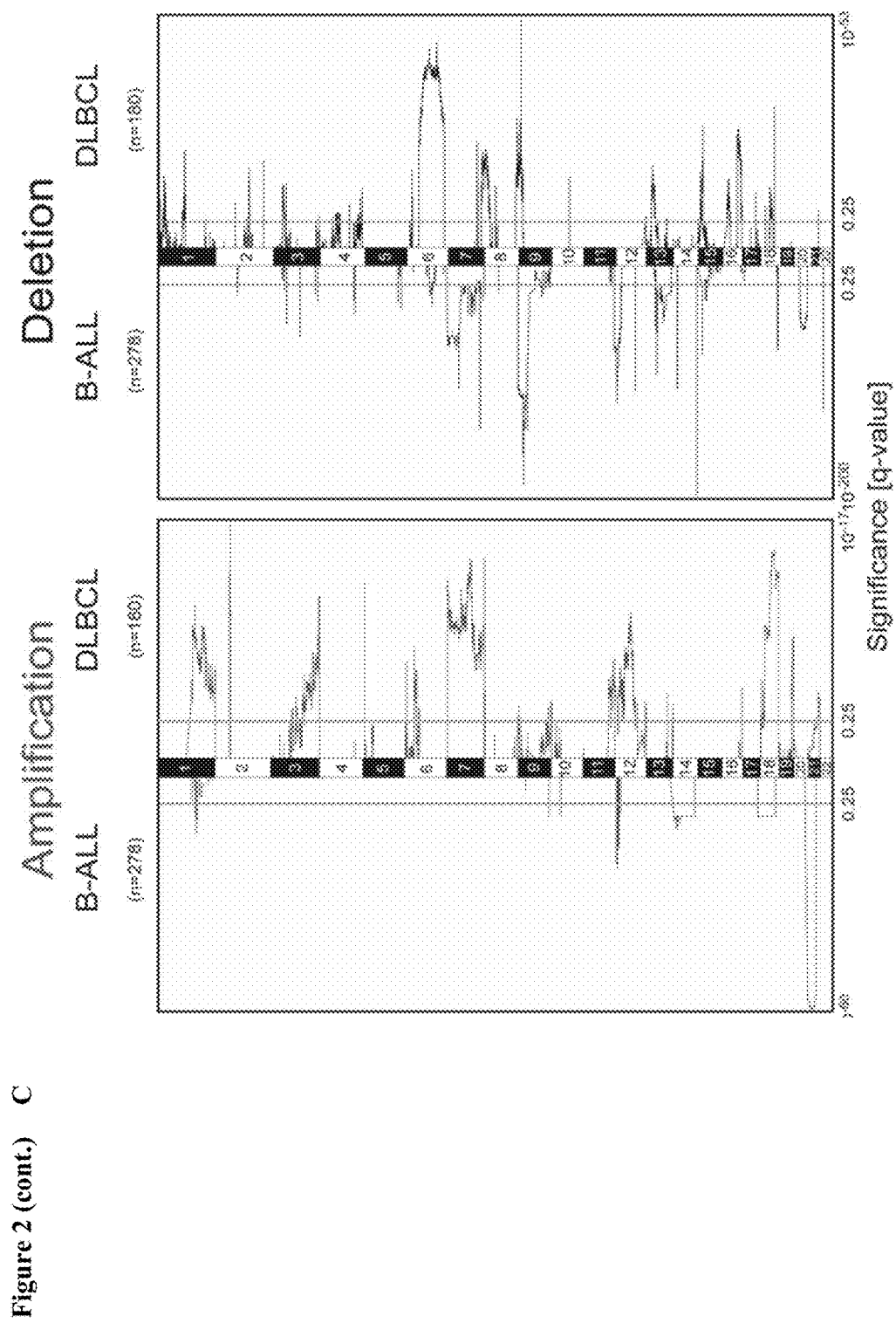
Figure 2 (cont.)  C

Figure 2 (cont.) C (cont.)
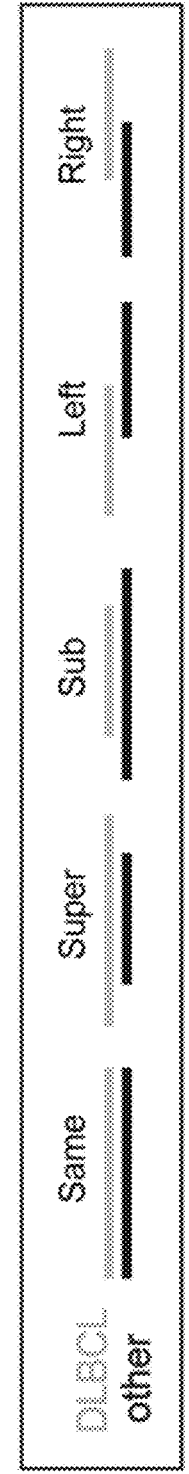

| Pathway / Category | FDR | Set annotated (out of 173) | Category annotated (out of 18580) | Hits |
|---|---|---|---|---|
| REACTOME_PEPTIDE_AND_AMINO_ACID_METABOLISM | <0.01 | 6 | 42 | LSTA1, PHPT1, POP13, PPKL, P4HB4, GAPPB |
| G1PATHWAY | 0.03 | 4 | 28 | RB1 TP53 CDKN2A CDC25A |
| REACTOME_OXIDATIVE_PHOSPHORYLATION | 0.03 | 7 | 128 | CYC1, ATP5O, UCCR, NDUFS7, NDUFV3, UGCRC1, ATP5VIB2 |
| RBPATHWAY | 0.03 | 3 | 13 | RB1 TP53 CDC25A |
| ARFPATHWAY | 0.04 | 3 | 16 | RB1 TP53 CDKN2A |
| P53PATHWAY | 0.04 | 3 | 16 | BCL2 RB1 TP53 |
| TELPATHWAY | 0.05 | 3 | 18 | BCL2 RB1 TP53 |
| HSA05030_AMYOTROPHIC_LATERAL_SCLEROSIS | 0.05 | 3 | 19 | BCL2 TP53 GPX1 |
| TIDPATHWAY | 0.05 | 3 | 19 | RB1 TP53 JAK2 |
| HSA04110_CELL_CYCLE | 0.05 | 6 | 115 | RB1 TP53 CDKN2A RBL2 CDC25A MAD1L1 |
| CELLCYCLEPATHWAY | 0.07 | 3 | 23 | RB1 CDKN2A CDC25A |
| G2PATHWAY | 0.07 | 3 | 24 | TP53 CDC25A CDC34 |
| CELL_CYCLE_KEGG | 0.07 | 5 | 90 | RB1 TP53 CDKN2A CDC25A MAD1L1 |
| HSA05223_NON_SMALL_CELL_LUNG_CANCER | 0.07 | 4 | 54 | RB1 TP53 CDKN2A RASSF5 |
| ST_PAC_1_RECEPTOR_PATHWAY ... | 0.10 | 2 | 9 | CAMP, DAG1 |
| HSA04115_P53_SIGNALING_PATHWAY ... | 0.0003 | 22** | 68 | TP53 CDKN2A SCOTIN PERP TNFRSF10B FAS RFWD2 MDM4 CCND3 CDK6 CDK4 CDK2 MDM2 PMAIP1 SESN1 CYCS EI24 CHEK1 SIAH1 ATR ZMAT3 SERPINE1 |

C

| Pathway / Category | FDR | Set annotated (out of 4353) | Category annotated (out of 18590) |
|---|---|---|---|
| SGCGSSAAA_V$E2F1DP2_01 | 0.1 | 61 | 171 |
| V$E2F_04 | 0.1 | 78 | 238 |
| V$E2F1DP2_01 | 0.1 | 77 | 239 |
| V$E2F1DP1_01 | 0.1 | 77 | 239 |
| V$E2F4DP2_01 | 0.1 | 77 | 239 |
| V$E2F_02 | 0.1 | 77 | 239 |
| V$E2F4DP1_01 | 0.1 | 78 | 243 |
| ... | | | |

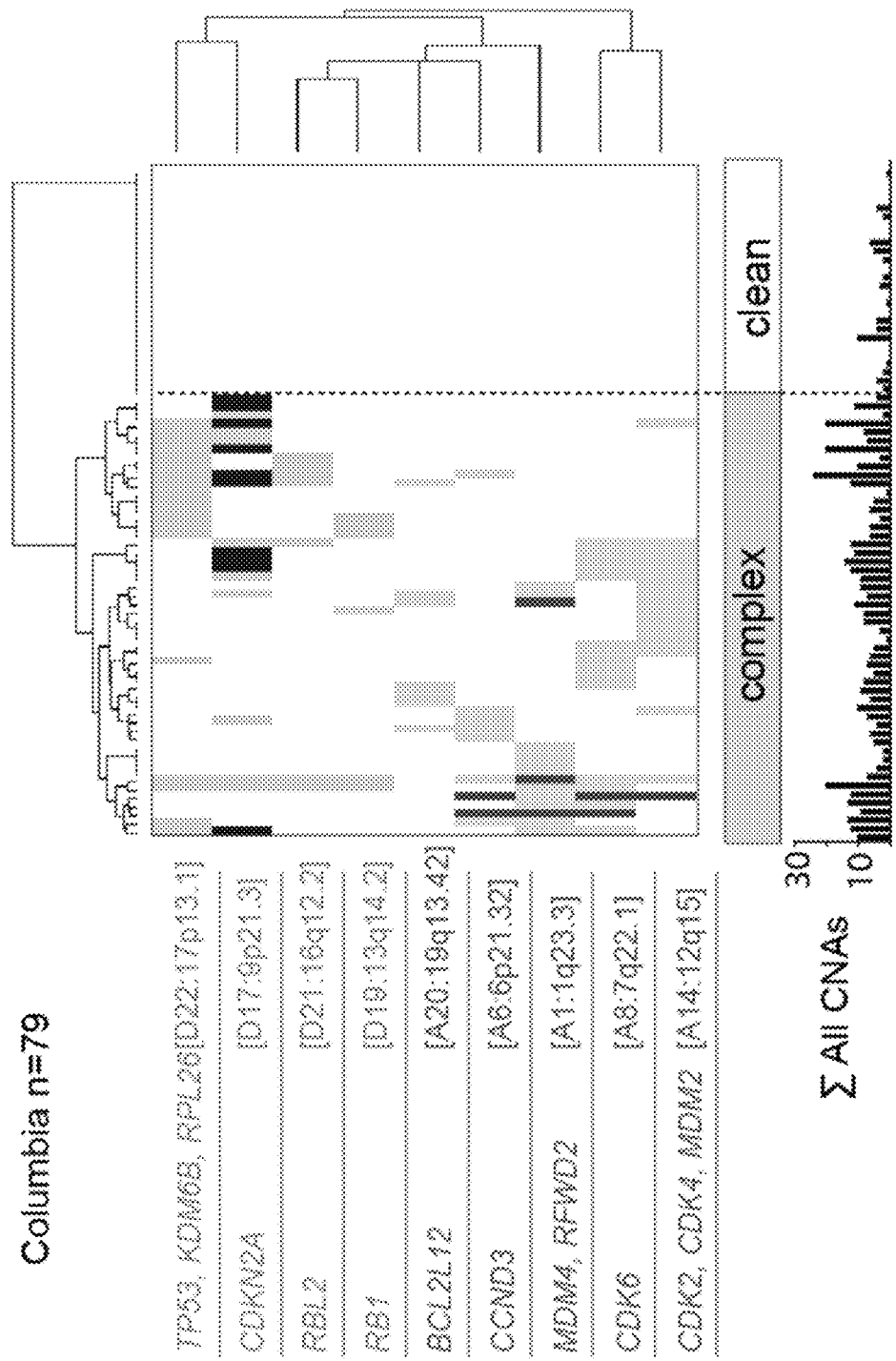
Figure 6 (cont.)  B (cont.)

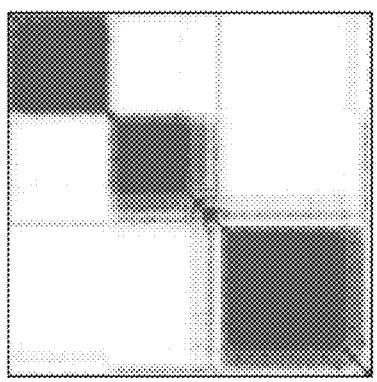

Consensus matrix generated by running consensus clustering with hierarchical clustering on the new DLBCL samples.

Confusion matrix comparing the class assignments of the ensemble classifier with the class assignments attained by Consensus clustering.

Accuracy: 86.6

B

| Cluster | Geneset | ES | P.value | FDR |
|---|---|---|---|---|
| $Cluster_1$ | HSA00190_OXIDATIVE_PHOSPHORYLATION | 0.73 | 0.000 | 0.026 |
| | OXIDATIVE_PHOSPHORYLATION | 0.66 | 0.008 | 0.112 |
| | ... | | | |
| $Cluster_2$ | SIG_BCR_SIGNALING_PATHWAY | 0.64 | 0.002 | 0.013 |
| | ST_B_CELL_ANTIGEN_RECEPTOR | 0.63 | 0.000 | 0.013 |
| | ... | | | |
| $Cluster_3$ | HSA04060_CYTOKINE_CYTOKINE_RECEPTOR_INTERACTION | 0.60 | 0.000 | 0.000 |
| | HSA04610_COMPLEMENT_AND_COAGULATION_CASCADES | 0.65 | 0.000 | 0.002 |
| | ... | | | |

COMPOSITIONS, KITS, AND METHODS FOR THE IDENTIFICATION, ASSESSMENT, PREVENTION, AND THERAPY OF CANCER

CROSS-REFERENCE TO RELATED APPLICATIONS

This application is the U.S. National Stage Application of International Application No. PCT/US2013/028297, filed on Feb. 28, 2013, which claims the benefit of U.S. Provisional Application No. 61/604,709, filed on Feb. 29, 2012; the entire contents of each of said applications is incorporated herein in its entirety by this reference.

LARGE FILES

The instant application includes the complete contents of the accompanying 8 lengthy tables, all of which are ASCII text files, as follows: Table 1, submitted herewith as "Table 1.txt", created Dec. 13, 2017 and 11,543 bytes in size; Table 2, submitted herewith as "Table 2.txt", created Dec. 13, 2017 and 2,343 bytes in size; Table 3, submitted herewith as "Table 3.txt", created Dec. 13, 2017 and 82,445 bytes in size; Table 4, submitted herewith as "Table 4.txt", created Dec. 13, 2017 and 311,810 bytes in size; Table 5, submitted herewith as "Table 5.txt", created Dec. 13, 2017 and 6,002 bytes in size; Table 6, submitted herewith as "Table 6.txt", created Dec. 13, 2017 and 34,254 bytes in size; Table 7, submitted herewith as "Table 7.txt", created Dec. 13, 2017 and 17,413 bytes in size; and Table 8, submitted herewith as "Table 8.txt", created Dec. 13, 2017 and 6,580 bytes in size. Each of these 8 tables is hereby incorporated by reference in their entireties.

BACKGROUND OF THE INVENTION

Cancer represents the phenotypic end-point of multiple genetic lesions that endow cells with a full range of biological properties required for malignancy and tumorigenesis. Indeed, a hallmark genomic feature of many cancers is the presence of complex chromosome structural aberrations, including non-reciprocal translocations, amplifications and deletions.

Karyotype analyses (Johansson, B., et al. (1992) Cancer 69, 1674-81; Bardi, G., et al. (1993) Br J Cancer 67, 1106-12; Griffin, C. A., et al. (1994) Genes Chromosomes Cancer 9, 93-100; Griffin, C. A., et al. (1995) Cancer Res 55, 2394-9; Gorunova, L., et al. (1995) Genes Chromosomes Cancer 14, 259-66; Gorunova, L., et al. (1998) Genes Chromosomes Cancer 23, 81-99), chromosomal CGH and array CGH (Wolf M et al. (2004) Neoplasia 6(3)240; Kimura Y, et al. (2004) Mod. Pathol. 21 May (epub); Pinkel, et al. (1998) Nature Genetics 20:211; Solinas-Toldo, S., et al. (1996) Cancer Res 56, 3803-7; Mahlamaki, E. H., et al. (1997) Genes Chromosomes Cancer 20, 383-91; Mahlamaki, E. H., et al. (2002) Genes Chromosomes Cancer 35, 353-8; Fukushige, S., et al. (1997) Genes Chromosomes Cancer 19:161-9; Curtis, L. J., et al. (1998) Genomics 53, 42-55; Ghadimi, B. M., et al. (1999) Am J Pathol 154, 525-36; Armengol, G., et al. (2000) Cancer Genet Cytogenet 116, 133-41), fluorescence in situ hybridization (FISH) analysis (Nilsson M et al. (2004) Int J Cancer 109(3):363-9; Kawasaki K et al. (2003) Int J Mol Med. 12(5):727-31) and loss of heterozygosity (LOH) mapping (Wang Z C et al. (2004) Cancer Res 64(1):64-71; Seymour, A. B., et al. (1994) Cancer Res 54, 2761-4; Hahn, S. A., et al. (1995) Cancer Res 55, 4670-5; Kimura, M., et al. (1996) Genes Chromosomes Cancer 17, 88-93) have identified recurrent regions of copy number change or allelic loss in various cancers.

To date, however, such techniques have been applied with relatively low resolution and without concordant assessments of transcript abundance and copy number. Thus, the precise boundaries of copy number alterations (CNAs) and the identification of the underlying genes responsible for malignant transformation remained undefined, particularly among cancers (e.g., hematological cancers) known to have complex patterns of genetic instability. For example, diffuse large B-cell lymphoma (DLBCL) is the most common non-Hodgkin lymphoma in adults and is characterized as both a clinically and genetically heterogenous disorder. With current immunochemotherapy, over 60% of patients with DLBCL can be cured. However, the remaining patients succumb to their disease (Friedberg, J. W. (2008) Hematol Oncol Clin North Am 22:941-949).

Given the numbers and types of genetic alterations in DLBCL, investigators have sought additional comprehensive classification systems to identify groups of tumors with similar molecular traits. Transcriptional profiling has been used to define DLBCL subsets that share certain features with normal B-cell subtypes ("cell-of-origin" classification, COO) (Lenz et al. (2010) New Engl J Med 362:1417-1429). COO-defined DLBCLs include "germinal center B-cell" (GCB) and "activated B-cell" (ABC) types and an additional group of unclassified tumors. The COO-defined tumor groups are characterized by certain biological features, most notably increased NFκB activity and less favorable outcome in ABC-type DLBCLs (Compagno et al. (2009) Nature 459:717-722 and Lenz et al. (2010) New Engl J Med 362:1417-1429). However, the outcome differences in GCB and ABC type DLBCLs may be less striking in patients treated with current Rituxan® (rituximab)-containing combination chemotherapy regimens (Fu et al. (2008) J Clin Oncol 26:4587-4594 and Lenz et al. (2008) New Engl J Med 359:2313-2323). An alternative transcriptional profiling classification, termed comprehensive consensus clustering (CCC), identifies DLBCL subtypes solely on the basis of distinctions within primary tumors and includes the 3 groups: "B-cell receptor" (BCR); "Oxidative Phosphorylation" (OxP); and "Host-response" (HR) (Chen et al. (2008) Blood 111:2230-2237 and Monti et al. (2005) Blood 105: 1851-1861).

Despite such recent advances in the molecular understanding of DLBCL pathogenesis, however, clinical risk factor models are still used to identify patients who are unlikely to be cured with current therapy. The most widely used model is the International Prognostic Index (IPI), which is an outcome predictor based on easily measurable clinical parameters including age, performance status, serum LDH, Ann Arbor stage and numbers of extranodal disease sites (Shipp et al. (1993) N Engl J Med 329:987-994). Although the IPI is generally robust and reproducible, the link between the included clinical parameters and underlying biology remains to be defined and improved upon. In addition, the clinical model does not provide insights regarding alternative treatment approaches for high-risk patients.

In view of the above, it is clear that there remains a need in the art for methods and compositions to identify, assess, prevent, and treat cancers (e.g., hematological cancers, including DLBCL).

SUMMARY OF THE INVENTION

The present invention overcomes the long-felt difficulties in identifying, assessing, preventing, and treating cancers (e.g., hematological cancers, including DLBCL).

In one aspect, a method of determining whether a subject is afflicted with a cancer or at risk for developing a cancer is provided, wherein the method comprises a) determining the copy number, level of expression, or level of activity of one or more biomarkers listed in Tables 1-9 or a fragment thereof in a subject sample; b) determining the normal copy number, level of expression, or level of activity of the one or more biomarkers in a control sample; and c) comparing the copy number, level of expression, or level of activity of said one or more biomarkers detected in steps a) and b), wherein a significant modulation in the copy number, level of expression, or level of activity of the one or more biomarkers in the subject sample relative to the normal copy number, level of expression, or level of activity of the one or more biomarkers in a control sample is an indication that the subject is afflicted with the cancer or is at risk for developing the cancer. In one aspect, significant modulation comprises an at least twenty percent increase or an at least twenty percent decrease between the copy number, level of expression, or level of activity of the biomarker in the subject sample relative to the normal copy number, level of expression, or level of activity of the biomarker in the sample from the control subject.

In another aspect, a method for monitoring the progression of a cancer in a subject is provided, wherein the method comprises a) detecting in a subject sample at a first point in time the copy number, level of expression, or level of activity of one or more biomarkers listed in Tables 1-9 or a fragment thereof; b) repeating step a) at a subsequent point in time; and c) comparing the copy number, level of expression, or level of activity of said one or more biomarkers detected in steps a) and b) to monitor the progression of the cancer. In one embodiment, an at least twenty percent increase or an at least twenty percent decrease between the copy number, level of expression, or level of activity of the one or more biomarkers in the subject sample at a first point in time relative to the copy number, level of expression, or level of activity of the one or more biomarkers in the subject sample at a subsequent point in time indicates progression of the cancer. In another embodiment, less than a twenty percent increase or less than a twenty percent decrease between the copy number, level of expression, or level of activity of the one or more biomarkers in the subject sample at a first point in time relative to the copy number, level of expression, or level of activity of the one or more biomarkers in the subject sample at a subsequent point in time indicates a lack of significant progression of the cancer. In still another embodiment, the subject has undergone treatment to ameliorate the cancer between the first point in time and the subsequent point in time.

In still another aspect, a method for stratifying subjects afflicted with a cancer according to predicted clinical outcome is provided, wherein the method comprises a) determining the copy number, level of expression, or level of activity of one or more biomarkers listed in Tables 1-9 or a fragment thereof in a subject sample; b) determining the normal copy number, level of expression, or level of activity of the one or more biomarkers in a control sample; and c) comparing the copy number, level of expression, or level of activity of said one or more biomarkers detected in steps a) and b); wherein a significant modulation in the copy number, level of expression, or level of activity of the one or more biomarkers in the subject sample relative to the normal copy number, level of expression, or level of activity of the one or more biomarkers in the control sample predicts the clinical outcome of the patient. In one embodiment, the predicted clinical outcome is (a) prognosis determined using the international prognostic index (IPI) risk model, (b) cellular proliferation, or (c) survival time resulting from treatment with one ore more therapeutic agents selected from the group consisting of Rituxan® (rituximab), cyclophosphamide, Adriamycin® (doxorubicin), Oncovin® (vincristine), prednisone, or a chemotherapeutic. In another embodiment, an at least twenty percent increase or an at least twenty percent decrease between the copy number, level of expression, or level of activity of the one or more biomarkers in the subject sample compared to the control sample predicts that the subject has a poor clinical outcome. In still another embodiment, the method further comprises treating the subject with a therapeutic agent that specifically modulates the copy number, level of expression, or level of activity of the one or more biomarkers. In yet another embodiment, less than a twenty percent increase or less than a twenty percent decrease between the copy number, level of expression, or level of activity of the one or more biomarkers in the subject sample compared to the control sample predicts that the subject has a favorable clinical outcome. In another embodiment, the method further comprises treating the subject with one ore more therapeutic agents selected from the group consisting of Rituxan® (rituximab), cyclophosphamide, Adriamycin® (doxorubicin), Oncovin® (vincristine), prednisone, or a chemotherapeutic.

In yet another aspect, a method of determining the efficacy of a test compound for inhibiting a cancer in a subject is provided, wherein the method comprises a) determining the copy number, level of expression, or level of activity of one or more biomarkers listed in Tables 1-9 or a fragment thereof in a first sample obtained from the subject and exposed to the test compound; b) determining the copy number, level of expression, or level of activity of the one or more biomarkers in a second sample obtained from the subject, wherein the second sample is not exposed to the test compound, and c) comparing the copy number, level of expression, or level of activity of the one or more biomarkers in the first and second samples, wherein a significantly modulated copy number, level of expression, or level of activity of the biomarker, relative to the second sample, is an indication that the test compound is efficacious for inhibiting the cancer in the subject. In one embodiment, significant modulation comprises an at least twenty percent increase or an at least twenty percent decrease between the copy number, level of expression, or level of activity of the biomarker in the first subject sample relative to the second subject sample. In another embodiment, the first and second samples are portions of a single sample obtained from the subject or portions of pooled samples obtained from the subject.

In another aspect, a method of determining the efficacy of a therapy for inhibiting a cancer in a subject is provided, wherein the method comprises a) determining the copy number, level of expression, or level of activity of one or more biomarkers listed in Tables 1-9 or a fragment thereof in a first sample obtained from the subject prior to providing at least a portion of the therapy to the subject; b) determining the copy number, level of expression, or level of activity of the one or more biomarkers in a second sample obtained from the subject following provision of the portion of the therapy; and c) comparing the copy number, level of expression, or level of activity of the one or more biomarkers in the first and second samples, wherein a significantly modulated copy number, level of expression, or level of activity of the one or more biomarkers in the second sample, relative to the first sample, is an indication that the therapy is efficacious for inhibiting the cancer in the subject. In one embodiment, the therapy further comprises standard of care therapy for treating the cancer.

In still another aspect, a method for identifying a compound which inhibits a cancer is provided, wherein the method comprises a) contacting one or more biomarkers listed in Tables 1-9 or a fragment thereof with a test compound; and b) determining the effect of the test compound on the copy number, level of expression, or level of activity of the one ore more biomarkers to thereby identify a compound which inhibits the cancer. In one embodiment, an at least twenty percent increase or an at least twenty percent decrease between the copy number, level of expression, or level of activity of the one or more biomarkers in the presence of the test compound relative to the copy number, level of expression, or level of activity of the one or more biomarkers in the absence of the test compound identifies a compound which inhibits the cancer. In another embodiment, the one or more biomarkers is expressed on or in a cell (e.g., cells isolated from an animal model of a cancer or cells from a subject afflicted with a cancer).

In yet another aspect, a method for inhibiting a cancer is provided, wherein the method comprises contacting a cell with an agent that modulates the copy number, level of expression, or level of activity of one or more biomarkers listed in Tables 1-9 or a fragment thereof to thereby inhibit the cancer. In one embodiment, the copy number, level of expression, or level of activity of the one or more biomarkers is downmodulated. In another embodiment, the copy number, level of expression, or level of activity of the one or more biomarkers is upmodulated. In still another embodiment, the step of contacting occurs in vivo, ex vivo, or in vitro. In yet another embodiment, the method further comprises contacting the cell with an additional agent that inhibits the cancer.

In another aspect, a method for treating a subject afflicted with a cancer is provided, wherein the method comprises administering an agent that modulates the copy number, level of expression, or level of activity of one or more biomarkers listed in Tables 1-9 or a fragment thereof such that the cancer is treated. In one embodiment, the copy number, level of expression, or level of activity of the one or more biomarkers is downmodulated. In another embodiment, the copy number, level of expression, or level of activity of the one or more biomarkers is upmodulated. In still another embodiment, the step of contacting occurs in vivo, ex vivo, or in vitro. In yet another embodiment, the method further comprises contacting the cell with an additional agent that inhibits the cancer. In another embodiment, the agent is an inhibitor of one or more cyclin dependent kinases (for example and without limitation, human CDK1, CDK2, CDK3, CDK4, CDK5, CDK6, CDK7, CDK9, and CDK11 and orthologs thereof in other species).

In still another aspect, a pharmaceutical composition comprising a polynucleotide encoding one or more biomarkers listed in Tables 1-9 or a fragment thereof useful for treating cancer in a pharmaceutically acceptable carrier is provided. In one embodiment, the polynucleotide encoding the one or more biomarkers listed in Tables 1-9 or a fragment thereof further comprises an expression vector.

In yet another aspect, a method of using pharmaceutical compositions described herein for treating a cancer are provided.

In another aspect, kits comprising agents described herein are provided. For example, a kit comprising an agent which selectively binds to one or more biomarkers listed in Tables 1-9 or a fragment thereof and instructions for use is provided. In addition, a kit comprising an agent which selectively hybridizes to a polynucleotide encoding one or more biomarkers listed in Tables 1-9 or fragment thereof and instructions for use are provided.

In still another aspect, a biochip comprising a solid substrate is provided, wherein the substrate comprises a plurality of probes capable of detecting one or more biomarkers listed in Tables 1-9 or a fragment thereof and wherein each probe is attached to the substrate at a spatially defined address. In one embodiment, the probes are complementary to a genomic or transcribed polynucleotide associated with the one or more biomarkers.

In yet another aspect, any of the methods of the present invention can benefit from additional or preferred embodiments. For example, in one embodiment, the subject is human. In another embodiment, the one or more biomarkers are selected from the group of biomarkers listed in FIG. 5A. In still another embodiment, the sample comprises cells, tissue, blood, plasma, serum, buccal scrape, saliva, cerebrospinal fluid, urine, stool, mucus, or bone marrow, obtained from the subject. In yet another embodiment, the copy number is assessed by microarray, quantitative PCR (qPCR), high-throughput sequencing, comparative genomic hybridization (CGH), or fluorescent in situ hybridization (FISH). In another embodiment, the normal copy number is obtained from a control sample. In still another embodiment, the expression level of the one or more biomarkers is assessed by detecting the presence in the samples of a polynucleotide molecule encoding the biomarker or a portion of said polynucleotide molecule (e.g., a mRNA, cDNA, or functional variants or fragments thereof). In yet another embodiment, the step of detecting further comprises amplifying the polynucleotide molecule. In another embodiment, the expression level of the one or more biomarkers is assessed by annealing a nucleic acid probe with the sample of the polynucleotide encoding the one or more biomarkers or a portion of said polynucleotide molecule under stringent hybridization conditions. In still another embodiment, the expression level of the biomarker is assessed by detecting the presence in the samples of a protein of the biomarker, a polypeptide, or protein fragment thereof comprising said protein. In yet another embodiment, the presence of a protein, polypeptide or protein fragment thereof is detected using a reagent which specifically binds with said protein, polypeptide or protein fragment thereof (e.g., an antibody, an antibody derivative, or an antibody fragment). In another embodiment, the activity level of the biomarker is assessed by determining the magnitude of modulation of the activity or expression level of downstream targets of the one or more biomarkers. In still another embodiment, the cancer is a hematological cancer (e.g., a lymphoma such as diffuse large B-cell lymphoma).

BRIEF DESCRIPTION OF THE DRAWINGS

FIGS. 2A-2B; Beroukhim et al. (2010) Nature 463:899-905) and 278 B-ALLs (FIG. 2C; Beroukhim et al. (2010) Nature 463:899-905) from a publicly available database in a mirror plot with chromosome position on the Y-axis, significance (q value) on the X-axis, CN gain (left panel) and CN loss (right panel). The vertical lines adjacent to the chromosome numbers denote FDR values <0.25. The overlap of identified recurrent CNAs in DLBCL and non-hematologic cancers (FIGS. 2A-2B) and B-ALLs (FIG. 2C) was formally compared (overlap plots below mirror plots as explained in Example 1). There were identical matches ("same"), smaller ("sub") or larger ("super") alterations. Certain alterations were aligned in such a way as to have partial overlap ("right" and "left"). For each DLBCL peak, the overlap pattern with non-hematologic cancers (FIGS. 2A-2B) and B-ALLs (FIG. 2C) is summarized. Alterations are defined as unique to DLBCL or as having partial overlap or shared (>95%) identity with other cancers.

FIG. 3A shows a schema for pathway (i) and TF binding site (ii) enrichment. Pathway analysis. For each GISTIC peak and region, a 'cis-acting gene signature' was defined which included the genes within a GISTIC alteration with a significant (FDR<0.25) correlation between CN and gene expression (left panel). The global cis-acting signature—the union of all individual cis-acting signatures—was analyzed for pathway enrichment using a pathway compendium (C2, MsigDB). TF binding site analysis schema. The "trans-acting signature" of each CNA (those genes outside the CNA with the most significant association between transcript abundance and the CNA) was defined (left panel) and the union of the cis- and trans-acting signatures was then tested for enrichment of genes with common TF binding sites using a publicly available curated TF binding site compendium (C3, MsigDB). FIG. 3B shows the results of pathway analysis (i.e., the results of global cis-acting signature pathway enrichment), separated for peaks (upper panel) and regions (lower panel), which were ranked by FDR (FDR≤0.10, peaks; top set, region; amplified genes in light shading, deleted genes in dark shading; full list shown in Table 7). In the region pathway analysis, the set annotation is "out of 1893" instead of "out of 173" (**). FIG. 3C shows the results of TF binding site analysis. The results were ranked by FDR (FDR≤0.1 shown; full list shown in Table 8).

FIG. 5A shows primary DLBCLs clustered in the space of CNAs that alter p53 pathway and cell cycle components. CNAs and perturbed genes on the left (rows) and individual tumors on top (columns). CN gains are shown in light shading, CN losses are shown in dark shading, and the color intensity corresponds to the magnitude of the CNA. Tumors with CNAs of multiple p53 pathway and cell cycle components are indicated as "complex," whereas DLBCLs without these lesions are indicated as "clean." Total CNAs (Σ all CNAs) in "complex" vs. "clean" DLBCLs are shown under the heat map (p<0.0001, Mann Whitney U test). TP53 mutations in "complex" vs. "clean" DLBCLs are shown at the top (22% vs. 7%, p<0.005, Fisher's one-sided exact test). FIG. 5B shows GSEA of p53 targets in "clean" vs. "complex" DLBCLs. The 19K genes in the genome were sorted from highest (left, white) to lowest (right, grey) relative expression in "clean" vs. the "complex" DLBCLs (horizontal axis). The p53 targets (V.P53_02, described in FIG. 6C) were located within the sorted genome and their positions (hits) were found to be significantly skewed toward the left end of the sorted list (positive enrichment score, 0.31), reflecting their statistically significant overexpression in "clean" as compared to "complex" DLBCLs (p=0.01). FIG. 5C shows GSEA of a RB deficiency gene set in "complex" vs. "clean" DLBCLs. GSEA was performed as in FIG. 5B except that genes were sorted from highest to lowest expression in "complex" vs. "clean" DLBCLs (horizontal axis). The positions of RB-deficiency gene set members (hits) were significantly skewed toward the left end of the sorted list reflecting their overexpression in "complex" DLBCLs (positive enrichment score 0.79, p<0.001). FIG. 5D shows the results of Ki67 immunohistochemistry of "complex" and "clean" DLBCLs, wherein representative "clean" (upper micrographs) and "complex" DLBCLs (lower micrographs) images are shown in the left panel (scale bar represents 50 rpm). The right panel shows the percentage of Ki67-positive tumor cells in "complex" and "clean" DLBCLs (p=0.019, Mann Whitney U test) visualized as a box-plot (median, line: 25% and 75% quartile, box: whiskers, minimum to maximum; see also FIG. 6 and Table 6). FIG. 5E shows the overall survival of R-CHOP treated DLBCL patients with "complex" vs. "clean" CNA patterns (p=0.001, log rank test). FIG. 5F shows CNA patterns in IPI risk groups. The left panel shows the overall survival of R-CHOP treated DLBCL patients in Low/Low-intermediate and High-intermediate/High IPI risk groups. The middle and right panels show the overall survival of Low/Low-intermediate and High-intermediate/High-risk patients with "complex" vs. "clean" CNA patterns.

FIG. 6A shows a heat map of all CNAs among 180 primary DLBCLs. Supervised hierarchical clustering of all significant CNAs across the 180 primary DLBCLs is shown. CNAs are listed on the left (rows) and individual tumors are represented in columns at top (tumor order as in FIG. 5). CN gains are shown in light shading and CN losses are shown in dark shading. The color intensity corresponds to the magnitude of the CNA. Total CNAs (Σ all CNAs) in "complex" vs. "clean" DLBCLs under the heat map (p<0.0001, Mann Whitney U Test) are shown. The heat map header includes additional information on TP53 mutations. The Presence or absence of a mutation is noted. Cases with unavailable information are depicted in grey. TP53 mutation frequency in the "complex" vs. "clean" DLBCLs is 22% vs. 7% (p<0.005, Fisher's one-sided exact test). The header also includes tumor assignments to transcriptionally defined subtypes (CCC/COO). FIG. 6B shows confirmation of the "complex" vs. "clean" CNA pattern in an independent series of primary DLBCLs. Primary DLBCLs (n=79) were analyzed on Affymetrix 6.0 HD SNP arrays as described in Pasqualucci et al. (2011) Nature Genetics 43:830-837. FIG. 6B(a) shows a comparison of recurrent CNAs in the current series (right) and the independent series (left) by mirror plot. CN gains (amplification, left) and CN losses (deletion, right) are shown. FIG. 6B(b) shows that an independent series of DLBCLs clustered in the space of CNAs that alter p53 pathway and cell cycle components. Total CNAs (Σ all CNAs) in "complex" vs. "clean" DLBCLs (p<0.0001, Mann Whitney U test) is shown. FIG. 6C shows GSEA results of p53 target genes in "clean" vs. "complex" DLBCLs (current series). The 19K+ genes in the genome were sorted from highest (left, white) to lowest (right, grey) expression as measured in the "clean" class compared to the "complex" class (horizontal axis). The p53 targets were then located within the sorted genome, and their positions (hits) were shown to be significantly skewed toward the left-end of the sorted list (positive enrichment score), reflecting their statistically significant over-expression in the "complex" class. The two p53 target gene sets are part of the MSigDB c3 TFT collection (available on the world wide web at the broadinstitute.org). This collection consists of gene sets containing transcription factor target (TFT) genes that share a transcription factor binding site as defined in the TRANSFAC database. In particular, the V$P53_02 gene set, which is available on the world wide web at the broadinstitute.org using the keywords "V$P53_02" and "P53," includes all genes with promoter regions [−2 kb, 2 kb] around a transcription start site containing the motif NGRCWTGYCY, which matches annotation for TP53. Similarly, the V$P53_DECAMER_Q2 gene set, which is available on the world wide web at the broadinstitute.org using the keywords "V$P53_DECAMERQ2" and "P53," includes all genes with promoter regions [−2 kb, 2 kb] around a transcription start site containing the motif RGRCAWGNCY, which also matches annotation for TP53. The two gene sets contain 195 and 201 genes, respectively, with 70 genes in common between the two.

FIG. 9A shows proliferation data following flavopiridol treatment (50 nM-400 nM) for 1-4 days. DLBCL cell lines names at top. FIG. 9B shows cell cycle analysis following 72 hr flavopiridol treatment (400 nM) (DMSO control). FIG. 9C shows apoptosis (Annexin V staining) data following 72 hr flavopiridol treatment (100-400 nM). FIG. 9D shows RB1 phosphorylation at CDK4/6 and CDK2-specific sites (pS870 and pT821, respectively) following 24 hr flavopiridol treatment (100-400 nM). FIGS. 9E-9H show additional data from experiments performed according to FIGS. 9A-9D.

RB1 is itself an E2F target (Knudsen et al. (2008) Nat Rev Cancer 8:714-724) and error bars show the standard deviation (SD) of triplicates.

FIGS. 10A-10D show the results of treating DLBCL cell lines with a second pan-CDK inhibitor, AT-7519. The cell lines were treated with 50-400 nM of AT-7519 (Selleck Chemicals) or vehicle control DMSO for 1-4 days and evaluated thereafter. Proliferation (FIG. 10A), cell cycle (FIG. 10B), and apoptosis (FIG. 10C) results following 72 hr AT7519 (200-1600 nM) or vehicle (DMSO) treatment are shown. FIG. 10D shows RB1 phosphorylation at CDK4/6 and CDK2-specific sites (pS780 and pT821, respectively) following 24 hr AT7519 (400-1600 nM) or vehicle (DMSO) treatment. Rb is itself an E2F target (Knudsen et al. (2008) Nat Rev Cancer 8:714-724) and error bars show the standard deviation (SD) of triplicates.

Figure 11:
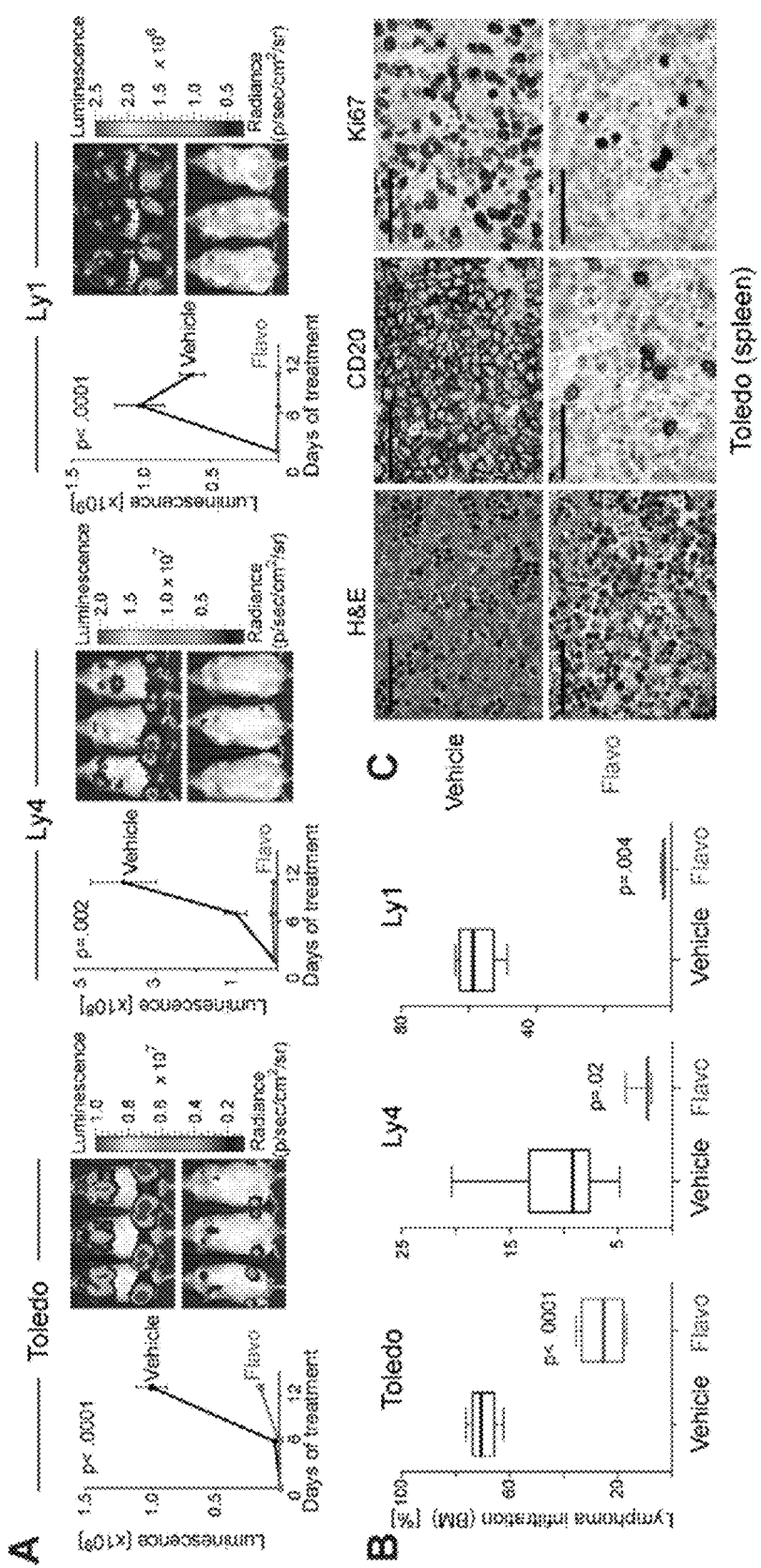
Figure 11:
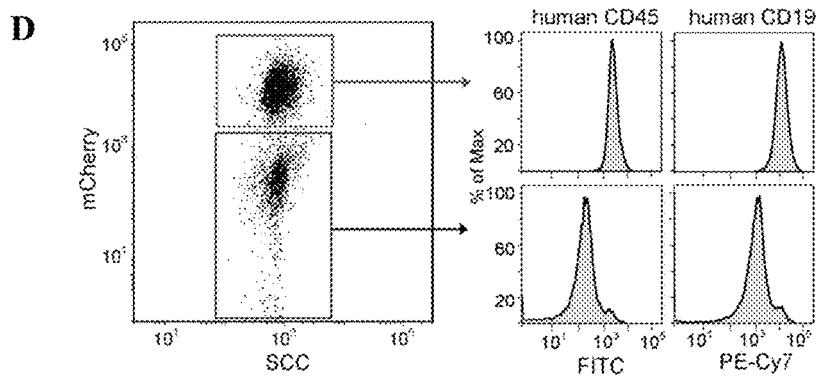

FIGS. 11A-11D show in vivo efficacy of a pan-CDK inhibitor in DLBCL xenografts. FIG. 11A shows bioluminescence of flavopiridol- or vehicle-treated NSG mice xenotransplanted with luciferized mCherry$^+$ (Toledo, Ly4 or Ly1) DLBCL cells. Error bars show the SEM. FIG. 11B shows lymphoma infiltration in the bone marrow of NSG mice (in FIG. 11A) following flavopiridol or vehicle treatment. Single cell suspensions of bone marrow of tumor-bearing mice were evaluated for mCherry$^+$ DLBCL cells by flow cytometry and visualized as Box-Plot (median, line; 25% and 75% quartile, box; whiskers, minimum to maximum). P values were obtained with a Mann Whitney U test. FIG. 11C shows the results of immunohistochemical analysis of lymphoma (Toledo) cell infiltration in spleens of vehicle- and flavopiridol-treated mice: H & E; Anti-human CD20, and anti-Ki67 immunostaining. Scale bar represents 50 μm. FIG. 11D shows phenotyping results of mCherry$^+$ lymphoma cells from the bone marrow of xenotransplanted mice. The mCherry$^+$ human DLBCL cell lines expressed human CD45 and CD19. The Toledo DLBCL cell line is shown here.

Figure 12:
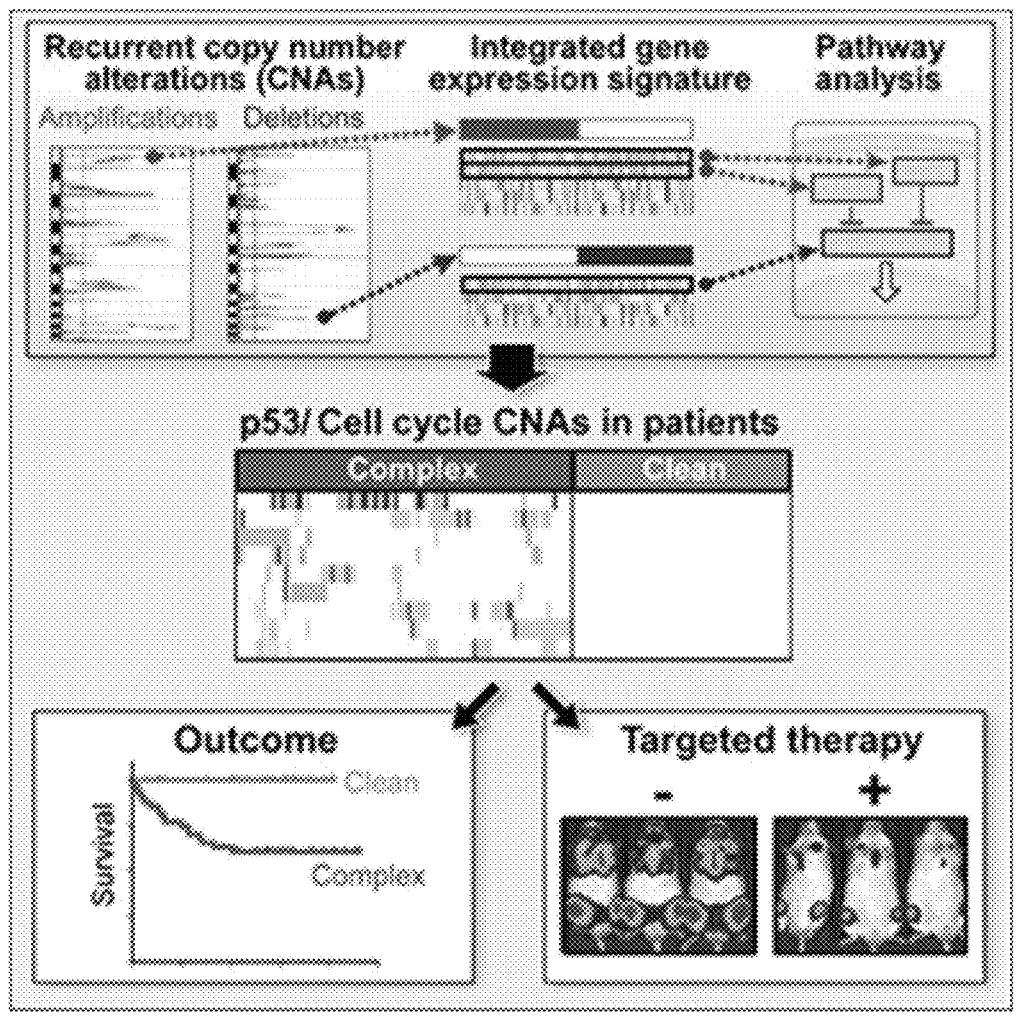

FIG. 12 shows a representative schematic of the methodological analyses described herein.

FIGS. 13A-13B provide a representative schematic of de novo clustering of samples (FIG. 13A) and GSEA results of clusters (FIG. 13B) described herein.

BRIEF DESCRIPTION OF THE TABLES

Table 1 shows peak and region boundaries, top genes, frequencies of alterations and association with transcriptionally defined DLBCL subtypes. For each of the identified 21 CN gains and 26 CN losses, the boundaries of the GISTIC peak and region, the chromosome band and alteration frequency and the top 5 genes in peaks and regions by integrative analysis of copy number and transcript abundance are listed. Each alteration was tested for enrichment in transcriptionally defined subtypes (CCC and COO). In addition, frequency, p-value and FDR corrected q value data are listed.

Table 2 shows a comparison of CNAs in DLBCLs and non-hematologic cancers. The overlap of identified recurrent CNAs in DLBCL and non-hematologic cancers was formally compared. There were identical matches ('same'), larger ('sub') or smaller ('super') alterations. Certain alterations were aligned in such a way as to have partial overlap ('right' and 'left'). For each DLBCL peak, the overlap pattern with non-hematologic cancers is summarized. Alterations were defined as unique to DLBCL or as having partial overlap or shared (≥95%) identity with non-hematologic cancers.

Table 3 shows genes included in GISTIC-defined recurrent CNAs. All genes physically located within GISTIC-defined CNA peaks and regions are listed.

Table 4 shows the results of integrative analysis. Results of the integrative analysis between copy number and gene expression were ranked by FDR and thresholded at 0.25. Results are reported separately for GISTIC-defined peaks and regions of CN gains and losses.

Table 5 shows summary statistics. Each alteration is separated by amplification and deletion and the numbers of genes meeting different FDR thresholds for cis- and trans-analyses are summarized.

Table 6 shows assignment of CCC/COO. A summary spreadsheet assigning all cases to previously defined transcriptional subtypes is provided.

Table 7 shows the results of pathway enrichment. A full pathway analysis list ranked by FDR and thresholded at 0.25 is provided.

Table 8 shows the results of transcription factor binding site enrichment. A Full transcription factor binding site enrichment analysis is provided, wherein the list is ranked by FDR and thresholded at 0.25.

Table 9 shows the characteristics of R-CHOP-treated DLBCL patients with long-term follow up. The age at diagnosis, sex, median OS time, IPI risk groups, COO and CCC distribution for all patients treated with R-CHOP is provided. In addition, the IPI risk groups are listed separately for the clean and complex DLBCLs.

Table 10 provides summary statistics of samples analyzed via high-density single nucleotide polymorphism (HD SNP) array.

DETAILED DESCRIPTION OF THE INVENTION

The invention is based, at least in part, on the novel discovery of copy number alterations (CNA) and gene profiles useful for distinguishing among cancer subtypes and for predicting the clinical outcome of such cancer subtypes to therapeutic regimens. Thus, agents such as miRNAs, miRNA analogues, small molecules, RNA interference, aptamer, peptides, peptidomimetics, antibodies that specifically bind to one or more biomarkers of the invention (e.g., biomarkers listed in Tables 1-9) and fragments thereof can be used to identify, diagnose, prognose, assess, prevent, and treat cancers (e.g., hematological cancers, including DLBCL).

I. Definitions

The articles "a" and "an" are used herein to refer to one or to more than one (i.e. to at least one) of the grammatical object of the article. By way of example, "an element" means one element or more than one element.

The term "altered amount" of a marker or "altered level" of a marker refers to increased or decreased copy number of the marker and/or increased or decreased expression level of a particular marker gene or genes in a cancer sample, as compared to the expression level or copy number of the marker in a control sample. The term "altered amount" of a marker also includes an increased or decreased protein level of a marker in a sample, e.g., a cancer sample, as compared to the protein level of the marker in a normal, control sample.

The "amount" of a marker, e.g., expression or copy number of a marker or minimal common region (MCR), or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker. In some embodiments, the amount of the marker in the subject can be considered "significantly" higher or lower than the normal amount if the amount is 10%, 15%, 20%, 25%, 30%, 35%, 40%, 45%, 50% or more, higher or lower, respectively, than the normal amount of the marker. For example, while for any given diploid gene, 2 copies are normal, significant copy number gains or losses can be defined as $t_{amp}$=2.46 or greater for amplifications and/or $t_{del}$=1.62 or greater for deletions (corresponding to $2^{x+1}$ for x=+/−0.3).

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered subcellular localization" of a marker refers to the mislocalization of the marker within a cell relative to the normal localization within the cell e.g., within a healthy and/or wild-type cell. An indication of normal localization of the marker can be determined through an analysis of subcellular localization motifs known in the field that are harbored by marker polypeptides.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

The term "biochip" refers to a solid substrate comprising an attached probe or plurality of probes of the invention, wherein the probe(s) comprise at least 1, 2, 3, 4, 5, 6, 7, 8, 9, 10, 11, 12, 13, 14, 15, 16, 17, 18, 19, 20, 25, 30, 35, 40, 45, 50, 100, 150, 200 or more probes. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder. The probes may be attached to the biochip in a wide variety of ways, as will be appreciated by those in the art. The probes may either be synthesized first, with subsequent attachment to the biochip, or may be directly synthesized on the biochip. The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing. The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics. The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide. The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit).

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostrate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis of lymphoma or its subtypes, including, but not limited to, lymphocyte-rich classical Hodgkin lymphoma, mixed cellularity classical Hodgkin lymphoma, lymphocyte-depleted classical Hodgkin lymphoma, nodular sclerosis classical Hodgkin lymphoma, anaplastic large cell lymphoma, diffuse large B-cell lymphomas, MLL$^+$ pre B-cell ALL) based upon analysis of markers described herein.

The term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, CHOP or R-CHOP). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, for example, CHOP or R-CHOP, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing R-CHOP therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The term "diagnosing cancer" includes the use of the methods, systems, and code of the present invention to determine the presence or absence of a cancer or subtype thereof in an individual. The term also includes methods, systems, and code for assessing the level of disease activity in an individual.

As used herein, the term "diagnostic marker" includes markers described herein which are useful in the diagnosis of cancer, e.g., over- or under-activity, emergence, expression, growth, remission, recurrence or resistance of tumors before, during or after therapy. The predictive functions of the marker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression (e.g., by ISH, Northern Blot, or qPCR), increased or decreased protein level (e.g., by IHC), or increased or decreased activity (determined by, for example, modulation of a pathway in which the marker is involved), e.g., in more than about 5%, 6%, 7%, 8%, 9%, 10%, 11%, 12%, 13%, 14%, 15%, 20%, 25%, or more of human cancers types or cancer samples; (2) its presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its presence or absence in clinical subset of subjects with cancer (e.g., those responding to a particular therapy or those developing resistance). Diagnostic markers also include "surrogate markers," e.g., markers which are indirect markers of cancer progression.

The term "diffuse large B-cell lymphoma" or "DLBCL" refers to a class of lymphoma distinguished as a molecularly heterogeneous condition. Traditionally, gene expression profiling has identified two molecular subtypes of DLBCL that are biologically and clinically distinct (Rosenwald et al., N. Engl. J. Med., 346: 1937-47 (2002); Alizadeh et al., Nature, 403: 503-11 (2000)). The germinal center B cell-like (GCB) DLBCL subtype likely arises from normal germinal center B cells, whereas the activated B cell-like (ABC) DLBCL subtype may arise from a post-germinal center B cell that is blocked during plasmacytic differentiation. Certain genetic alterations are more common in specific subtypes: GCB DLBCLs have recurrent t(14,18) translocations, whereas ABC DLBCLs more often have recurrent trisomy 3 and deletion of the INK4a/ARF locus as well as constitutive activation of the anti-apoptotic NF-kB signalling pathway (Rosenwald et al., N. Engl. J. Med., 346: 1937-47 (2002); Bea et al., Blood, 106: 3183-90 (2005); Tagawa et al., Blood, 106: 1770-77 (2005); Davis et al., J. Exp. Med., 194:1861-74 (2001); Ngo et al., Nature, 441: 106-10 (2006); Lenz et al., Science, 319: 1676-79 (2008)). The current standard of care for the treatment of diffuse large B cell lymphoma (DLBCL) includes anthracycline-based chemotherapy regimens such as CHOP in combination with the administration of the anti-CD20 monoclonal antibody Rituximab. This combination regimen (R-CHOP) can cure about 60% of patients and has improved the overall survival of DLBCL patients by 10-15% (Coiffier et al., N. Engl. J. Med., 346: 235-42 (2002)).

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

The term "gene expression data" or "gene expression level" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. Gene expression data may be acquired for an individual cell, or for a group of cells such as a tumor or biopsy sample. Gene expression data and gene expression levels can be stored on computer readable media, e.g., the computer readable medium used in conjunction with a microarray or chip reading device. Such gene expression data can be manipulated to generate gene expression signatures.

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer (Shaffer et al., Immunity, 15: 375-385 (2001)). Examples of gene expression signatures include lymph node, proliferation (Rosenwald et al., New Engl. J. Med., 346: 1937-1947 (2002)), MHC class II, ABC DLBCL high, B cell differentiation, T-cell, macrophage, immune response-1, and immune response-2 signatures (U.S. Patent Application Publication No. 2007/0105136 (Staudt)).

The term "hematological cancer" refers to cancers of cells derived from the blood. In some embodiments, the hematological cancer is selected from the group consisting of acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), Hodgkin's lymphoma, mantle cell lymphoma (MCL), follicular lymphoma, Waldenstrom's macroglobulinemia (WM), B-cell lymphoma and diffuse large B-cell lymphoma (DLBCL). NHL may include indolent Non-Hodgkin's Lymphoma (iNHL) or aggressive Non-Hodgkin's Lymphoma (aNHL).

The term "homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody," as used herein, is intended to include antibodies made by a non-human cell having variable and constant regions which have been altered to more closely resemble antibodies that would be made by a human cell, for example, by altering the non-human antibody amino acid sequence to incorporate amino acids found in human germline immunoglobulin sequences. Humanized antibodies may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

As used herein, the term "inhibit" includes the decrease, limitation, or blockage, of, for example a particular action, function, or interaction. For example, cancer is "inhibited" if at least one symptom of the cancer, such as hyperproliferative growth, is alleviated, terminated, slowed, or prevented. As used herein, cancer is also "inhibited" if recurrence or metastasis of the cancer is reduced, slowed, delayed, or prevented.

As used herein, the term "interaction," when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules. Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

The term "international prognostic index" or "IPI" refers to a set of standard clinical criteria used to prognose treatment outcome of DLBCL patients. Techniques and methodology for calculation of IPI to assign risk are known in the art. One point is assigned for each of the following risk factors: (1) age greater than 60 years; (2) stage III or IV disease; (3) elevated serum LDH; (4) ECOG/Zubrod performance status of 2 (Symptomatic, <50% in bed during the day), 3 (Symptomatic, >50% in bed, but not bedbound), or 4 (Bedbound); and (5) more than 1 extranodal site. The IPI score is determined by summing the total number of points. While the IPI has been a useful clinical tool for lymphoma patient risk stratification, it was developed prior to the use of monoclonal antibody therapy in DLBCL patients. For example, rituximab together with combination chemotherapy has dramatically improved the outcomes of DLBCL patients, and thus new methods for patient risk stratification are necessary.

An "isolated antibody," as used herein, is intended to refer to an antibody that is substantially free of other antibodies having different antigenic specificities. Moreover, an isolated antibody may be substantially free of other cellular material and/or chemicals.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations, in which compositions of the invention are separated from cellular components of the cells from which they are isolated or recombinantly produced. In one embodiment, the language "substantially free of cellular material" includes preparations of having less than about 30%, 20%, 10%, or 5% (by dry weight) of cellular material. When an antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe, for specifically detecting or modulating the expression of a marker of the invention. The kit may be promoted, distributed, or sold as a unit for performing the methods of the present invention.

The term "lymphoma" refers to cancers that originate in the lymphatic system. Lymphoma is characterized by malignant neoplasms of lymphocytes—B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body. Lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

A "marker" or "biomarker" includes a nucleic acid or polypeptide whose altered level of expression in a tissue or cell from its expression level in a control (e.g., normal or healthy tissue or cell) is associated with a disease state, such as a cancer or subtype thereof (e.g., a hematological cancer, such as DLBCL). A "marker nucleic acid" is a nucleic acid (e.g., mRNA, cDNA, mature miRNA, pre-miRNA, pri-miRNA, miRNA*, anti-miRNA, or a miRNA binding site, or a variant thereof) and other classes of small RNAs known to a skilled artisan) encoded by or corresponding to a marker of the invention. Such marker nucleic acids include DNA (e.g., cDNA) comprising the entire or a partial sequence of any of the nucleic acid sequences set forth in Tables 1-9 or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" includes a protein encoded by or corresponding to a marker of the invention. A marker protein comprises the entire or a partial sequence of any of the sequences set forth in Tables 1-9. The terms "protein" and "polypeptide" are used interchangeably. In some embodiments, specific combinations of biomarkers are preferred. For example, a combination of one or more of the biomarkers selected from the group consisting of modulation (e.g., gain or loss) of copy number, level of expression, and/or level of activity of human chromosome 9p21.3 and/or CDKN2A; human chromosome 7q22.1 and/or CDK6; human chromosome 17p13.1 and/or TP53 and/or KDM6B and/or RPL26; human chromosome 16q12.2 and/or RBL2; human chromosome 19q13.42 and/or BCL2L12; human chromosome 13q14.2 and/or RB1; human chromosome 12q15 and/or CDK2 and/or CDK4 and/or MDM2; human chromosome 1q23.3 and/or MDM4 and/or RFWD2; and human chromosome 6p21.32 and/or CCND3. In another embodiment, a combination of one or more of the biomarkers selected from the group consisting of loss of copy number, level of expression, and/or level of activity of human chromosome 17p13.1 and/or KDM6B and/or RPL26; loss of copy number, level of expression, and/or level of activity of human chromosome 16q12.2 and/or RBL2; gain of copy number, level of expression, and/or level of activity of human chromosome 19q13.42 and/or BCL2L12; and gain of copy number, level of expression, and/or level of activity of human chromosome 1q23.3 and/or MDM4 and/or RFWD2; and human chromosome 6p21.32 and/or CCND3.

As used herein, the term "modulate" includes up-regulation and down-regulation, e.g., enhancing or inhibiting a response.

The "normal" level of expression of a marker is the level of expression of the marker in cells of a subject, e.g., a human patient, not afflicted with a cancer. An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The term "peripheral blood cell subtypes" refers to cell types normally found in the peripheral blood including, but is not limited to, eosinophils, neutrophils, T cells, monocytes, NK cells, granulocytes, and B cells.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., hematological cancers, such as DLBCL), development of one or more clinical factors, development of intestinal cancer, or recovery from the disease.

The term "R-CHOP" as used herein refers generally to any therapeutic regimen that includes chemotherapy and the administration of Rituximab. Accordingly, while the term can refer to a Rituximab combination therapy that includes a CHOP regimen of cyclophosphamide, doxorubicine, vincristine, and prednisone, the term R-CHOP can also refer to therapy that includes Rituximab in combination with a chemotherapeutic regimen other than CHOP.

The term "response to cancer therapy" or "outcome of cancer therapy" relates to any response of the hyperproliferative disorder (e.g., cancer) to a cancer therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Response may also be assessed by caliper measurement or pathological examination of the tumor after biopsy or surgical resection for solid cancers. Responses may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to copy number, level of expression, level of activity, etc. of one or more biomarkers listed in Tables 1-9 that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom the measurement values are known. In certain embodiments, the same doses of cancer therapeutic agents are administered to each subject. In related embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker threshold values that correlate to outcome of a cancer therapy can be determined using methods such as those described in the Examples section. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%. Thus, the present invention further provides methods for making a treatment decision for a cancer patient, comprising carrying out the methods for prognosing a cancer patient according to the different aspects and embodiments of the present invention, and then weighing the results in light of other known clinical and pathological risk factors, in determining a course of treatment for the cancer patient. For example, a cancer patient that is shown by the methods of the invention to have an increased risk of poor outcome by combination chemotherapy treatment can be treated with more aggressive therapies, including but not limited to radiation therapy, peripheral blood stem cell transplant, bone marrow transplant, or novel or experimental therapies under clinical investigation.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., chemotherapeutic or radiation therapy. In some embodiments, normal cells are not affected to an extent that causes the normal cells to be unduly injured by the cancer therapy (e.g., chemotherapy or radiation therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhome, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anticancer agents or chemotherapy drugs can be greater than the sum of the separate effects of the anticancer agents or chemotherapy drugs alone.

The term "subject" refers to any healthy animal, mammal or human, or any animal, mammal or human afflicted with a condition of interest (e.g., cancer). The term "subject" is interchangeable with "patient."

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcript" is a polynucleotide (e.g. an mRNA, hnRNA, cDNA, mature miRNA, pre-miRNA, pri-miRNA, miRNA*, anti-miRNA, or a miRNA binding site, or a variant thereof or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors." In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

An "underexpression" or "significantly lower level of expression or copy number" of a marker refers to an expression level or copy number in a test sample that is greater than the standard error of the assay employed to assess expression or copy number, but is preferably at least twice, and more preferably three, four, five or ten or more times less than the expression level or copy number of the marker in a control sample (e.g., sample from a healthy subject not afflicted with cancer) and preferably, the average expression level or copy number of the marker in several control samples.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Tables 1-9) are well known in the art and readily available on publicly available databases, such as the National Center for Biotechnology Information (NCBI). For example, exemplary nucleic acid and amino acid sequences derived from publicly available sequence databases are provided below.

The nucleic acid and amino acid sequences of a representative human KDM6B biomarker is available to the public at the GenBank database under NM_001080424.1 and NP_001073893.1. Nucleic acid and polypeptide sequences of KDM6B orthologs in organisms other than humans are well known and include, for example, dog KDM6B (XM_546599.3 and XP_546599.2), mouse KDM6B (NM_001017426.1 and NP_001017426.1), rat KDM6B (NM_001108829.1 and NP_001102299.1), and zebrafish KDM6B (XM_003198938.1 and XP_003198986.1 and NM_001030178.1 and NP_001025349.1).

The nucleic acid and amino acid sequences of a representative human RPL26 biomarker is available to the public at the GenBank database under NM_000987.3 and NP_000978.1. Nucleic acid and polypeptide sequences of RPL26 orthologs in organisms other than humans are well known and include, for example, chimpanzee RPL26 (XM_003315597.1 and XP_003315645.1 and XM_003339296.1 and XP_003339344.1 and XM_001166961.2 and XP_001166961.1 and XM_003315598.1 and XP_003315646.1), cow RPL26 (NM_001015512.2 and NP_001015512.1), mouse RPL26 (NM_009080.2 and NP_033106.1), rat RPL26 (NM_001105788.1 and NP_001099258.1), zebrafish RPL26 (NM_213113.2 and NP_998278.1), and fruit fly RPL26 (NM_140813.2 and NP_649070.1).

The nucleic acid and amino acid sequences of a representative human RBL2 biomarker is available to the public at the GenBank database under NM_005611.3 and NP_005602.3. Nucleic acid and polypeptide sequences of RBL2 orthologs in organisms other than humans are well known and include, for example, chimpanzee RBL2 (XM_001166080.2 and XP_001166080.2 and XM_523371.3 and XP_523371.2), dog RBL2 (XM_535303.3 and XP_535303.2), cow RBL2 (NM_001098073.1 and NP_001091542.1), mouse RBL2 (NM_011250.3 and NP_035380.3), rat RBL2 (NM_031094.1 and NP_112356.1), and zebrafish RBL2 (XM_002666954.2 and XP_002667000.2).

At least two splice variants encoding two human BCL2L12 isoforms exist. The sequence of human BCL2L12 transcript variant 1, which encodes the longer of the human BCL2L12 isoforms (i.e., isoform a), is available to the public at the GenBank database under NM_138639.1 and NP_619580.1. The sequence of human BCL2L12 transcript variant 2 uses an alternate in-frame splice site at the 5' end of an exon, which results in a slightly shorter protein than isoform a while having the same N- and C-termini. These sequences can be found under NM_001040668.1 and NP_001035758.1. Nucleic acid and polypeptide sequences of BCL2L12 orthologs in organisms other than humans are well known and include, for example, chimpanzee BCL2L12 (XM_512827.3 and XP_512827.2), cow BCL2L12 (NM_001101148.1 and NP_001094618.1), and mouse BCL2L12 (NM_029410.3 and NP_083686.1).

At least three splice variants encoding three human MDM4 isoforms exist. The sequence of human MDM4 transcript variant 1, which encodes the longest of the human MDM4 isoforms (i.e., isoform a), is available to the public at the GenBank database under NM_002393.4 and NP_002384.2. The sequence of human MDM4 transcript variant 2 lacks an in-frame coding exon compared to transcript variant 1, which results in a shorter isoform (i.e., isoform b) that is missing an internal protein segment in the 3' coding region relative to isoform a. These sequences can be found under NM_001204171.1 and NP_001191100.1. The sequence of human MDM4 transcript variant 3 is missing 8 consecutive coding exons and uses an alternate acceptor splice site at the 3' terminal exon compared to transcript variant 1. Transcript variant 3 encodes a very short isoform (i.e., isoform c) that lacks the N-terminal p53 binding domain, retains the RING finger domain at the C-terminus, binds and stabilizes oncoprotein HDM2, and also indirectly stabilizes p53 protein by counteracting its degradation by HDM2. These sequences can be found under NM_001204172.1 and NP_001191101.1. Nucleic acid and polypeptide sequences of MDM4 orthologs in organisms other than humans are well known and include, for example, chimpanzee MDM4 (XM_001160152.2 and XP_001160152.1 and XM_001160110.2 and XP_001160110.1 and XM_003308706.1 and XP_003308754.1), dog MDM4 (XM_536098.3 and XP_536098.3 and XM_003434324.1 and XP_003434372.1 and XM_003434325.1 and XP_003434373.1), cow MDM4 (NM_001046169.1 and NP_001039634.1), mouse MDM4 (NM_008575.3 and NP_032601.2), rat MDM4 (NM_001012026.1 and NP_001012026.1), chicken MDM4 (XM_417957.3 and XP_417957.3), and zebrafish MDM4 (NM_212732.1 and NP_997897.1).

At least two variants encoding two human RFWD2 isoforms exist. The sequence of human RFWD2 transcript variant 1, which encodes isoform a, is available to the public at the GenBank database under NM_022457.5 and NP_071902.2. The sequence of human RFWD2 transcript variant 2, which encodes isoform d24, is available to the public at the GenBank database under NM_001001740.2 and NP_001001740.1. Nucleic acid and polypeptide sequences of RFWD2 orthologs in organisms other than humans are well known and include, for example, mouse RFWD2 (NM_011931.3 and NP_036061.1), zebrafish RFWD2 (NM_001089542.1 and NP_001083011.1), cow RFWD2 (NM_001103256.1 and NP_001096726.1), chicken RFWD2 (XM_426628.3 and XP_426628.3), dog RFWD2 (XM_537181.3 and XP_537181.2), and chimpanzee RFWD2 (XM_001153038.2 and XP_001153038.2 and XM_514018.2 and XP_514018.2).

```
Human KDM6B cDNA Sequence
                                                       SEQ ID NO: 1
      1   atgcatcggg cagtggaccc tccaggggcc cgcgctgcac gggaagcctt tgcccttggg 61   ggcctgagct gtgctggggc ctggagctcc tgcccgcctc atccccctcc tcgtagcgca 121   tggctgcctg gaggcagatg ctcagccagc attgggcagc cccgcttcc  tgctccccta 181   cccccttcac atgcagtag  ttctgggcac cccagcaaac catattatgc tccaggggcg 241   cccactccaa gacccctcca tgggaagctg gaatccctgc atggctgtgt gcaggcattg 301   ctccgggagc cagcccagcc agggctttgg gaacagcttg ggcaactgta cgagtcagag
```

-continued

```
 361  cacgatagtg aggaggccac acgctgctac cacagcgccc ttcgatacgg aggaagcttc
 421  gctgagctgg gccccgcat tggccgactg cagcaggccc agctctggaa ctttcatact
 481  ggctcctgcc agcaccgagc caaggtcctg cccccactgg agcaagtgtg aacttgcta
 541  caccttgagc acaaacggaa ctatggagcc aagcggggag gtccccgggt gaagcgagct
 601  gctgaacccc cagtggtgca gcctgtgcct cctgcagcac tctcaggccc ctcaggggag
 661  gagggcctca gccctggagg caagcgaagg agaggctgca actctgaaca gactggcctt
 721  cccccagggc tgccactgcc tccaccacca ttaccaccac caccaccacc accaccacca
 781  ccaccaccac ccctgcctgg cctggctacc agccccccat ttcagctaac caagccaggg
 841  ctgtggagta ccctgcatgg agatgcctgg ggcccagagc gcaagggttc agcaccccca
 901  gagcgccagg agcagcggca ctcgctgcct cacccatatc catacccagc tccagcgtac
 961  accgcgcacc ccctggcca ccggctggtc ccggctgctc cccaggccc aggccccgc
1021  cccccaggag cagagagcca tggctgcctg cctgccaccc gtccccccgg aagtgacctt
1081  agagagagca gagttcagag gtcgcggatg gactccagcg tttcaccagc agcaaccacc
1141  gcctgcgtgc cttacgcccc ttcccgcccc cctggcctcc ccggcaccac caccagcagc
1201  agcagtagca gcagcagcaa cactggtctc cggggcgtgg agccgaaccc aggcattccc
1261  ggcgctgacc attaccaaac tcccgcgctg gaggtctctc accatggccg cctggggccc
1321  tcggcacaca gcagtcggaa accgttcttg ggggctcccg ctgccactcc ccacctatcc
1381  ctgccacctg gaccttcctc accccctcca cccccctgtc cccgcctctt acgcccccca
1441  ccacccctg cctggttgaa gggtccggcc tgccgggcag cccgagagga tggagagatc
1501  ttagaagagc tcttctttgg gactgaggga ccccccgcc ctgccccacc cccctcccc
1561  catcgcgagg gcttcttggg gcctccggcc tcccgctttt ctgtgggcac tcaggattct
1621  cacacccctc ccactccccc aaccccaacc accagcagta gcaacagcaa cagtggcagc
1681  cacagcagca gccctgctgg gcctgtgtcc tttcccccac caccctatct ggccagaagt
1741  atagaccccc ttcccccggcc tcccagccca gcacagaacc cccaggaccc acctcttgta
1801  cccctgactc ttgccctgcc tccagccccct ccttcctcct gccaccaaaa tacctcagga
1861  agcttcaggc gcccggagag ccccgggccc agggtctcct tcccaaagac ccccgaggtg
1921  gggccgggc cacccccagg cccccctgagt aaagcccccc agcctgtgcc gcccggggtt
1981  ggggagctgc ctgcccgagg ccctcgactc tttgattttc ccccactcc gctggaggac
2041  cagtttgagg agccagccga attcaagatc ctacctgatg ggctggccaa catcatgaag
2101  atgctggacg aatccattcg caaggaagag gaacagcaac aacacgaagc aggcgtggcc
2161  ccccaacccc cgctgaagga gccttttgca tctctgcagt ctcctttccc caccgacaca
2221  gccccccacca ctactgctcc tgctgtcgcc gtcaccacca ccaccaccac caccaccacc
2281  accacggcca cccaggaaga ggagaagaag ccaccaccag ccctaccacc accaccgcct
2341  ctagccaagt tccctccacc ctctcagcca cagccaccac caccccacc ccccagcccg
2401  gccagcctgc tcaaatcctt ggcctccgtg ctggagggac aaaagtactg ttatcggggg
2461  actggagcag ctgtttccac ccggcctggg cccttgccca ccactcagta ttcccctggc
2521  ccccccatcag gtgctaccgc cctgccgccc acctcagcgg ccctagcgc cagggctcc
2581  ccacagccct gcttcctc gtcatctcag ttctctacct caggcgggcc ctgggcccgg
2641  gagcgcaggg cgggcgaaga gccagtcccg ggcccatga ccccaccca accgccccca
2701  cccctatctc tgcccctgc tcgctctgag tctgaggtgc tagaagagat cagccgggct
```

```
-continued
2761  tgcgagaccc ttgtggagcg ggtgggccgg agtgccactg acccagccga cccagtggac
2821  acagcagagc cagcggacag tgggactgag cgactgctgc ccccgcaca ggccaaggag
2881  gaggctggcg gggtggcggc agtgtcaggc agctgtaagc ggcgacagaa ggagcatcag
2941  aaggagcatc ggcggcacag gcgggcctgt aaggacagtg tgggtcgtcg gccccgtgag
3001  ggcagggcaa aggccaaggc caaggtcccc aaagaaaaga gccgccgggt gctggggaac
3061  ctggacctgc agagcgagga gatccagggt cgtgagaagt cccggcccga tcttggcggg
3121  gcctccaagg ccaagccacc cacagctcca gcccctccat cagctcctgc accttctgcc
3181  cagcccacac ccccgtcagc ctctgtccct ggaaagaagg ctcgggagga agccccaggg
3241  ccaccgggtg tcagccgggc cgacatgctg aagctgcgct cacttagtga ggggcccccc
3301  aaggagctga agatccggct catcaaggta gagagtggtg acaaggagac ctttatcgcc
3361  tctgaggtgg aagagcggcg gctgcgcatg gcagacctca ccatcagcca ctgtgctgct
3421  gacgtcgtgc gcgccagcag gaatgccaag gtgaaaggga agtttcgaga gtcctacctt
3481  tcccctgccc agtctgtgaa accgaagatc aacactgagg agaagctgcc ccgggaaaaa
3541  ctcaacccccc ctacacccag catctatctg gagagcaaac gggatgcctt ctcacctgtc
3601  ctgctgcagt tctgtacaga ccctcgaaat cccatcacag tgatccgggg cctggcgggc
3661  tccctgcggc tcaacttggg cctcttctcc accaagaccc tggtggaagc gagtggcgaa
3721  cacaccgtgga agttcgcac ccaggtgcag cagccctcag atgagaactg ggatctgaca
3781  ggcactcggc agatctggcc ttgtgagagc tcccgttccc acaccaccat gccaagtac
3841  gcacagtacc aggcctcatc cttccaggag tctctgcagg aggagaagga gagtgaggat
3901  gaggagtcag aggagccaga cagcaccact ggaaccccctc ctagcagcgc accagacccg
3961  aagaaccatc acatcatcaa gtttggcacc aacatcgact tgtctgatgc taagcggtgg
4021  aagccccagc tgcaggagct gctgaagctg cccgccttca tgcgggtaac atccacgggc
4081  aacatgctga ccacgtggg ccacaccatc ctgggcatga acacggtgca gctgtacatg
4141  aaggtgcccg gcagccgaac gccaggccac caggagaata caacttctg ctccgtcaac
4201  atcaacattg gcccaggcga ctgcgagtgg ttcgcggtgc acgagcacta ctgggagacc
4261  atcagcgctt tctgtgatcg gcacggcgtg gactacttga cgggttcctg gtggccaatc
4321  ctggatgatc tctatgcatc caatattcct gtgtaccgct tcgtgcagcg acccggagac
4381  ctcgtgtgga ttaatgcggg gactgtgcac tgggtgcagg ccaccggctg gtgcaacaac
4441  attgcctgga acgtggggcc cctcaccgcc tatcagtacc agctggccct ggaacgatac
4501  gagtggaatg aggtgaagaa cgtcaaatcc atcgtgccca tgattcacgt gtcatggaac
4561  gtggctcgca cggtcaaaat cagcgacccc gacttgttca agatgatcaa gttctgcctg
4621  ctgcagtcca tgaagcactg ccaggtgcaa cgcgagagcc tggtgcgggc agggaagaaa
4681  atcgcttacc agggccgtgt caaggacgag ccagcctact actgcaacga gtgcgatgtg
4741  gaggtgttta acatcctgtt cgtgacaagt gagaatggca gccgcaacac gtacctggta
4801  cactgcgagg gctgtgcccg gcgccgcagc gcaggcctgc agggcgtggt ggtgctggag
4861  cagtaccgca ctgaggagct ggctcaggcc tacgacgcct tcacgctggt gagggcccgg
4921  cggcgcgcg ggcagcggag gagggcactg gggcaggctg cagggacggg cttcgggagc
4981  ccggccgcgc ctttccctga gcccccgccg gctttctccc cccaggcccc agccagcacg
5041  tcgcgatga
```

-continued

Human KDM6B Amino Acid Sequence

SEQ ID NO: 2

```
   1  mhravdppga raareafalg glscagawss cpphpppssa wlpggrcsas igqpplpapl
  61  ppshgsssgh pskpyyapga ptprplhgkl eslhgcvgal lrepaqpglw eqlgqlyese
 121  hdseeatrcy hsalryggsf aelgprigrl qqaqlwnfht gscqhrakvl ppleqvwnll
 181  hlehkrnyga krggppvkra aeppvvqpvp paalsgpsge eglspggkrr rgcnseqtgl
 241  ppglplpppp lpppppppp pppplpglat sppfqltkpg lwstlhgdaw gperkgsapp
 301  erqeqrhslp hpypypapay tahppghrlv paappgpgpr ppgaeshgcl patrppgsdl
 361  resrvqrsrm dssyspaatt acvpyapsrp pglpgtttss ssssssntgl rgvepnpgip
 421  gadhyqtpal evshhgrlgp sahssrkpfl gapaatphls lppgpssppp ppcprllrpp
 481  pppawlkgpa craaredgei leelffgteg pprpappplp hregflgppa srfsvgtqds
 541  htpptpptpt tsssnsnsgs hssspagpvs fppppylars idplprppsp agnpcidpplv
 601  pltlalppap psschqntsg sfrrpesprp rvsfpktpev gpgpppgpls kapqpvppgv
 661  gelpargprl fdfpptpled qfeepaefki lpdglanimk mldesirkee eqqheagva
 721  pqpplkepfa slqspfptdt apttaapava vttttttttt ttatqeeekk pppalppppp
 781  lakfpppsqp qppppppsp asllkslasv legqkycyrg tgaaystrpg plpttqyspg
 841  ppsgatalpp tsaapsaqgs pqpsassssq fstsggpwar errageepvp gpmtptqppp
 901  plslpparse sevleeisra cetivervgr satdpadpvd taepadsgte rllppaqake
 961  eaggvaaysg sckrrqkehq kehrrhrrac kdsvgrrpre grakakakvp keksrrvlgn
1021  ldlqseeiqg reksrpdlgg askakpptap appsapapsa qptppsasvp gkkareeapg
1081  ppgvsradml klrslsegpp kelkirlikv esgdketfia seveerrlrm adltishcaa
1141  dvvrasrnak vkgkfresyl spaqsvkpki nteeklprek lnpptpsiyl eskrdafspv
1201  llqfctdprn pitvirglag slrinlglfs tktiveasge htvevrtqvq qpsdenwdlt
1261  gtrqiwpces srshttiaky aqyqassfqe slqeekesed eeseepdstt gtppssapdp
1321  knhhiikfgt nidlsdakrw kpqlqellkl pafmrvtstg nmlshvghti lgmntvglym
1381  kvpgsrtpgh qennnfcsvn inigpgdcew favhehywet isafcdrhgv dyltgswwpi
1441  iddlyasnip vyrfvqrpgd lvwinagtvh wvqatgwcnn iawnvgplta yqyglalery
1501  ewnevknvks ivpmihvswn vartvkisdp dlfkmikfcl lqsmkhcqvq reslvragkk
1561  iayqgrvkde payycnecdv evfnilfvts engsrntylv hcegcarrrs aglqgvvvle
1621  qyrteelaqa ydaftivrar rargqrrral gqaagtgfgs paapfpeppp afspqapast
1681  sr
```

Human RPL26 cDNA Sequence

SEQ ID NO: 3

```
   1  atgaagttta atcccttgt gacttccgac cgaagcaaga atcgcaaaag gcatttcaat
  61  gcaccttccc acattcgaag gaagattatg tcttccctc tttccaaaga gctgagacag
 121  aagtacaacg tgcgatccat gcccatccga aaggatgatg aagttcaggt tgtacgtgga
 181  cactataaag gtcagcaaat tggcaaagta gtccaggttt acaggaagaa atatgttatc
 241  tacattgaac gggtgcagcg ggaaaaggct aatggcacaa ctgtccacgt aggcattcac
 301  cccagcaagg tggttatcac taggctaaaa ctggacaaag accgcaaaaa gatcctcgaa
 361  cggaaagcca aatctcgcca agtaggaaag gaaagggca aatacaagga agaaaccatt
 421  gagaagatgc aggaataa
```

Human RPL26 Amino Acid Sequence

SEQ ID NO: 4

```
  1 mkfnpfvtsd rsknrkrhfn apshirrkim ssplskelrq kynvrsmpir kddevqvvrg
 61 hykgqqigkv vqvyrkkyvi yiervqreka ngttvhvgih pskvvitrlk ldkdrkkile
121 rkaksrqvgk ekgkykeeti ekmqe
```

Human RBL2 cDNA Sequence

SEQ ID NO: 5

```
   1 atgccgtcgg gaggtgacca gtcgccaccg ccccgcctc ccctccggc ggcggcagcc
  61 tcggatgagg aggaggagga cgacggcgag gcggaagacg ccgcgccgcc tgccgagtcg
 121 cccaccctc agatccagca gcggttcgac gagctgtgca gccgcctcaa catggacgag
 181 gcggcgcggg ccgaggcctg ggacagctac cgcagcatga gcgaaagcta cacgctggag
 241 ggaaatgatc ttcattggtt agcatgtgcc ttatatgtgg cttgcagaaa atctgttcca
 301 actgtaagca aagggacagt ggaaggaaac tatgtatctt aactagaat cctgaaatgt
 361 tcagagcaga gcttaatcga attttttaat aagatgaaga gtgggaaga catggcaaat
 421 ctaccccac atttcagaga acgtactgag agattagaaa gaaacttcac tgtttctgct
 481 gtaatttta agaaatatga acccattttt caggacatct ttaaatacc tcaagaggag
 541 caacctcgtc agcagcgagg aaggaaacag cggcgacagc cctgtactgt gtctgaaatt
 601 ttccatttt gttgggtgct ttttatatat gcaaaaggta atttccccat gattagtgat
 661 gatttggtca attcttatca cctgctgctg tgtgctttgg acttagttta tggaaatgca
 721 cttcagtgtt ctaatcgtaa agaacttgtg aaccctaatt ttaaaggctt atctgaagat
 781 tttcatgcta aagattctaa accttcctct gaccccctt gtatcattga gaaactgtgt
 841 tccttacatg atggcctagt tttggaagca aagggggataa aggaacattt ctggaaaccc
 901 tatattagga aactttatga aaaaaagctc cttaagggaa aagaagaaaa tctcactggg
 961 tttctagaac ctgggaactt tggagagagt tttaaagcca tcaataaggc ctatgaggag
1021 tatgttttat ctgttgggaa tttagatgag cggatatttc ttggagdgga tgctgaggag
1081 gaaattggga ctctctcaag gtgtctgaac gctggttcag gaacagagac tgctgaaagg
1141 gtgcagatga aaacatctt acagcagcat tttgacaagt ccaaagcact tagaatctcc
1201 acaccactaa ctggtgttag gtacattaag gagaatagcc cttgtgtgac tccagtttct
1261 acagctacgc atagcttgag tcgtcttcac accatgctga caggcctcag gaatgcacca
1321 agtgagaaac tggaacagat tctcaggaca tgttccagag atccaaccca ggctattgct
1381 aacagactga agaaatgtt tgaaatatat tctcagcatt ccagccaga cgaggatttc
1441 agtaattgtg ctaaagaaat tgccagcaaa cattttcgtt ttgcggagat gctttactat
1501 aaagtattag aatctgttat tgagcaggaa caaaaaagac taggagacat ggatttatct
1561 ggtattctgg aacaagatgc gttccacaga tctctcttgg cctgctgcct tgaggtcgtc
1621 actttttctt ataagcctcc tgggaatttt ccattttatta ctgaaatatt tgatgtgcct
1681 ctttatcatt tttataaggt gatagaagta ttcattagag cagaagatgg cctttgtaga
1741 gaggtggtaa aacaccttaa tcagattgaa aacagatct tagatcattt ggcatggaaa
1801 ccagagtctc cactctggga aaaaattaga acaatgaaaa acagagttcc tacatgtgaa
1861 gaggtcatgc cacctcagaa cctggaaagg gcagatgaaa tttgcattgc tggctcccct
1921 ttgactccca gaagggtgac tgaagttcgt gctgatactg gaggacttgg aaggagcata
1981 acatctccaa ccacattata cgataggtac agctccccac cagcagcac taccagaagg
2041 cggctatttg ttgagaatga tagccccctct gatggaggga cgcctgggcg catgccccca
```

-continued

```
2101  cagcccctag tcaatgctgt ccctgtgcag aatgtatctg gggagactgt ttctgtcaca 2161  ccagttcctg acagactttg gtcaccatg gcaaccgcca ctgtcacagc caacaatggg 2221  caaacggtaa ccattcctgt gcaaggtatt gccaatgaaa atggagggat aacattcttc 2281  cctgtccaag tcaatgttgg ggggcaggca caagctgtga caggctccat ccagcccctc 2341  agtgctcagg ccctggctgg aagtctgagc tctcaacagg tgacaggaac aactttgcaa 2401  gtccctggtd aagtggccat tcaacagatt tccccaggtg ccaacagca gaagcaaggc 2461  cagtctgtaa ccagcagtag taatagaccc aggaagacca gctctttatc gcttttcttt 2521  agaaaggtat accatttagc agctgtccgc cttcgggatc tctgtgccaa actagatatt 2581  tcagatgaat tgaggaaaaa aatctggacc tgctttgaat ctccataat tcagtgtcct 2641  gaacttatga tggacagaca tctggaccag ttattaatgt gtgccattta tgtgatggca 2701  aaggtcacaa agaagataa gtccttccag aacattatgc gttgttatag gactcagccg 2761  caggcccgga gccaggtgta tagaagtgtt ttgataaaag ggaaaagaaa aagaagaaat 2821  tctggcagca gtgatagcag aagccatcag aattctccaa cagaactaaa caaagataga 2881  accagtagag actccagtcc agttatgagg tcaagcagca ccttgccagt tccacagccc 2941  agcagtgctc ctcccacacc tactcgcctc acaggtgcca acagtgacat ggaagaagag 3001  gagaggggag acctcattca gttctacaac aacatctaca tcaaacagat taagacattt 3061  gccatgaagt actcacaggc aaatatggat gctcctccac tctctcccta tccatttgta 3121  agaacaggct cccctcgccg aatacagttg tctcaaaatc atcctgtcta catttcccca 3181  cataaaaatg aaacaatgct ttctcctcga gaaagatttt tctattactt cagcaacagt 3241  ccttcaaaga gactgagaga aattaatagt atgatacgca caggagaaac tcctactaaa 3301  aagagaggaa ttcttttgga agatggaagt gaatcacctg caaaaagaat ttgcccagaa 3361  aatcattctg ccttattacg ccgtctccaa gatgtagcta atgaccgtgg ttcccactga
```

Human RBL2 Amino Acid Sequence

SEQ ID NO: 6

```
  1  mpsggdqspp pppppaaaa sdeeeeddge aedaappaes ptpqiqqrfd elcsrinmde 61  aaraeawdsy rsmsesytle gndlhwlaca lyvacrksvp tvskgtvegn yvsltrilkc 121  seqslieffn kmkkwedman lpphfrerte rlernftvsa vifkkyepif qdifkypqee 181  qprqqrgrkq rrqpctvsei fhfcwvlfiy akgnfpmisd dlvnsyhlll caldlvygna 241  lqcsnrkelv npnfkglsed fhakdskpss dppciieklc slhdglvlea kgikehfwkp 301  yirklyekkl lkgkeenitg flepgnfges fkainkayee yvlsvgnlde riflgedaee 361  eigtlsrcln agsgtetaer vqmknilqqh fdkskalris tpltgvryik enspcvtpvs 421  tathslsrlh tmltglrnap sekleqilrt csrdptqaia nrlkemfeiy sqhfqpdedf 481  sncakeiask hfrfaemlyy kvlesvieqe qkrlgdmdls gileqdafhr sllacclevv 541  tfsykppgnf pfiteifdvp lyhfykviev firaedglcr evvkhlnqie eqildhlawk 601  pesplwekir dnenrvptce evmppqnler adeiciagsp ltprrvtevr adtgglgrsi 661  tspttlydry ssppasttrr rlfvendsps dggtpgrmpp qplvnavpvq nvsgetvsvt 721  pvpgqtivtm atatvtanng qtvtipvqgi anenggitff pvqvnvggqa qavtgsiqpl 781  sagalagsls sqqvtgttlq vpgqvaiqqi spggqqkqg qsvtsssnrp rktsslslff 841  rkvyhlaavr lrdlcakldi sdelrkkiwt cfefsiiqcp elmmdrhldq llmcaiyvma 901  kvtkedksfq nimrcyrtqp qarsqvyrsv likgkrkrrn sgssdsrshq nsptelnkdr 961  tsrdsspvmr ssstlpvpqp ssapptptrl tgansdmeee ergdliqfyn niyikqiktf
```

-continued

```
1021  amkysqanmd applspypfv rtgsprriql sqnhpvyisp hknetmlspr ekifyyfsns
1081  pskrlreins mirtgetptk krgilledgs espakricpe nhsallrrlq dvandrgsh
```

Human BCL2L12 (isoform a) cDNA Sequence

SEQ ID NO: 7
```
   1  atgggacggc ccgctgggct gttcccgccc ctatgccctt ttttgggttt ccggccagag
  61  gcatgctggg agcgtcacat gcaaattgag cgtgcaccca gcgttccgcc ctttctacgc
 121  tgggccggtt atcgacccgg cccagtgcgc aggcgcggga aagttgaact aataaagttt
 181  gtacgagttc agtggaggag accgcaagtt gagtggagga ggcggcggtg gggccccgga
 241  ccaggtgcct ccatggcagg ctctgaagag ctggggctcc gggaagacac gctgagggtc
 301  ctagctgcct tccttaggcg tggtgaggct gccgggtctc tgttccaac tccacctaga
 361  agccctgccc aagaagagcc aacagacttc ctgagccgcc ttcgaagatg tcttccctgc
 421  tccctggggc gaggagcagc ccctctgag tccctcggc cttgctctct gcccatccgc
 481  ccctgctatg gtttagagcc tggcccagct actccagact ctatgctttt ggtggcccag
 541  cggctggaac agctggtcca agagcagctg aaatctccgc ccagcccaga attacagggt
 601  cccccatcga cagagaagga agccatactg cggaggctgg tggcctgct gaggaggag
 661  gcagaagtca ttaaccagaa gctggcctcg gaccccgccc tgcgcagcaa gctggtccgc
 721  ctgtcctccg actctttcgc ccgcctggtg gagctgttct gtagcccgga tgacagctct
 781  cgcccaagcc gagcatgccc cgggccccg cctccttccc cggagcccct ggcccgcctg
 841  gccctagcca tggagctgag ccggcgcgtg gccgggctgg ggggcaccct ggccggactc
 901  agcgtggagc acgtgcacag cttcacgccc tggatccagg cccacggggg ctgggagggc
 961  atcctggctg tttcacccgt ggacttgaac ttgccattgg actga
```

Human BCL2L12 (isoform a) Amino Acid Sequence

SEQ ID NO: 8
```
   1  mgrpaglfpp lcpflgfrpe acwerhmqie rapsvpplr wagyrpgpvr rrgkvelikf
  61  vrvqwrrpqv ewrrrwgpg pgasmagsee lglredtlry laaflrrgea agspvptppr
 121  spaqeeptdf lsrlrrclpc slgrgaapse sprpcslpir pcyglepgpa tpdfyalvaq
 181  rleqlvqeql ksppspelqg ppstekeail rrlvalleee aevinqklas dpalrsklvr
 241  lssdsfarlv elfcsrddss rpsracpgpp ppspeplarl alamelsrry aglggtlagl
 301  svehvhsftp wiqahggweg ilayspvdln lpld
```

Human BCL2L12 (isoform b) cDNA Sequence

SEQ ID NO: 9
```
   1  atgggacggc ccgctgggct gttcccgccc ctatgccctt ttttgggttt ccggccagag
  61  gcatgctggg agcgtcacat gcaaattgag cgtgcaccca gcgttccgcc ctttctacgc
 121  tgggccggtt atcgacccgg cccagtgcgc aggcgcggga aagttgaact aataaagttt
 181  gtacgagttc agtggaggag accgcaagtt gagtggagga ggcggcggtg gggccccgga
 241  ccaggtgcct ccatggcagg ctctgaagag ctggggctcc gggaagacac gctgagggtc
 301  ctagctgcct tccttaggcg tggtgaggct gccgggtctc tgttccaac tccacctagc
 361  cctgcccaag aagagccaac agacttcctg agccgcctt gaagatgtct tccctgctcc
 421  ctggggcgag gagcagcccc tctgagtcc cctcggcctt gctctctgcc catccgcccc
 481  tgctatggtt tagagcctgg cccagctact ccagacttct atgctttggt ggcccagcgg
 541  ctggaacagc tggtccaaga gcagctgaaa tctccgccca gcccagaatt acagggtccc
 601  ccatcgacag agaaggaagc catactgcgg aggctggtgg ccctgctgga ggaggagca
 661  gaagtcatta accagaagct ggcctcggac cccgccctgc gcagcaagct ggtccgcctg
```

-continued

```
       721 tcctccgact ctttcgcccg cctggtggag ctgttctgta gccgggatga cagctctcgc
       781 ccaagccgag catgcccgg gcccccgcct ccttccccgg agccctggcc ccgcctggcc
       841 ctagccatgg agctgagccg gcgcgtggcc gggctggggg gcaccctggc cggactcagc
       901 gtggagcacg tgcacagctt cacgccctgg atccaggccc acggggctgg gagggcatc
       961 ctggctgttt cacccgtgga cttgaacttg ccattggact ga
```

Human BCL2L12 (isoform b) Amino Acid Sequence
```
                                                          SEQ ID NO: 10
         1 mgrpaglfpp lcpflgfrpe acwerhmqie rapsvppflr wagyrpgpvr rrgkvelikf
        61 vrvqwrrpqv ewrrrrwgpg pgasmagsee lglredtlry laaflrrgea agspvptpps
       121 pageeptdfl srlrrclpcs lgrgaapses prpcslpirp cyglepgpat pdfyalvaqr
       181 leqlvqeqlk sppspelqgp pstekeailr rlvalleeea evinqklasd palrsklvrl
       241 ssdsfarlve lfcsrddssr psracpgppp pspeplarla lamelsrrva glggtlagls
       301 vehvhsftpw iqahggwegi layspvdlnl pld
```

Human MDM4 (isoform a) cDNA Sequence
```
                                                          SEQ ID NO: 11
         1 atgacatcat tttccacctc tgctcagtgt caacatctg acagtgcttg caggatctct
        61 cctggacaaa tcaatcaggt acgaccaaaa ctgccgcttt tgaagatttt gcatgcagca
       121 ggtgcgcaag gtgaaatgtt cactgttaaa gaggtcatgc actatttagg tcagtacata
       181 atggtgaagc aactttatga tcagcaggag cagcatatgg tatattgtgg tggagatctt
       241 ttgggagaac tactgggacg tcagagcttc tccgtgaaag acccaagccc tctctatgat
       301 atgctaagaa agaatcttgt cactttagcc actgctacta cagatgctgc tcagactctc
       361 gctctcgcac aggatcacag tatggatatt ccaagtcaag accaactgaa gcaaagtgca
       421 gaggaaagtt ccacttccag aaaaagaact acagaagacg atatcccac actgcctacc
       481 tcagagcata aatgcataca ttctagagaa gatgaagact aattgaaaa tttagcccaa
       541 gatgaaacat ctaggctgga ccttggattt gaggagtggg atgtagctgg cctgccttgg
       601 tggttttag gaaacttgag aagcaactat acacctagaa gtaatggctc aactgattta
       661 cagacaaatc aggatgtggg tactgccatt gtttcagata ctacagatga cttgtggttt
       721 ttgaatgagt cagtatcaga gcagttaggt gttggaataa agttgaagc tgctgatact
       781 gaacaaacaa gtgaagaagt agggaaagta agtgacaaaa aggtgattga agtgggaaaa
       841 aatgatgacc tggaggactc taagtcctta agtgatgata ccgatgtaga ggttacctct
       901 gaggatgagt ggcagtgtac tgaatgcaag aaatttaact ctccaagcaa gaggtactgt
       961 tttcgttgtt gggccttgag gaaggattgg tattcagatt gttcaaagtt aacccattct
      1021 ctctccacgt ctgatatcac tgccataccct gaaaaggaaa atgaaggaaa tgatgtccct
      1081 gattgtcgaa gaaccatttc ggctcctgtc gttagaccta agatgcgta tataaagaaa
      1141 gaaaactcca acttttttga tccctgcaac tcagtggaat tcttggattt ggctcacagt
      1201 tctgaaagcc aagagaccat ctcaagcatg ggagaacagt tagataacct ttctgaacag
      1261 agaacagata cagaaaacat ggaggattgc cagaatctct tgaagccatg tagcttatgt
      1321 gagaaaagac cacgagacgg gaacattatt catggaagga cgggccatct tgtcacttgt
      1381 tttcactgtg ccagaagact aaagaaggct ggggcttcat gccctatttg caagaaagag
      1441 attcagctgg ttattaaggt ttttatagca taa
```

Human MDM4 (isoform a) Amino Acid Sequence
```
                                                          SEQ ID NO: 12
         1 mtsfstsaqc stsdsacris pgqinqvrpk lpllkilhaa gaqgemftvk evmhylgqyi
        61 mvkqlydqqe qhmvycggdl lgellgrqsf svkdpsplyd mlrknlvtla tattdaaqtl
```

-continued

```
121  alaqdhsmdi psqdqlkqsa eesstsrkrt teddiptlpt sehkcihsre dedlienlaq
181  detsrldlgf eewdvaglpw wflgnlrsny tprsngstdl qtnqdvgtai vsdttddlwf
241  lnesyseqlg vgikveaadt eqtseevgkv sdkkvievgk nddledsksl sddtdvevts
301  edewqcteck kfnspskryc frcwalrkdw ysdcsklths lstsditaip ekenegndvp
361  dcrrtisapv vrpkdayikk ensklfdpcn sveflddlahs sesqetissm geqldnlseq
421  rtdtenmedc qnllkpcslc ekrprdgnii hgrtghlvtc fhcarrlkka gascpickke
481  iqlvikvfia
```

Human MDM4 (isoform b) cDNA Sequence
SEQ ID NO: 13

```
   1  atgacatcat tttccacctc tgctcagtgt tcaacatctg acagtgcttg caggatctct
  61  cctggacaaa tcaatcaggt acgaccaaaa ctgccgcttt tgaagatttt gcatgcagca
 121  ggtgcgcaag gtgaaatgtt cactgttaaa gaggtcatgc actatttagg tcagtacata
 181  atggtgaagc aactttatga tcagcaggag cagcatatgg tatattgtgg tggagatctt
 241  ttgggagaac tactgggacg tcagagcttc tccgtgaaag acccaagccc tctctatgat
 301  atgctaagaa agaatcttgt cactttagcc actgctacta cagatgctgc tcagactctc
 361  gctctcgcac aggatcacag tatggatatt ccaagtcaag accaactgaa gcaaagtgca
 421  gaggaaagtt ccacttccag aaaaagaact acagaagacg atatccccac actgcctacc
 481  tcagagcata atgcataca ttctagagaa gatgaagact taattgaaaa tttagcccaa
 541  gatgaaacat ctaggctgga ccttggattt gaggagtggg atgtagctgg cctgccttgg
 601  tggtttttag gaaacttgag aagcaactat acacctagaa gtaatggctc aactgattta
 661  cagacaaatc aggtgattga agtgggaaaa aatgatgacc tggaggactc taagtcctta
 721  agtgatgata ccgatgtaga ggttacctct gaggatgagt ggcagtgtac tgaatgcaag
 781  aaatttaact ctccaagcaa gaggtactgt tttcgttgtt gggccttgag gaaggattgg
 841  tattcagatt gttcaaagtt aacccattct ctctccacgt ctgatatcac tgccataccc
 901  gaaaaggaaa atgaaggaaa tgatgtccct gattgtcgaa gaaccatttc ggctcctgtc
 961  gttagaccta agatgcgta tataaagaaa gaaaactcca actttttga tccctgcaac
1021  tcagtggaat tcttggattt ggctcacagt tctgaaagcc aagagaccat ctcaagcatg
1081  ggagaacagt tagataacct ttctgaacag agaacagata cagaaaacat ggaggattgc
1141  cagaatctct tgaagccatg tagcttatgt gagaaaagac cacgagacgg aacattatt
1201  catggaagga cgggccatct tgtcacttgt tttcactgtg ccagaagact aaagaaggct
1261  ggggcttcat gccctatttg caagaaagag attcagctgg ttattaaggt ttttatagca
1321  taa
```

Human MDM4 (isoform b) Amino Acid Sequence
SEQ ID NO: 14

```
   1  mtsfstsaqc stsdsacris pgqinqvrpk lpllkilhaa gaggemftvk evmhylgqyi
  61  mvkqlydqqe qhmvycggdl lgellgrqsf svkdpsplyd mlrknlvtla tattdaaqtl
 121  alaqdhsmdi psqdqlkqsa eesstsrkrt teddiptlpt sehkcihsre dedlienlaq
 181  detsrldlgf eewdvaglpw wflgnlrsny tprsngstdl qtnqvievgk nddledsksl
 241  sddtdvevts edewqcteck kfnspskryc frcwalrkdw ysdcsklths lstsditaip
 301  ekenegndvp dcrrtisapv vrpkdayikk ensklfdpcn sveflddlahs sesqetissm
 361  geqldnlseq rtdtenmedc qnllkpcslc ekrprdgnii hgrtghlvtc fhcarrlkka
 421  gascpickke iqlvikvfia
```

Human MDM4 (isoform c) cDNA Sequence

SEQ ID NO: 15

```
  1 atgacatcat tttccacctc tgctcagtgt tcaacatctg acagtgcttg caggatctct
 61 cctggacaaa tcaatcagga aaatgaagga atgatgtcc ctgattgtcg aagaaccatt
121 tcggctcctg tcgttagacc taaagatgcg tatataaaga agaaaactc caaactttt
181 gatccctgca actcagtgga attcttggat ttggctcaca gttctgaaag ccaagagacc
241 atctcaagca tgggagaaca gttagataac ctttctgaac agagaacaga tacagaaaac
301 atggaggatt gccagaatct cttgaagcca tgtagcttat gtgagaaaag accacgagac
361 gggaacatta ttcatggaag gacgggccat cttgtcactt gttttcactg tgccagaaga
421 ctaaagaagg ctggggcttc atgccctatt tgcaagaaag agattcagct ggttattaag
481 gttttatag cataa
```

Human MDM4 (isoform c) Amino Acid Sequence

SEQ ID NO: 16

```
  1 mtsfstsaqc stsdsacris pgqingeneg ndvpdcrrti sapvvrpkda yikkensklf
 61 dpcnsvefld lahssesqet issmgeqldn lseqrtdten medcqnllkp cslcekrprd
121 gniihgrtgh lvtcfhcarr lkkagascpi ckkeiqlvik vfia
```

Human RFWD2 (isoform a) cDNA Sequence

SEQ ID NO: 17

```
   1 atgtctggta gccgccaggc cgggtcgggc tccgctggga caagccccgg gtcctcggcg
  61 gcctcctcgg tgacttccgc ctcctcgtct ttatcctctt ccccgtcgcc gccttccgtg
 121 gcggtttcgg cggcagcgct ggtgtccggc ggggtggccc aggccgccgg ctcgggcggc
 181 ctcggggggcc cggtgcggcc tgtgttggtg gcgcccgccg tatcgggtag cggcggcggg
 241 gcggtgtcca cgggcctgtc ccggcacagc tgcgcggcca ggcccagcgc cggcgtagga
 301 ggcagcagct ccagcctagg cagcggcagc aggaagcgac ctctcctcgc ccccctctgc
 361 aacgggctca tcaactccta cgaggacaaa gcaacgact cgtatgccc catctgcttt
 421 gatatgattg aagaagcata catgacaaaa tgtggccaca gcttttgcta caagtgtatt
 481 catcagagtt tggaggacaa taatagatgt cccaagtgta actatgttgt ggacaatatt
 541 gaccatctgt atcctaattt cttggtgaat gaactcattc ttaaacagaa gcaaagattt
 601 gaggaaaaga ggttcaaatt ggaccactca gtgagtagca ccaatggcca caggtggcag
 661 atatttcaag attggttggg aactgaccaa gataaccttg atttggccaa tgtcaatctt
 721 atgttggagt tactagtgca gaagaagaaa caactggaag cagaatcaca tgcagcccaa
 781 ctacagattc ttatggaatt cctcaaggtt gcaagaagaa ataagagaga gcaactggaa
 841 cagatccaga aggagctaag tgttttggaa gaggatatta agagtggaa agaaatgagt
 901 ggcttatact ctcctgtcag tgaggatagc acagtgcctc aatttgaagc tccttctcca
 961 tcacacagta gtattattga ttccacagaa tacagccaac tccaggtttt cagtggcagt
1021 tctcagacaa agaaacagcc ttggtataat agcacgttag catcaagacg aaaacgactt
1081 actgctcatt tgaagacttg gagcagtgt tactttcta caaggatgtc tcgtatctca
1141 gatgacagtc gaactgcaag ccagttggat gaattcagg aatgcttgtc aagtttact
1201 cgatataatt cagtacgacc tttagccaca ttgtcatatg ctagtgatct ctataatggt
1261 tccagtatag tctctagtat tgaatttgac cgggattgtg actattttgc gattgctgga
1321 gttacaaaga agattaaagt ctatgaatat gacactgtca tccaggatgc agtggatatt
1381 cattaccctg agaatgaaat gacctgcaat tcgaaaatca gctgtatcag ttggagtagt
1441 taccataaga acctgttagc tagcagtgat tatgaaggca ctgttatttt atgggatgga
1501 ttcacaggac agaggtcaaa ggtctatcag gagcatgaga gaggtgttg gagtgttgac
```

```
1561  tttaatttga tggatcctaa actcttggct tcaggttctg atgatgcaaa agtgaagctg
1621  tggtctacca atctagacaa ctcagtggca agcattgagg caaaggctaa tgtgtgctgt
1681  gttaaattca gcccctcttc cagataccat ttggctttcg gctgtgcaga tcactgtgtc
1741  cactactatg atcttcgtaa cactaaacag ccaatcatgg tattcaaagg acaccgtaaa
1801  gcagtctctt atgcaaagtt tgtgagtggt gaggaaattg tctctgcctc aacagacagt
1861  cagctaaaac tgtggaatgt agggaaacca tactgcctac gttccttcaa gggtcatatc
1921  aatgaaaaaa actttgtagg cctggcttcc aatggagatt atatagcttg tggaagtgaa
1981  aataactctc tctacctgta ctataaagga ctttctaaga ctttgctaac ttttaagttt
2041  gatacagtca aaagtgttct cgacaaagac cgaaaagaag atgatacaaa tgaatttgtt
2101  agtgctgtgt gctggagggc actaccagat ggggagtcca atgtgctgat tgctgctaac
2161  agtcagggta caattaaggt gctagaattg gtatga
```

Human RFWD2 (isoform a) Amino Acid Sequence

SEQ ID NO: 18

```
  1  msgsrqagsg sagtspgssa assvtsasss lssspsppsv aysaaalvsg gvaqaagsgg
 61  lggpvrpvlv apaysgsggg aystglsrhs caarpsagvg gsssslgsgs rkrpllaplc
121  nglinsyedk sndfvcpicf dmieeaymtk cghsfcykci hqslednnrc pkcnyvvdni
181  dhlypnflvn elilkqkqrf eekrfkldhs vsstnghrwq ifqdwlgtdq dnldlanvnl
241  mlellvqkkk qleaeshaaq lqilmeflkv arrnkreqle qiqkelsvle edikrveems
301  glyspvseds tvpqfeapsp shssiidste ysqppgfsgs sqtkkqpwyn stlasrrkrl
361  tahfedleqc yfstrmsris ddsrtasqld efqeciskft rynsvrplat lsyasdlyng
421  ssivssiefd rdcdyfaiag vtkkikvyey dtviqdavdi hypenemtcn skisciswss
481  yhknllassd yegtvilwdg ftgqrskvyq ehekrcwsvd fnlmdpklla sgsddakvkl
541  wstnldnsva sieakanvcc vkfspssryh lafgcadhcv hyydlrntkq pimvfkghrk
601  aysyakfvsg eeivsastds qlklwnvgkp yclrsfkghi neknfvglas ngdyiacgse
661  nnslylyykg lsktlltfkf dtvksvldkd rkeddtnefv savcwralpd gesnvliaan
721  sqgtikvlel v
```

Human RFWD2 (isoform d24) cDNA Sequence

SEQ ID NO: 19

```
  1  atgtctggta gccgccaggc cgggtcgggc tccgctggga caagccccgg gtcctcggcg
 61  gcctcctcgg tgacttccgc ctcctcgtct ttatcctctt ccccgtcgcc gccttccgtg
121  gcggtttcgg cggcagcgct ggtgtccggc ggggtggccc aggccgccgg ctcgggcggc
181  ctcggggggcc cggtgcggcc tgtgttggtg gcgcccgccg tatcgggtag cggcggcggg
241  gcggtgtcca cgggcctgtc ccggcacagc tgcgcggcca ggcccagcgc cggcgtagga
301  ggcagcagct ccagcctagg cagcggcagc aggaagcgac ctctcctcgc cccctctgc
361  aacgggctca tcaactccta cgaggacaaa agcaacgact cgtatgccc catctgcttt
421  gatatgattg aagaagcata catgacaaaa tgtggccaca gcttttgcta caagtgtatt
481  catcagagtt tggaggacaa taatagatgt cccaagtgta actatgttgt ggacaatatt
541  gaccatctgt atcctaattt cttggtgaat gaactcattc ttaaacagaa gcaaagattt
601  gaggaaaaga ggttcaaatt ggaccactca aatggccaca ggtggcagat atttcaagat
661  tggttgggaa ctgaccaaga taaccttgat ttggccaatg tcaatcttat gttggagtta
721  ctagtgcaga agaagaaaca actggaagca gaatcacatg cagcccaact acagattctt
781  atggaattcc tcaaggttgc aagaagaaat aagagagagg aaatgagtgg cttatactct
```

-continued

```
 841  cctgtcagtg aggatagcac agtgcctcaa tttgaagctc cttctccatc acacagtagt 901  attattgatt ccacagaata cagccaacct ccaggtttca gtggcagttc tcagacaaag 961  aaacagcctt ggtataatag cacgttagca tcaagacgaa aacgacttac tgctcatttt 1021  gaagacttgg agcagtgtta cttttctaca aggatgtctc gtatctcaga tgacagtcga 1081  actgcaagcc agttggatga atttcaggaa tgcttgtcca agtttactcg atataattca 1141  gtacgacctt tagccacatt gtcatatgct agtgatctct ataatggttc cagtatagtc 1201  tctagtattg aatttgaccg ggattgtgac tattttgcga ttgctggagt tacaaagaag 1261  attaaagtct atgaatatga cactgtcatc caggatgcag tggatattca ttaccctgag 1321  aatgaaatga cctgcaattc gaaaatcagc tgtatcagtt ggagtagtta cataagaac 1381  ctgttagcta gcagtgatta tgaaggcact gttattttat gggatggatt cacaggacag 1441  aggtcaaagg tctatcagga gcatgagaag aggtgttgga gtgttgactt taatttgatg 1501  gatcctaaac tcttggcttc aggttctgat gatgcaaaag tgaagctgtg gtctaccaat 1561  ctagacaact cagtggcaag cattgaggca aaggctaatg tgtgctgtgt taaattcagc 1621  ccctcttcca gataccattt ggctttcggc tgtgcagatc actgtgtcca ctactatgat 1681  cttcgtaaca ctaaacagcc aatcatggta ttcaaaggac accgtaaagc agtctcttat 1741  gcaaagtttg tgagtggtga ggaaattgtc tctgcctcaa cagacagtca gctaaaactg 1801  tggaatgtag ggaaaccata ctgcctacgt tccttcaagg gtcatatcaa tgaaaaaaac 1861  tttgtaggcc tggcttccaa tggagattat atagcttgtg gaagtgaaaa taactctctc 1921  tacctgtact ataaaggact ttctaagact ttgctaactt ttaagtttga tacagtcaaa 1981  agtgttctcg acaaagaccg aaaagaagat gatacaaatg aatttgttag tgctgtgtgc 2041  tggagggcac taccagatgg ggagtccaat gtgctgattg ctgctaacag tcagggtaca 2101  attaaggtgc tagaattggt atga
```

Human RFWD2 (isoform d24) Amino Acid Sequence

SEQ ID NO: 20

```
   1  msgsrqagsg sagtspgssa assvtsasss lssspsppsv aysaaalvsg gvaqaagsgg 61  lggpvrpvlv apaysgsggg aystglsrhs caarpsagvg gssssslgsgs rkrpllaplc 121  nglinsyedk sndfvcpicf dmieeaymtk cghsfcykci hqslednnrc pkcnyvvdni 181  dhlypnflvn elilkqkqrf eekrfkldhs nghrwqifqd wlgtdqdnld lanvnlmlel 241  lvqkkkqlea eshaaqlqil meflkvarrn kreemsglys pvsedstvpq feapspshss 301  iidsteysqp pgfsgssqtk kqpwynstla srrkrltahf edleqcyfst rmsrisddsr 361  tasqldefqe clskftryns vrplatlsya sdlyngssiv ssiefdrdcd yfaiagvtkk 421  ikvyeydtvi qdavdihype nemtcnskis ciswssyhkn llassdyegt vilwdgftgq 481  rskvyqehek rcwsvdfnlm dpkllasgsd dakvklwstn ldnsvasiea kanvccvkfs 541  pssryhlafg cadhcvhyyd lrntkqpimv fkghrkaysy akfvsgeeiv sastdsqlkl 601  wnvgkpyclr sfkghinekn fvglasngdy iacgsennsl ylyykglskt lltfkfdtvk 661  svldkdrked dtnefvsavc wralpdgesn vliaansqgt ikvlelv
```

II. Agents and Compositions

Agents and compositions of the present invention are provided for us in the diagnosis, prognosis, prevention, and treatment of cancer (e.g., hematological cancers, such as DLBCL) and cancer subtypes thereof. Such agents and compositions can detect and/or modulate, e.g., up- or downregulate, expression and/or activity of gene products or fragments thereof encoded by biomarkers of the invention, including the biomarkers listed in Tables 1-9. Exemplary agents include antibodies, small molecules, peptides, peptidomimetics, natural ligands, and derivatives of natural ligands, that can either bind and/or activate or inhibit protein biomarkers of the invention, including the biomarkers listed in Tables 1-9, or fragments thereof; RNA interference, antisense, nucleic acid aptamers, etc. that can downregulate the expression and/or activity of the biomarkers of the invention, including the biomarkers listed in Tables 1-9, or fragments thereof.

In one embodiment, isolated nucleic acid molecules that specifically hybridize with or encode one or more biomarkers listed in Tables 1-9 or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules corresponding to the one or more biomarkers listed in Tables 1-9 can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a lymphoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of one or more biomarkers listed in Tables 1-9 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence of one or more biomarkers listed in Tables 1-9 or a portion thereof (i.e., 100, 200, 300, 400, 450, 500, or more nucleotides), can be isolated using standard molecular biology techniques and the sequence information provided herein. For example, a human cDNA can be isolated from a human cell line (from Stratagene, LaJolla, Calif., or Clontech, Palo Alto, Calif.) using all or portion of the nucleic acid molecule, or fragment thereof, as a hybridization probe and standard hybridization techniques (i.e., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989). Moreover, a nucleic acid molecule encompassing all or a portion of the nucleotide sequence of one or more biomarkers listed in Tables 1-9 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence, or fragment thereof, can be isolated by the polymerase chain reaction using oligonucleotide primers designed based upon the sequence of the one or more biomarkers listed in Tables 1-9, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed according to well known methods in the art. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequence of one or more biomarkers listed in Tables 1-9 can be prepared by standard synthetic techniques, i.e., using an automated DNA synthesizer.

Probes based on the nucleotide sequences of one or more biomarkers listed in Tables 1-9 can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express one or more biomarkers listed in Tables 1-9, such as by measuring a level of nucleic acid in a sample of cells from a subject, i.e., detecting mRNA levels of one or more biomarkers listed in Tables 1-9.

Nucleic acid molecules encoding proteins corresponding to one or more biomarkers listed in Tables 1-9 from different species are also contemplated. For example, rat or monkey cDNA can be identified based on the nucleotide sequence of a human and/or mouse sequence and such sequences are well known in the art. In one embodiment, the nucleic acid molecule(s) of the invention encodes a protein or portion thereof which includes an amino acid sequence which is sufficiently homologous to an amino acid sequence of one or more biomarkers listed in Tables 1-9, such that the protein or portion thereof modulates (e.g., enhance), one or more of the following biological activities: a) binding to the biomarker; b) modulating the copy number of the biomarker; c) modulating the expression level of the biomarker; and d) modulating the activity level of the biomarker.

As used herein, the language "sufficiently homologous" refers to proteins or portions thereof which have amino acid sequences which include a minimum number of identical or equivalent (e.g., an amino acid residue which has a similar side chain as an amino acid residue in one or more biomarkers listed in Tables 1-9, or fragment thereof) amino acid residues to an amino acid sequence of the biomarker, or fragment thereof, such that the protein or portion thereof modulates (e.g., enhance) one or more of the following biological activities: a) binding to the biomarker; b) modulating the copy number of the biomarker; c) modulating the expression level of the biomarker; and d) modulating the activity level of the biomarker.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of the biomarker, or a fragment thereof.

Portions of proteins encoded by nucleic acid molecules of the one or more biomarkers listed in Tables 1-9 are preferably biologically active portions of the protein. As used herein, the term "biologically active portion" of one or more biomarkers listed in Tables 1-9 is intended to include a portion, e.g., a domain/motif, that has one or more of the biological activities of the full-length protein.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The invention further encompasses nucleic acid molecules that differ from the nucleotide sequence of the one or more biomarkers listed in Tables 1-9, or fragment thereof due to degeneracy of the genetic code and thus encode the same protein as that encoded by the nucleotide sequence, or fragment thereof. In another embodiment, an isolated nucleic acid molecule of the invention has a nucleotide sequence encoding a protein having an amino acid sequence of one or more biomarkers listed in Tables 1-9, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of the one or more biomarkers listed in Tables 1-9, or fragment thereof. In another embodiment, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of the one or more biomarkers listed in Tables 1-9 may exist within a population (e.g., a mammalian and/or human population). Such genetic polymorphisms may exist among individuals within a population due to natural allelic variation. As used herein, the terms "gene" and "recombinant gene" refer to nucleic acid molecules comprising an open reading frame encoding one or more biomarkers listed in Tables 1-9, preferably a mammalian, e.g., human, protein. Such natural allelic variations can typically result in 1-5% variance in the nucleotide sequence of the one or more biomarkers listed in Tables 1-9. Any and all such nucleotide variations and resulting amino acid polymorphisms in the one or more biomarkers listed in Tables 1-9 that are the result of natural allelic variation and that do not alter the functional activity of the one or more biomarkers listed in Tables 1-9 are intended to be within the scope of the invention. Moreover, nucleic acid molecules encoding one or more biomarkers listed in Tables 1-9 from other species.

In addition to naturally-occurring allelic variants of the one or more biomarkers listed in Tables 1-9 sequence that may exist in the population, the skilled artisan will further appreciate that changes can be introduced by mutation into the nucleotide sequence, or fragment thereof, thereby leading to changes in the amino acid sequence of the encoded one or more biomarkers listed in Tables 1-9, without altering the functional ability of the one or more biomarkers listed in Tables 1-9. For example, nucleotide substitutions leading to amino acid substitutions at "non-essential" amino acid residues can be made in the sequence, or fragment thereof. A "non-essential" amino acid residue is a residue that can be altered from the wild-type sequence of the one or more biomarkers listed in Tables 1-9 without altering the activity of the one or more biomarkers listed in Tables 1-9, whereas an "essential" amino acid residue is required for the activity of the one or more biomarkers listed in Tables 1-9. Other amino acid residues, however, (e.g., those that are not conserved or only semi-conserved between mouse and human) may not be essential for activity and thus are likely to be amenable to alteration without altering the activity of the one or more biomarkers listed in Tables 1-9.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a protein homologous to one or more biomarkers listed in Tables 1-9, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more biomarkers listed in Tables 1-9 is preferably replaced with another amino acid residue from the same side chain family. Alternatively, in another embodiment, mutations can be introduced randomly along all or part of the coding sequence of the one or more biomarkers listed in Tables 1-9, such as by saturation mutagenesis, and the resultant mutants can be screened for an activity described herein to identify mutants that retain desired activity. Following mutagenesis, the encoded protein can be expressed recombinantly according to well known methods in the art and the activity of the protein can be determined using, for example, assays described herein.

The levels of one or more biomarkers listed in Tables 1-9 levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of one or more biomarkers listed in Tables 1-9 levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding One or more biomarkers listed in Tables 1-9. Other suitable probes for use in the diagnostic assays of the invention are described herein. Hybridization of an mRNA with the probe indicates that One or more biomarkers listed in Tables 1-9 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the One or more biomarkers listed in Tables 1-9 mRNA expression levels.

An alternative method for determining mRNA expression level in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the One or more biomarkers listed in Tables 1-9 mRNA.

As an alternative to making determinations based on the absolute expression level, determinations may be based on the normalized expression level of one or more biomarkers listed in Tables 1-9. Expression levels are normalized by correcting the absolute expression level by comparing its expression to the expression of a non-biomarker gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a protein corresponding to one or more biomarkers listed in Tables 1-9 can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express the biomarker of interest.

The present invention further provides soluble, purified and/or isolated polypeptide forms of one or more biomarkers listed in Tables 1-9, or fragments thereof. In addition, it is to be understood that any and all attributes of the polypeptides described herein, such as percentage identities, polypeptide lengths, polypeptide fragments, biological activities, antibodies, etc. can be combined in any order or combination with respect to any biomarker listed in Tables 1-9 and combinations thereof.

In one aspect, a polypeptide may comprise a full-length amino acid sequence corresponding to one or more biomarkers listed in Tables 1-9 or a full-length amino acid sequence with 1 to about 20 conservative amino acid substitutions. An amino acid sequence of any described herein can also be at least 50, 55, 60, 65, 70, 75, 80, 85, 90, 91, 92, 93, 94, 95, 96, 97, 98, 99, or 99.5% identical to the full-length sequence of one or more biomarkers listed in Tables 1-9, which is either described herein, well known in the art, or a fragment thereof. In another aspect, the present invention contemplates a composition comprising an isolated polypeptide corresponding to one or more biomarkers listed in Tables 1-9 polypeptide and less than about 25%, or alternatively 15%, or alternatively 5%, contaminating biological macromolecules or polypeptides.

The present invention further provides compositions related to producing, detecting, or characterizing such polypeptides, or fragment thereof, such as nucleic acids, vectors, host cells, and the like. Such compositions may serve as compounds that modulate the expression and/or activity of one or more biomarkers listed in Tables 1-9.

An isolated polypeptide or a fragment thereof (or a nucleic acid encoding such a polypeptide) corresponding to one or more biomarkers of the invention, including the biomarkers listed in Tables 1-9 or fragments thereof, can be used as an immunogen to generate antibodies that bind to said immunogen, using standard techniques for polyclonal and monoclonal antibody preparation according to well known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

For example, a polypeptide immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating a monoclonal antibody against one or more biomarkers of the invention, including the biomarkers listed in Tables 1-9, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the *Pharmacia Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology (NY)* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171, 496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad Sci. USA* 90:7427-7428; Marasco, W. A. et al. (1993) *Proc. Natl. Acad. Sci. USA* 90:7889-7893; Biocca, S. et al. (1994) *Biotechnology* (NY) 12:396-399; Chen, S-Y. et al. (1994) *Hum. Gene Ther.* 5:595-601; Duan, L et al. (1994) *Proc. Natl. Acad Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

Additionally, fully human antibodies could be made against biomarkers of the invention, including the biomarkers listed in Tables 1-9, or fragments thereof. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In one embodiment, an antibody for use in the instant invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Tables 1-9, or a fragment thereof. In one embodiment, the bispecific antibody could specifically bind to both a polypeptide or a fragment thereof and its natural binding partner(s) or a fragment(s) thereof.

In another aspect of this invention, peptides or peptide mimetics can be used to antagonize or promote the activity of one or more biomarkers of the invention, including one or more biomarkers listed in Tables 1-9, or a fragment(s) thereof. In one embodiment, variants of one or more biomarkers listed in Tables 1-9 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Tables 1-9, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere, J. (1986)*Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH2S—, —CH2—CH2-, —CH=CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982)(—CH(OH) CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers listed in Tables 1-9 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad Sci. USA* 89:1865-1869) or on phage (Scott and Smith (1990) *Science* 249:386-390); (Devlin (1990) *Science* 249:404-406); (Cwirla et al. (1990) *Proc. Natl. Acad Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

The invention also relates to chimeric or fusion proteins of the biomarkers of the invention, including the biomarkers listed in Tables 1-9, or fragments thereof. As used herein, a "chimeric protein" or "fusion protein" comprises one or more biomarkers of the invention, including one or more biomarkers listed in Tables 1-9, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the invention, including one or more biomarkers listed in Tables 1-9, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ1, or human IgC γ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the invention, including one or more biomarkerss listed in Tables 1-9, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21,20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296: 550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Tables 1-9). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) Nature 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g, for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-O-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (herein-after "Cech-type ribozymes") such as the one which occurs naturally in Tetrahymena thermophila (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g. antibodies, small molecules, peptides, fusion proteins, or small nucleic acids) can be incorporated into pharmaceutical compositions and administered to a subject in vivo. The compositions may contain a single such molecule or agent or any combination of agents described herein. Based on the genetic pathway analyses described herein, it is believed that such combinations of agents is especially effective in diagnosing, prognosing, preventing, and treating cancer. Thus, "single active agents" described herein can be combined with other pharmacologically active compounds ("second active agents") known in the art according to the methods and compositions provided herein. It is believed that certain combinations work synergistically in the treatment of particular types of cancer. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alpha-n1, interferon alpha-n3, interferon beta-Ia, and interferon gamma-Ib; GM-CF and GM-CSF; and EPO.

Particular proteins that can be used in the methods and compositions provided herein include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.). Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Antibodies that can be used in combination form include monoclonal and polyclonal antibodies. Examples of antibodies include, but are not limited to, trastuzumab (Herceptin®), rituximab (Rituxan®), bevacizumab (Avastin®), pertuzumab (Omnitarg®), tositumomab (Bexxar®), edrecolomab (Panorex®), and G250. Compounds of the invention can also be combined with, or used in combination with, anti-TNF-α antibodies. Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits provided herein. See, e.g., Emens, L. A., et al., Curr. Opinion Mol. Ther. 3(1):77-84 (2001).

Second active agents that are small molecules can also be used to in combination as provided herein. Examples of small molecule second active agents include, but are not limited to, anti-cancer agents, antibiotics, immunosuppressive agents, and steroids.

In some embodiments, well known "combination chemotherapy" regimens can be used. In one embodiment, the combination chemotherapy comprises a combination of two or more of cyclophosphamide, hydroxydaunorubicin (also known as doxorubicin or Adriamycin®), oncovorin (vincristine) and prednisone. In another preferred embodiment, the combination chemotherapy comprises a combination of cyclophosphamide, oncovorin, prednisone, and one or more chemotherapeutics selected from the group consisting of hydroxydaunorubicin, epirubicin, and motixantrone. In another embodiment, the combination chemotherapy comprises a combination of each of cyclophosphamide, hydroxydaunorubicin, oncovorin, and prednisone, referred to as "CHOP" chemotherapy. In still another embodiment, the combination therapy comprises CHOP-like chemotherapy. Examples of CHOP-like chemotherapy include, but are not limited to, CEOP (CHOP in which hydroxydaunorubicin is replaced with epirubicin) and CNOP (CHOP in which hydroxydaunorubicin is replaced with mitoxantrone, which is also known as novantrone).

Examples of other anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide;

floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cyclosporin A; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin;

SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, chlorambucil, fludarabine, dexamethasone (Decadron®), hydrocortisone, methylprednisolone, cilostamide, doxorubicin (Doxil®), forskolin, rituximab, cyclosporin A, cisplatin, vincristine, PDE7 inhibitors such as BRL-50481 and IR-202, dual PDE4/7 inhibitors such as IR-284, cilostazol, meribendan, milrinone, vesnarionone, enoximone and pimobendan, Syk inhibitors such as fostamatinib disodium (R406/R788), R343, R-112 and Excellair® (ZaBeCor Pharmaceuticals, Bala Cynwyd, Pa.).

III. Methods of Selecting Agents and Compositions

Another aspect of the invention relates to methods of selecting agents (e.g., antibodies, fusion proteins, peptides, small molecules, or small nucleic acids) which bind to, upregulate, downregulate, or modulate one or more biomarkers of the invention listed in Tables 1-9 and/or a cancer (e.g., a hematological cancer, such as DLBCL). Such methods utilize can use screening assays, including cell based and non-cell based assays.

In one embodiment, the invention relates to assays for screening candidate or test compounds which bind to or modulate the expression or activity level of, one or more biomarkers of the invention, including one or more biomarkers listed in Tables 1-9, or a fragment thereof. Such compounds include, without limitation, antibodies, proteins, fusion proteins, nucleic acid molecules, and small molecules.

In one embodiment, an assay is a cell-based assay, comprising contacting a cell expressing one or more biomarkers of the invention, including one or more biomarkers listed in Tables 1-9, or a fragment thereof, with a test compound and determining the ability of the test compound to modulate (e.g. stimulate or inhibit) the level of interaction between the biomarker and its natural binding partners as measured by direct binding or by measuring a parameter of cancer.

For example, in a direct binding assay, the biomarker polypeptide, a binding partner polypeptide of the biomarker, or a fragment(s) thereof, can be coupled with a radioisotope or enzymatic label such that binding of the biomarker polypeptide or a fragment thereof to its natural binding partner(s) or a fragment(s) thereof can be determined by detecting the labeled molecule in a complex. For example, the biomarker polypeptide, a binding partner polypeptide of the biomarker, or a fragment(s) thereof, can be labeled with $^{125}$I, $^{35}$S, $^{14}$C, or $^{3}$H, either directly or indirectly, and the radioisotope detected by direct counting of radioemission or by scintillation counting. Alternatively, the polypeptides of interest a can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interactions between one or more biomarkers of the invention, including one or more biomarkers listed in Tables 1-9, or a fragment thereof, and its natural binding partner(s) or a fragment(s) thereof, without the labeling of any of the interactants (e.g., using a microphysiometer as described in McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the blocking agents (e.g. antibodies, fusion proteins, peptides, nucleic acid molecules, or small molecules) to antagonize the interaction between a given set of polypeptides can be accomplished by determining the activity of one or more members of the set of interacting molecules. For example, the activity of one or more biomarkers of the invention, including one or more biomarkers listed in Tables 1-9, or a fragment thereof, can be determined by detecting induction of cytokine or chemokine response, detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the biomarker or a fragment thereof (e.g., modulations of biological pathways identified herein, such as modulated proliferation, apoptosis, cell cycle, and/or E2F transcription facto binding activity). Determining the ability of the blocking agent to bind to or interact with said polypeptide can be accomplished by measuring the ability of an agent to modulate immune responses, for example, by detecting changes in type and amount of cytokine secretion, changes in apoptosis or proliferation, changes in gene expression or activity associated with cellular identity, or by interfering with the ability of said polypeptide to bind to antibodies that recognize a portion thereof.

In yet another embodiment, an assay of the present invention is a cell-free assay in which one or more biomarkers of the invention, including one or more biomarkers listed in Tables 1-9 or a fragment thereof, e.g. a biologically active fragment thereof, is contacted with a test compound, and the ability of the test compound to bind to the polypeptide, or biologically active portion thereof, is determined. Binding of the test compound to the biomarker or a fragment thereof, can be determined either directly or indirectly as described above. Determining the ability of the biomarker or a fragment thereof to bind to its natural binding partner(s) or a fragment(s) thereof can also be accomplished using a technology such as real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. One or more biomarkers polypeptide or a fragment thereof can be immobilized on a BIAcore chip and multiple agents, e.g., blocking antibodies, fusion proteins, peptides, or small molecules, can be tested for binding to the immobilized biomarker polypeptide or fragment thereof. An example of using the BIA technology is described by Fitz et al. (1997) Oncogene 15:613.

The cell-free assays of the present invention are amenable to use of both soluble and/or membrane-bound forms of proteins. In the case of cell-free assays in which a membrane-bound form protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either the biomarker polypeptide, the natural binding partner(s) polypeptide of the biomarker, or fragments thereof, to facilitate separation of complexed from uncomplexed forms of one or both of the proteins, as well as to accommodate automation of the assay. Binding of a test compound in the assay can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-base fusion proteins, can be adsorbed onto glutathione Sepharose® beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells was washed to remove any unbound components, the matrix immobilized in the case of beads, complex determined either directly or indirectly, for example, as described above. Alternatively, the complexes can be dissociated from the matrix, and the level of binding or activity determined using standard techniques.

In an alternative embodiment, determining the ability of the test compound to modulate the activity of one or more biomarkers of the invention, including one or more biomarkers listed in Tables 1-9, or a fragment thereof, or of natural binding partner(s) thereof can be accomplished by determining the ability of the test compound to modulate the expression or activity of a gene, e.g., nucleic acid, or gene product, e.g., polypeptide, that functions downstream of the interaction. For example, inflammation (e.g., cytokine and chemokine) responses can be determined, the activity of the interactor polypeptide on an appropriate target can be determined, or the binding of the interactor to an appropriate target can be determined as previously described.

In another embodiment, modulators of one or more biomarkers of the invention, including one or more biomarkers listed in Tables 1-9, or a fragment thereof, are identified in a method wherein a cell is contacted with a candidate compound and the expression or activity level of the biomarker is determined. The level of expression of biomarker mRNA or polypeptide or fragments thereof in the presence of the candidate compound is compared to the level of expression of biomarker mRNA or polypeptide or fragments thereof in the absence of the candidate compound. The candidate compound can then be identified as a modulator of biomarker expression based on this comparison. For example, when expression of biomarker mRNA or polypeptide or fragments thereof is greater (statistically significantly greater) in the presence of the candidate compound than in its absence, the candidate compound is identified as a stimulator of biomarker expression. Alternatively, when expression of biomarker mRNA or polypeptide or fragments thereof is reduced (statistically significantly less) in the presence of the candidate compound than in its absence, the candidate compound is identified as an inhibitor of biomarker expression. The expression level of biomarker mRNA or polypeptide or fragments thereof in the cells can be determined by methods described herein for detecting biomarker mRNA or polypeptide or fragments thereof.

In yet another aspect of the invention, biomarker of the invention, including one or more biomarkers listed in Tables 1-9, or a fragment thereof, can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other polypeptides which bind to or interact with the biomarker or fragments thereof and are involved in activity of the biomarkers. Such biomarker-binding proteins are also likely to be involved in the propagation of signals by the biomarker polypeptides or biomarker natural binding partner(s) as, for example, downstream elements of one or more biomarkers-mediated signaling pathway.

The two-hybrid system is based on the modular nature of most transcription factors, which consist of separable DNA-binding and activation domains. Briefly, the assay utilizes two different DNA constructs. In one construct, the gene that codes for one or more biomarkers polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming one or more biomarkers-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with one or more biomarkers polypeptide of the invention, including one or more biomarkers listed in Tables 1-9 or a fragment thereof.

In another aspect, the invention pertains to a combination of two or more of the assays described herein. For example, a modulating agent can be identified using a cell-based or a cell-free assay, and the ability of the agent to modulate the activity of one or more biomarkers polypeptide or a fragment thereof can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

IV. Pharmaceutical Compositions

Agents that modulate the expression or activity level of one or more biomarkers of the invention, including one or more biomarkers listed in Tables 1-9 or a fragment thereof, including, e.g., blocking antibodies, peptides, fusion proteins, nucleic acid molecules, and small molecules) can be incorporated into pharmaceutical compositions suitable for administration to a subject. Such compositions typically comprise the antibody, peptide, fusion protein or small molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., blocking antibodies, peptides, fusion proteins, or small molecules that inhibit or enhance the interactions between or activity of one or more biomarkers polypeptide or a fragment thereof and its natural binding partner(s) or a fragment(s) thereof) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i. e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In some embodiments, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity of one or more biomarkers of the invention, including biomarkers listed in Tables 1-9 or fragments thereof. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the scope of knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such polypeptides may include, for example, a toxin such as abrin, ricin A, *pseudomonas* exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985); and Thorpe et al. "The Preparation And Cytotoxic Properties Of Antibody-Toxin Conjugates", Immunol. Rev. 62:119-58 (1982). Alternatively, an antibody can be conjugated to a second antibody to form an antibody heteroconjugate as described by Segal in U.S. Pat. No. 4,676,980.

The above described modulating agents may be administered it the form of expressible nucleic acids which encode said agents. Such nucleic acids and compositions in which they are contained, are also encompassed by the present invention. For instance, the nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The biomarkers of the invention described herein, including the biomarkers listed in Tables 1-9 or fragments thereof, can be used in one or more of the following methods: a) screening assays; b) predictive medicine (e.g., diagnostic assays, prognostic assays, and monitoring of clinical trials); and c) methods of treatment (e.g., therapeutic and prophylactic, e.g., by up- or down-modulating the copy number, level of expression, and/or level of activity of the one or more biomarkers).

The isolated nucleic acid molecules of the invention can be used, for example, to (a) express one or more biomarkers of the invention, including one or more biomarkers listed in Tables 1-9 or a fragment thereof (e.g., via a recombinant expression vector in a host cell in gene therapy applications or synthetic nucleic acid molecule), (b) detect biomarker mRNA or a fragment thereof (e.g., in a biological sample) or a genetic alteration in one or more biomarkers gene, and/or (c) modulate biomarker activity, as described further below. The biomarker polypeptides or fragments thereof can be used to treat conditions or disorders characterized by insufficient or excessive production of one or more biomarkers polypeptide or fragment thereof or production of biomarker polypeptide inhibitors. In addition, the biomarker polypeptides or fragments thereof can be used to screen for naturally occurring biomarker binding partner(s), to screen for drugs or compounds which modulate biomarker activity, as well as to treat conditions or disorders characterized by insufficient or excessive production of biomarker polypeptide or a fragment thereof or production of biomarker polypeptide forms which have decreased, aberrant or unwanted activity compared to biomarker wild-type polypeptides or fragments thereof (e.g., cancers, including hematological cancers, such as DLBCL).

A. Screening Assays

In one aspect, the present invention relates to a method for preventing in a subject, a disease or condition associated with an unwanted, more than desirable, or less than desirable, expression and/or activity of one or more biomarkers described herein. Subjects at risk for a disease that would benefit from treatment with the claimed agents or methods can be identified, for example, by any one or combination of diagnostic or prognostic assays known in the art and described herein (see, for example, agents and assays described in III. Methods of Selecting Agents and Compositions).

B. Predictive Medicine

The present invention also pertains to the field of predictive medicine in which diagnostic assays, prognostic assays, and monitoring of clinical trials are used for prognostic (predictive) purposes to thereby treat an individual prophylactically. Accordingly, one aspect of the present invention relates to diagnostic assays for determining the expression and/or activity level of biomarkers of the invention, including biomarkers listed in Tables 1-9 or fragments thereof, in the context of a biological sample (e.g., blood, serum, cells, or tissue) to thereby determine whether an individual is afflicted with a disease or disorder, or is at risk of developing a disorder, associated with aberrant or unwanted biomarker expression or activity. The present invention also provides for prognostic (or predictive) assays for determining whether an individual is at risk of developing a disorder associated with biomarker polypeptide, nucleic acid expression or activity. For example, mutations in one or more biomarkers gene can be assayed in a biological sample.

Such assays can be used for prognostic or predictive purpose to thereby prophylactically treat an individual prior to the onset of a disorder characterized by or associated with biomarker polypeptide, nucleic acid expression or activity.

Another aspect of the invention pertains to monitoring the influence of agents (e.g., drugs, compounds, and small nucleic acid-based molecules) on the expression or activity of biomarkers of the invention, including biomarkers listed in Tables 1-9, or fragments thereof, in clinical trials. These and other agents are described in further detail in the following sections.

1. Diagnostic Assays

The present invention provides, in part, methods, systems, and code for accurately classifying whether a biological sample is associated with a cancer or a clinical subtype thereof (e.g., a hematological cancer, such as DLBCL). In some embodiments, the present invention is useful for classifying a sample (e.g., from a subject) as a cancer sample using a statistical algorithm and/or empirical data (e.g., the presence or level of one or biomarkers described herein).

An exemplary method for detecting the level of expression or activity of one or more biomarkers of the invention, including one or more biomarkers listed in Tables 1-9 or fragments thereof, and thus useful for classifying whether a sample is associated with cancer or a clinical subtype thereof (e.g., a hematological cancer, such as DLBCL), involves obtaining a biological sample from a test subject and contacting the biological sample with a compound or an agent capable of detecting the biomarker (e.g., polypeptide or nucleic acid that encodes the biomarker or fragments thereof) such that the level of expression or activity of the biomarker is detected in the biological sample. In some embodiments, the presence or level of at least one, two, three, four, five, six, seven, eight, nine, ten, or more biomarkers of the invention are determined in the individual's sample. In certain instances, the statistical algorithm is a single learning statistical classifier system. Exemplary statistical analyses are presented in the Examples and can be used in certain embodiments. In other embodiments, a single learning statistical classifier system can be used to classify a sample as a cancer sample, a cancer subtype sample, or a non-cancer sample based upon a prediction or probability value and the presence or level of one or more biomarkers described herein. The use of a single learning statistical classifier system typically classifies the sample as a cancer sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the cancer classification results to a clinician, e.g., an oncologist or hematologist.

In another embodiment, the method of the present invention further provides a diagnosis in the form of a probability that the individual has a cancer or a clinical subtype thereof. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having cancer or a clinical subtype thereof. In yet another embodiment, the method of the present invention further provides a prognosis of cancer in the individual. For example, the prognosis can be surgery, development of a clinical subtype of the cancer (e.g., subtype of DLBCL), development of one or more symptoms, development of malignant cancer, or recovery from the disease. In some instances, the method of classifying a sample as a cancer sample is further based on the symptoms (e.g., clinical factors) of the individual from which the sample is obtained. The symptoms or group of symptoms can be, for example, those associated with the IPI. In some embodiments, the diagnosis of an individual as having cancer or a clinical subtype thereof is followed by administering to the individual a therapeutically effective amount of a drug useful for treating one or more symptoms associated with cancer or the cancer.

In some embodiments, an agent for detecting biomarker mRNA, genomic DNA, or fragments thereof is a labeled nucleic acid probe capable of hybridizing to biomarker mRNA, genomic DNA, or fragments thereof. The nucleic acid probe can be, for example, full-length biomarker nucleic acid, or a portion thereof, such as an oligonucleotide of at least 15, 30, 50, 100, 250 or 500 nucleotides in length and sufficient to specifically hybridize under stringent conditions well known to a skilled artisan to biomarker mRNA or genomic DNA. Other suitable probes for use in the diagnostic assays of the invention are described herein.

A preferred agent for detecting one or more biomarkers listed in Tables 1-9 or a fragment thereof is an antibody capable of binding to the biomarker, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect biomarker mRNA, polypeptide, genomic DNA, or fragments thereof, in a biological sample in vitro as well as in vivo. For example, in vitro techniques for detection of biomarker mRNA or a fragment thereof include Northern hybridizations and in situ hybridizations. In vitro techniques for detection of biomarker polypeptide include enzyme linked immunosorbent assays (ELISAs), Western blots, immunoprecipitations and immunofluorescence. In vitro techniques for detection of biomarker genomic DNA or a fragment thereof include Southern hybridizations. Furthermore, in vivo techniques for detection of one or more biomarkers polypeptide or a fragment thereof include introducing into a subject a labeled anti-biomarker antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain mRNA molecules from the test subject or genomic DNA molecules from the test subject. A preferred biological sample is a hematological tissue (e.g., a sample comprising blood, plasma, B cell, bone marrow, etc.) sample isolated by conventional means from a subject.

In another embodiment, the methods further involve obtaining a control biological sample from a control subject, contacting the control sample with a compound or agent capable of detecting polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof of one or more biomarkers listed in Tables 1-9 such that the presence of biomarker polypeptide, mRNA, genomic DNA, or fragments thereof, is detected in the biological sample, and comparing the presence of biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof in the control sample with the presence of biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof in the test sample.

The invention also encompasses kits for detecting the presence of a polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, of one or more biomarkers listed in Tables 1-9 in a biological sample. For example, the kit can comprise a labeled compound or agent capable of detecting one or more biomarkers polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, in a biological sample; means for determining the amount of the biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, f in the sample; and means for comparing the amount of the biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, in the sample with a standard. The compound or agent can be packaged in a suitable container. The kit can further comprise instructions for using the kit to detect the biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof.

2. Prognostic Assays

The diagnostic methods described herein can furthermore be utilized to identify subjects having or at risk of developing a disease or disorder associated with aberrant expression or activity of one or more biomarkers of the invention, including one or more biomarkers listed in Tables 1-9, or a fragment thereof. As used herein, the term "aberrant" includes biomarker expression or activity levels which deviates from the normal expression or activity in a control.

The assays described herein, such as the preceding diagnostic assays or the following assays, can be utilized to identify a subject having or at risk of developing a disorder associated with a misregulation of biomarker activity or expression, such as in a cancer (e.g., hematological cancer, such as DLBCL). Alternatively, the prognostic assays can be utilized to identify a subject having or at risk for developing a disorder associated with a misregulation of biomarker activity or expression. Thus, the present invention provides a method for identifying and/or classifying a disease associated with aberrant expression or activity of one or more biomarkers of the invention, including one or more biomarkers listed in Tables 1-9, or a fragment thereof. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant biomarker expression or activity. For example, such methods can be used to determine whether a subject can be effectively treated with an agent for a cancer (e.g., hematological cancer, such as DLBCL). Thus, the present invention provides methods for determining whether a subject can be effectively treated with an agent for a disease associated with aberrant biomarker expression or activity in which a test sample is obtained and biomarker polypeptide or nucleic acid expression or activity is detected (e.g., wherein a significant increase or decrease in biomarker polypeptide or nucleic acid expression or activity relative to a control is diagnostic for a subject that can be administered the agent to treat a disorder associated with aberrant biomarker expression or activity). In some embodiments, significant increase or decrease in biomarker expression or activity comprises at least 2 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher or lower, respectively, than the expression activity or level of the marker in a control sample.

The methods of the invention can also be used to detect genetic alterations in one or more biomarkers of the invention, including one or more biomarkers listed in Tables 1-9 or a fragment thereof, thereby determining if a subject with the altered biomarker is at risk for cancer (e.g., a hematological cancer, such as DLBCL) characterized by aberrant biomarker activity or expression levels. In preferred embodiments, the methods include detecting, in a sample of cells from the subject, the presence or absence of a genetic alteration characterized by at least one alteration affecting the integrity of a gene encoding one or more biomarkers polypeptide, or the mis-expression of the biomarker. For example, such genetic alterations can be detected by ascertaining the existence of at least one of 1) a deletion of one or more nucleotides from one or more biomarkers gene, 2) an addition of one or more nucleotides to one or more biomarkers gene, 3) a substitution of one or more nucleotides of one or more biomarkers gene, 4) a chromosomal rearrangement of one or more biomarkers gene, 5) an alteration in the level of a messenger RNA transcript of one or more biomarkers gene, 6) aberrant modification of one or more biomarkers gene, such as of the methylation pattern of the genomic DNA, 7) the presence of a non-wild type splicing pattern of a messenger RNA transcript of one or more biomarkers gene, 8) a non-wild type level of one or more biomarkers polypeptide, 9) allelic loss of one or more biomarkers gene, and 10) inappropriate post-translational modification of one or more biomarkers polypeptide. As described herein, there are a large number of assays known in the art which can be used for detecting alterations in one or more biomarkers gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in one or more biomarkers gene (see Abravaya et al. (1995) Nucleic Acids Res. 23:675-682). This method can include the steps of collecting a sample of cells from a subject, isolating nucleic acid (e.g., genomic DNA, mRNA, cDNA, small RNA, mature miRNA, pre-miRNA, pri-miRNA, miRNA*, anti-miRNA, or a miRNA binding site, or a variant thereof) from the cells of the sample, contacting the nucleic acid sample with one or more primers which specifically hybridize to one or more biomarkers gene of the invention, including the biomarker genes listed in Tables 1-9, or fragments thereof, under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in one or more biomarkers gene of the invention, including one or more biomarkers listed in Tables 1-9, or a fragment thereof, from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in one or more biomarkers gene of the invention, including a gene listed in Tables 1-9, or a fragment thereof, can be identified by hybridizing a sample and control nucleic acids, e.g., DNA, RNA, mRNA, small RNA, cDNA, mature miRNA, pre-miRNA, pri-miRNA, miRNA*, anti-miRNA, or a miRNA binding site, or a variant thereof, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in one or more biomarkers can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence one or more biomarkers gene of the invention, including a gene listed in Tables 1-9, or a fragment thereof, and detect mutations by comparing the sequence of the sample biomarker gene with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996)

Adv. Chromatogr. 36:127-162; and Griffin et al. (1993) Appl. Biochem. Biotechnol. 38:147-159).

Other methods for detecting mutations in one or more biomarkers gene of the invention, including a gene listed in Tables 1-9, or fragments thereof, include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217: 286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker genes of the invention, including genes listed in Tables 1-9, or fragments thereof, obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in biomarker genes of the invention, including genes listed in Tables 1-9, or fragments thereof. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992) Genet. Anal. Tech. Appl. 9:73-79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA. In some embodiments, the hybridization reactions can occur using biochips, microarrays, etc., or other array technology that are well known in the art.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving one or more biomarkers of the invention, including one or more biomarkers listed in Tables 1-9, or fragments thereof.

3. Monitoring of Effects During Clinical Trials

Monitoring the influence of agents (e.g., drugs) on the expression or activity of one or more biomarkers of the invention, including one or more biomarkers listed in Tables 1-9, or a fragment thereof (e.g., the modulation of a cancer state) can be applied not only in basic drug screening, but also in clinical trials. For example, the effectiveness of an agent determined by a screening assay as described herein to increase expression and/or activity of one or more biomarkers of the invention, including one or more biomarkers listed in Tables 1-9 or a fragment thereof, can be monitored in clinical trials of subjects exhibiting decreased expression and/or activity of one or more biomarkers of the invention, including one or more biomarkers of the invention, including one or more biomarkers listed in Tables 1-9, or a fragment thereof, relative to a control reference. Alternatively, the effectiveness of an agent determined by a screening assay to decrease expression and/or activity of one or more biomarkers of the invention, including one or more biomarkers listed in Tables 1-9, or a fragment thereof, can be monitored in clinical trials of subjects exhibiting decreased expression and/or activity of the biomarker of the invention, including one or more biomarkers listed in Tables 1-9 or a fragment thereof relative to a control reference. In such clinical trials, the expression and/or activity of the biomarker can be used as a "read out" or marker of the phenotype of a particular cell.

In some embodiments, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a preadministration sample from a subject prior to administration of the agent; (ii) detecting the level of expression and/or activity of one or more biomarkers of the invention, including one or more biomarkers listed in Tables 1-9 or fragments thereof in the preadministration sample; (iii) obtaining one or more post-administration samples from the subject; (iv) detecting the level of expression or activity of the biomarker in the post-administration samples; (v) comparing the level of expression or activity of the biomarker or fragments thereof in the preadministration sample with the that of the biomarker in the post administration sample or samples; and (vi) altering the administration of the agent to the subject accordingly. For example, increased administration of the agent may be desirable to increase the expression or activity of one or more biomarkers to higher levels than detected (e.g., to increase the effectiveness of the agent.) Alternatively, decreased administration of the agent may be desirable to decrease expression or activity of the biomarker to lower levels than detected (e.g., to decrease the effectiveness of the agent.) According to such an embodiment, biomarker expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a disorder characterized by insufficient or excessive production of biomarkers of the invention, including biomarkers listed in Tables 1-9 or fragments thereof, which have aberrant expression or activity compared to a control. Moreover, agents of the invention described herein can be used to detect and isolate the biomarkers or fragments thereof, regulate the bioavailability of the biomarkers or fragments thereof, and modulate biomarker expression levels or activity.

1. Prophylactic Methods

In one aspect, the invention provides a method for preventing in a subject, a disease or condition associated with an aberrant expression or activity of one or more biomarkers of the invention, including one or more biomarkers listed in Tables 1-9 or a fragment thereof, by administering to the subject an agent which modulates biomarker expression or at least one activity of the biomarker. Subjects at risk for a disease or disorder which is caused or contributed to by aberrant biomarker expression or activity can be identified by, for example, any or a combination of diagnostic or prognostic assays as described herein. Administration of a prophylactic agent can occur prior to the manifestation of symptoms characteristic of the biomarker expression or activity aberrancy, such that a disease or disorder is prevented or, alternatively, delayed in its progression.

2. Therapeutic Methods

Another aspect of the invention pertains to methods of modulating the expression or activity or interaction with natural binding partner(s) of one or more biomarkers of the invention, including one or more biomarkers listed in Tables 1-9 or fragments thereof, for therapeutic purposes. The biomarkers of the invention have been demonstrated to correlate with cancer (e.g., a hematological cancer, such as DLBCL). Accordingly, the activity and/or expression of the biomarker, as well as the interaction between one or more biomarkers or a fragment thereof and its natural binding partner(s) or a fragment(s) thereof can be modulated in order to modulate the immune response.

Modulatory methods of the invention involve contacting a cell with one or more biomarkers of the invention, including one or more biomarkers of the invention, including one or more biomarkers listed in Tables 1-9 or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the invention, including one or more biomarkers of the invention, including one or more biomarkers listed in Tables 1-9 or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Tables 1-9 or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the invention listed in Tables 1-9 or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regiment and dosages of these aforementioned chemotherapeutic drugs that are therapeutically effective will depend on the particular cancer (e.g., a hematological cancer, such as DLBCL), being treated, the extent of the disease and other factors familiar to the physician of skill in the art and can be determined by the physician.

V. Administration of Agents

The cancer diagnostic, prognostic, prevention, and/or treatment modulating agents of the invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of a blocking antibody may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents of the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays. In addition, an antibody of the invention can also be administered in combination therapy with, e.g., chemotherapeutic agents, hormones, antiangiogens, radiolabelled, compounds, or with surgery, cryotherapy, and/or radiotherapy. An antibody of the invention can also be administered in conjunction with other forms of conventional therapy, either consecutively with, pre- or post-conventional therapy. For example, the antibody can be administered with a therapeutically effective dose of chemotherapeutic agent. In another embodiment, the antibody can be administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regiment and dosages of these aforementioned chemotherapeutic drugs that are therapeutically effective will depend on the particular immune disorder, e.g., Hodgkin lymphoma, being treated, the extent of the disease and other factors familiar to the physician of skill in the art and can be determined by the physician.

In addition, the agents of the invention described herein can be administered using nanoparticle-based composition and delivery methods well known to the skilled artisan. For example, nanoparticle-based delivery for improved nucleic acid (e.g., small RNAs) therapeutics are well known in the art (Expert Opinion on Biological Therapy 7:1811-1822).

This invention is further illustrated by the following examples which should not be construed as limiting. The contents of all references, patents and published patent applications cited throughout this application, as well as the Figures, are incorporated herein by reference.

EXAMPLES

Example 1: Materials and Methods Used in Examples 2-14

A. Subjects and Primary Tumor Samples

High molecular weight DNA and total RNA were extracted from frozen biopsy specimens of newly diagnosed and previously untreated primary DLBCLs according to IRB-approved protocols from three institutions (Mayo Clinic, Brigham & Women's Hospital, and Dana-Farber Cancer Institute). For one subset of patients, informed consent was obtained (Mayo). For other patients, a waiver to obtain informed consent was granted by the local IRBs because otherwise discarded tissue was used. The series included 72 DLBCLs from patients who were treated with a Rituxan® (rituximab)-containing, anthracycline-based combination chemotherapy regimen (R-CHOP-like) and had long-term follow up; 68 of these patients had available information on all clinical parameters in the IPI (Table S6).

Specifically, frozen tissue sections (10-20×20 mm) were homogenized in 1 ml of G2-buffer supplemented with 2 ml RNase (Qiagen) using lysing matrix tubes A for DNA extraction and in 1 ml of Trizol (Invitrogen) in lysing matrix tubes D in an automated homogenizer (MP Biomedicals). Subsequently, high molecular weight genomic DNA was extracted using the genomic buffer kit with 20/G genomic-tips (Qiagen) following the manufactures recommendation and RNA was extracted using the standard Trizol method (Invitrogen).

DLBCL diagnoses and >80% tumor involvement were confirmed by expert hematologists (SJR, JLK and AD). The series included 72 DLBCLs from patients who were treated with a Rituxan® (rituximab)-containing, anthracycline-based combination chemotherapy regimen (R-CHOP-like) and had long-term follow up; 68 of these patients had available information on all clinical parameters in the IPI (Table 9).

B. High-Density Single Nucleotide Polymorphism (HD SNP) Array Analysis

Primary DLBCL DNA samples and normal DNA specimens were profiled on Affymetrix HD-SNP arrays 6.0. The Affymetrix SNP Array 6.0 queries more than 1.8 million genome loci, or markers, with more than 906K markers corresponding to known polymorphic loci (SNP probe-sets), and more than 946K markers positioned at non-polymorphic loci for the detection of copy-number variation (CN probes). Each of the two alleles at a SNP locus is measured by triplicate 25-mers, while a single 25-mer is used to measure each CN locus. For the detection of CN alterations, the SNP array 6.0 data was processed through a previously described analytical pipeline (TCGA (2008) Nature 455:1061-1068). Across-sample GISTIC analysis of the segmented data was carried out to identify statistically significant CNAs (Beroukhim et al. (2007) Proc Natl Acad Sci USA 104:20007-20012). Alteration regions with FDR q-values below 0.25 were considered significant. Within each region, a peak (or peaks) was identified as the contiguous set (or sets) of loci with highest q-values.

Specifically, a total of 180 primary diffuse large B-cell lymphomas (DLBCL) and 41 normal DNA samples were profiled on Affymetrix SNP array 6.0, comprising 21 peripheral blood lymphocyte samples, and 20 HapMap samples. A set of 133 normal samples already profiled for the TCGA project (glioblastoma plates TRIBE, GHATS, FALLS, TRIGS, SHUNT, PUNAS, and STAIR)(TCGA (2008) Nature 455:1061-1068) was added to the set of within-plate normals for the nearest-neighbor normalization step described further in the next section. The Affymetrix SNP Array 6.0 queries more than 1.8 million genome loci, or markers, with more than 906K markers corresponding to known polymorphic loci (SNP probe sets), and more than 946K markers positioned at non-polymorphic loci for the detection of copy-number variation (CN probes). Each of the two alleles at a SNP locus is measured by triplicate 25-mers, while a single 25-mer is used to measure each CN locus.

For 169 of the DLBCL samples, mRNA expression profiles on Affymetrix U133A/B (Monti et al. (2005) Blood 105:1851-1861) (n=78) and U133plus2 (n=91) were also available. A summary of the samples analyzed is listed in Table 10.

C. Expression Profiling

RNA samples from 169 of the primary DLBCLs were transcriptionally profiled and the data were processed using Affymetrix' MAS5 summarization method according to a number of steps.

Preprocessing:

The raw '.cel' files were converted into probeset-specific expression values using Affymetrix' MAS5 summarization method as implemented in the BioConductor package 'simpleaffy' (Gentleman et al. (2004) Genome Biol 5:R80). All samples were scaled to have a mean expression level of 100. Furthermore, since the expression profiles originated from two separate batches profiled at different times and on different chips (the first batch was profiled on U133A/B chip pairs, and the 2nd batch was profiled on the U133plus2 chip), data were further normalized by carrying out a gene-specific normalization, whereby the mean and standard deviation of a gene in the 2nd batch were set to the mean and standard deviation of the corresponding gene in the 1st batch. In particular, for each profile j in batch 2, the expression of gene i was transformed as follows:

$$g'_{ij} = \frac{g_{ij} - \mu_i^{(2)}}{s_i^{(2)}} \times s_i^{(1)} + \mu_i^{(1)},$$

where $\mu_i^{(b)}$ and $\mu_i^{(b)}$ denote the mean and standard deviation of gene i in batch b=1,2.

Prediction of Expression Profile-Defined Phenotypes:

Classification algorithms were used to label the DLBCL samples with respect to two expression profile-defined phenotypes relevant to DLBCL biology: i) the 3-class OxPhos/BCR/HR (CCC) phenotype (Chen et al. (2008) Blood 111:2230-2237; Monti et al. (2005) Blood 105:1851-1861; Polo et al. (2007) Proc Natl Acad Sci USA 104:3207-3212); and ii) the 2-class GCB/ABC, Cell-of-origin (COO) phenotype (Alizadeh et al. (2000) Nature 4051:503-511; Wright et al. (2003) PNAS 100:9991-9996). For the assignment of the OxPhos/BCR/HR phenotype, an ensemble classification scheme was used (Polo et al. (2007) Proc Natl Acad Sci USA 104:3207-3212). Thirteen distinct classifiers were trained on the original 141-sample dataset and applied to the a set of 116 new samples profiled on the U133plus2 chip (this set included 89 samples with paired SNP array profiles, 18 samples without paired SNP array profiles, and 9 samples from the original series re-hybridized on the new chip and used as internal controls). Class membership was determined by majority voting, and samples with fewer than 10 of 13 classifiers in agreement were left unassigned. The number and identity of the predictive features (probesets) used to build each of the 13 classifiers were determined by leave-one-out cross-validation in the training set. Table 4 reports the class assignments based on the "Best 10/13" rule. For the assignment of the COO phenotype, a publicly available dataset of 181 DLBCL samples profiled on the Affymetrix U133plus2 chip (Lenz et al. (2008) Science 319:1676-1679) was used as a training set. This dataset was used to train a linear-predictive-score (LPS) classifier (Wright et al. (2003) PNAS 100:9991-9996), which was then applied to the dataset described herein. Samples classified as either GCB or ABC with probability less than 0.9 were left unassigned.

De-Novo Clustering of Expression Profiles:

The new series of 116 DLBCL samples profiled on U133plus2 (see previous section) was used to validate the 3-class OxPhos/BCR/HR clustering previously published. To this end, the expression data was projected on the space of the 2118 probesets used for the original clustering, and Consensus Clustering was run using Hierarchical Clustering with average linkage as the agglomeration criterion, and Euclidean distance as the adjacency measure. The algorithm yielded a very stable 3-class structure. The class assignments of the ensemble classifier described in the previous section were then compared with the class assignments obtained by Consensus Clustering (Monti et al. (2005) Blood 105:1851-1861). Of the 97 samples that had a class assignment based on the "best 10/13" rule (19 were left unassigned), 83 were in agreement between the two methods, corresponding to an accuracy of 86.6%. This result provides additional evidence that the 3-class structure previously described represents the dominant structure in gene expression space (FIG. 13). For the detection of CN alterations, the SNP 6.0 CEL file data pass through three main processing steps: i) copy number (CN) measurements are inferred from raw intensities; ii) within each sample, CN values are "smoothed" by a noise-reduction segmentation algorithm; iii) across-sample analysis of the segmented data is carried out to identify statistically significant CN alteration loci (amplifications and deletions).

Copy Number Inference:

The inference of copy number values from raw '.CEL' files is encoded in a GenePattern pipeline that runs the following modules:

(a) SNPFileCreator:

Raw CEL files are converted to a representation with a single value for each probeset representing a SNP allele or a copy number probe. Brightness correction is first performed by scaling the probe-level values of each CEL file so that the sample-specific median value is 1000. Next, MBEI (Li et al. (2001) Proc Natl Acad Sci USA 98:31-36) is used to map probe-level values in each sample to a reference sample (chosen as the normal sample with total intensity closest to the median total intensity in the plate). Finally, multiple probes for the same locus are summarized into a single value using median polish (Mosteller et al. (1977) Data analysis and regression. Addison-Wesley (Reading, Mass.)) across the samples in the plate (96 samples).

(b) CopyNumberInference:

The summarized intensities, which are expressed in an arbitrary scale, are mapped to copy number values by estimating a probeset-specific linear calibration curve, with intercept and slope corresponding to background and scale, respectively. SNP probesets and copy-number (CN) probes are handled separately. For CN probes, the conversion is performed by using prior measurements of intensity in 5 cell lines with varying copies (from 1 to 5) of the X chromosome, and by then extrapolating to the entire genome. For SNP probesets, the background and scale are estimated using the allele-specific probeset-specific cluster centers (i.e., mean intensities of the A and B probesets for the three possible genotypes; AA, AB, and BB) produced by the Birdseed algorithm (Korn et al. (2008) Nature Genetics 40:1253-1260). Birdseed is applied only to normal samples within the analyzed plate that pass a quality control (FQC call rate ≥86%, Birdseed call rate >90%).

(c) RemoveCopyNumberOutliers:

A value is considered to be an outlier if it satisfies several criteria relative to neighboring values on the same sample, separately assessed in the 5' and 3' directions: the median copy-number of the 5 nearest neighbors in a given direction is measured; if the difference between the median and the value under consideration is greater than 0.3, and the difference between their $\log_2$ values is greater than $\log_2(6)$, the value is called an outlier. If the value is an outlier with respect to both its left neighbors and its right neighbors, it is replaced with the median of the three values centered on itself.

(d) DivideByNormals:

Systematic bias in copy-number estimation is removed using 5-Nearest-Neighbor normalization (TCGA (2008) Nature 455:1061-1068). For each tumor, the 5 closest normal samples by Euclidean distance are identified among the panel of available normal samples. The distance is computed between $\log_2$ values measured on the entire genome excluding regions of known CNVs and the X and Y chromosomes. The average $\log_2$ values of these normal samples are then subtracted, at each position, from the tumor's $\log_2$ values.

(e) QualityControl:

Tumor samples that fail Birdseed quality control are removed. In addition, samples are rejected if either their copy-number noise level (proportional to the median of pair-wise absolute differences of $\log_2$-ratios of adjacent probes) or their number of segments as found by the segmentation is an outlier. A value is an outlier if it falls k*IQRs (inter quartile range) above the third quartile. The value k=2 is used for the noise level and k=3 for number of segments. In all, 180 tumors passed quality control for the SNP 6.0 platform.

Segmentation:

Segmentation of normalized $\log_2$-ratios was performed using the Circular Binary Segmentation (CBS) algorithm version 1.12.0 with 10,000 permutations, an alpha value of 0.01, and undo splits (undo.sd=1) (Olshen et al. (2004) Biostat 5:557-572; Venkatraman et al. (2007) Bioinformatics 23:657-663). Post-segmentation, an additional level of normalization that centers the segment values at 0 was applied.

Figure 2:
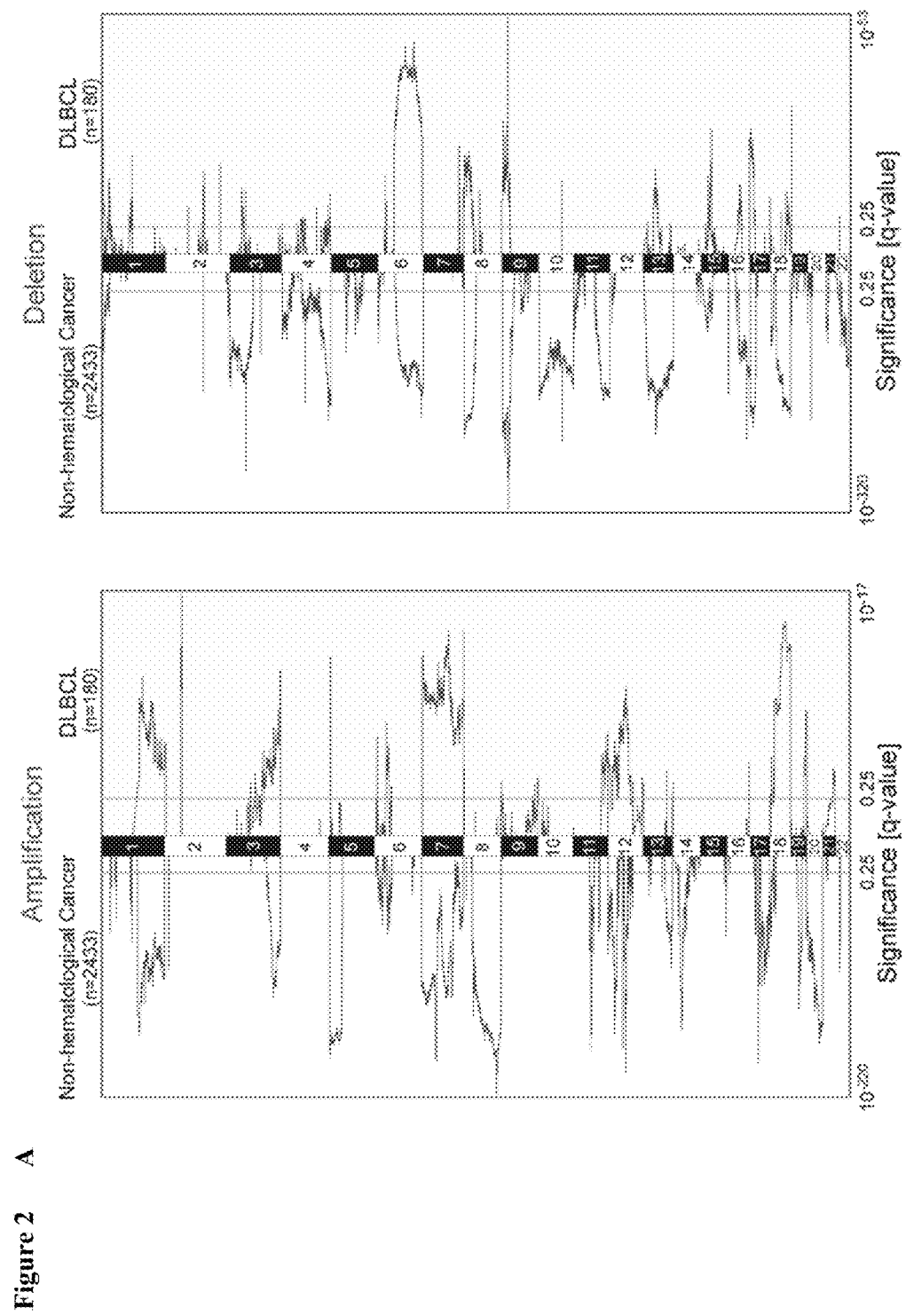
FIGS. 2A-2C show a comparison of CNAs in primary DLBCLs and non-hematologic cancers. The GISTIC-defined recurrent CNAs in the 180 primary DLBCLs (right) are compared to those in 2,433 non-hematologic cancers from a publicly available database (left.

Genomic Identification of Significant Targets in Cancer (GISTIC):

For the identification of significant regions of CN alteration, the standard GISTIC algorithm (Beroukhim et al. (2007) Proc Natl Acad Sci USA 104:20007-20012) was applied on the segmented data using the GISTIC GenePattern module. Standard GISTIC uses a low-level cutoff (determined by estimating the noise) to find significant variation corresponding to both broad low-level alterations and focal high-level alterations. The algorithm requires threshold parameters indicating the minimal copy-number variation sufficient to contribute to significance calculations. These parameters-one for amplification and one for deletion—are heuristically determined by analyzing a histogram of segment copy-numbers and finding the first valleys to the left and right of the central peak at 0, representing the noise level. The thresholds used in our final analysis were $t_{amp}$=2.46 for amplifications and $t_{del}$=1.62 for deletions (corresponding to $2^{x+1}$ for x—±0.3). All GISTIC runs were performed with cap-values (in $\log_2$-space) of ±1.5 (0.7 copies and 5.65 copies) on each sample (i.e., values above 1.5 were replaced with 1.5 and values below −1.5 were replaced with −1.5). These cap values were used to limit problems of hyper-segmentation that occur particularly in regions with extreme values due to different attenuation curves of adjacent probes. GISTIC reports peaks of interest with associated FDR q-values obtained by multiple hypotheses correction (Benjamini et al. (1995) J Royal Statistical Society Series B (Methodological) 57:289-300), which represent an upper bound on the expected fraction of false positives in the resulting list. Regions with q-values below 0.25 are considered significant and are reported. GISTIC also outputs the genes and micro-RNAs contained within these regions. Within each region, a peak (or peaks) is identified as the contiguous set (or sets) of loci with highest q-values. This is in general of smaller size than the region containing it. A total of 21 amplifications and 24 deletions were identified, with sizes varying from ~3 kb to ~4 Mb, with a median size of 280 Kb and 190 Kb for amplifications and deletions respectively. These alterations contained between 0 and 80 genes, with a median of 2 and 2 genes for amplifications and deletions respectively. Table 1 lists alterations in size and a set of genes falling within the peaks and the regions. FIG. 2 compares the GISTIC plots of the DLBCL series to a compendium of non-hematological solid tumors previously described (Beroukhim et al. (2007) Proc Natl Acad Sci USA 104:20007-20012).

Copy-Number Variants Removal:

Before applying the GISTIC analysis, genomic regions which are associated with copy-number variations (CNVs) are removed. This step is necessary to avoid significant GISTIC peaks which are due to copy-number variations that appear in large enough fractions of samples. A list of genomic regions of CNVs was compiled by combining several sources. The combined list was used in all of the GISTIC runs. The sources for CNV regions were: 1. CNVs found in a SNP6.0 analysis of all HapMap normals (McCarroll et al. (2008) Nat Genet 40:1166-1174); 2. CNVs identified in at least two independent publications listed in the Database of Genomic Variants (DGV, available on the World Wide Web at projects.tcag.ca/variation, version 3) (Conrad, B. (2004) Immunogenetics 56:220-224; Conrad et al. (2006) Nat Genet 38:75-81; Hinds et al. (2006) Nat Genet 38:82-85; Iafrate et al. (2004) Nat Genet 36:949-951; Locke et al. (2006) Am J Hum Genet 79:275-290; McCarroll et al. (2006) Nat Genet 38:86; Redon et al. (2006) Nature 444: 444-454; Sebat et al. (2004) Science 305:525-528; Sharp et al. (2005) Am J Hum Genet 77:78-88; and Tuzun et al. (2005) Nat Genet 37:727-732); 3. CNVs found in the profiled normal samples by an automated search; and 4. CNVs found in the TCGA normal samples included in the normalization step.

Comparison with Solid Tumors:

The set of CN alterations identified in the DLBCL cohort was compared to the alterations identified in a large compendium of 2433 solid tumors extracted from the global cancer map (GCM) (Beroukhim et al. (2010) Nature 463: 899-905). GISTIC analysis was performed on this set, and alterations in the two sets were compared as illustrated in FIG. 2 and Table 2.

D. Integrative Analysis

Integrative analysis of copy-number and gene expression data was carried out to further prune the list of candidate genes within alteration regions, as well as to assess whether the identified CN alterations induce significant expression changes. In particular, the association between copy-number levels and gene expression for all the genes both within (cis-acting) and outside (trans-acting) the alteration peaks or regions was assessed. Operationally, this translated into carrying out as many differential analyses as the number of identified alterations.

Cis-Acting Alteration Signatures:

The genes within the peak (region) of each GISTIC-identified alteration were tested for an association between their expression (transcript abundance) and the presence/absence of the harboring alteration by a two-group t-statistic with unequal variance. To this end, for each gene/transcript, a two-group t-score with unequal variance was used to assess the difference in expression levels between the groups of samples with and without the alteration. Nominal p-values were computed by permutation test as well as based on asymptotic theory (by means of the Student's t-distribution), and MHT-corrected q-values were derived by the FDR procedure. The MHT correction was computed by taking the union of all the genes within all the peaks (regions). The cis-acting alteration signature for a given alteration was then defined as the set of within-peak (-region) transcripts with FDR (asymptotic or permuted) q-values≤0.25.

Trans-Acting Alteration Signatures:

The transcripts from genes which were outside an alteration peak were also evaluated for an association between their expression and the respective copy number alteration. The top 6,000 transcripts ranked by across-sample median absolute deviation (MAD) were used as the candidate list. The trans-acting alteration signature for an alteration was defined as the set of outside-peak transcripts with FDR q-values ≤0.25 and fold change ≥1.3.

Enrichment Analysis:

The GISTIC-identified copy-number alterations were tested for enrichment of relevant biological categories both across genes (by pathway/geneset enrichment test) and across samples (by phenotype enrichment test).

Pathway and Geneset Enrichment Analysis:

For the annotation of the alteration peaks (regions), enrichment analysis based on the hyper-geometric distribution was carried out. In particular, a global alteration signature was defined and tested for enrichment with respect to a compendium of genesets from the MSigDB repository (Subramanian et al. (2005) PNAS 102:15545-15550). Two global alteration signatures were defined and tested: (1) The global cis-acting signature, defined as the set union of all the cis-acting alteration signatures (q≤0.25), was tested for enrichment against the list of 639 genesets representing canonical pathways (CP) in the C2 collection of MSigDB, version 2.5 and (2) The global cis-/trans-acting signature, defined as the set union of all the cis-acting (q≤0.25) and trans-acting (q≤0.05) alteration signatures, was tested for enrichment against the list of 615 genesets representing transcription factors' targets in the C3 collection of MSigDB version 2.5. Nominal p-values based on the hyper-geometric distribution were computed for all genesets. In particular, given a background population P of N genes, a geneset G ($\subseteq$P) of m genes, and a signature S ($\subseteq$P) of n genes, with an overlap of k genes between geneset G and signature S, with 0≤k≤min(n,m), the enrichment p-value is given by the probability of observing an overlap of k or more genes under the null hypothesis that the signature S is drawn at random from the background population P. It is computed based on the hyper-geometric distribution function as follows:

$$P(x \geq k \mid H_0) = \sum_{x=k}^{min(m,n)} \frac{\binom{m}{x}\binom{N-m}{n-x}}{\binom{N}{n}}.$$

A background population of N=18,590 genes, corresponding to the set of refSeq annotated genes in HG18 was used. MHT-corrected q-values were derived from the nominal p-values using the entire list of genesets as the number of hypotheses tested (639 hypotheses and 615 hypotheses for the cis-acting and cis-/trans-acting signatures respectively). Hierarchical clustering of cell cycle regulating SCNAs revealed a clear two-class structure that partitions the series into a 'complex' and a 'clean' phenotype as measured by the number of co-occuring alterations. To test for enrichment of a publicly available RB1 signature (Knudsen et al. (2008) Nat Rev Cancer 8:714-724), gene set enrichment analyses (GSEA) were performed with respect to the "complex vs. clean" phenotype. The permutation-based p-value was computed by controlling for the confounding batch effect of the two gene expression cohorts.

Phenotype Enrichment:

The exact Fisher test was used to test for association between copy number alterations and two gene expression-defined phenotypes: the Cell-of-Origin (COO) phenotype (Alizadeh et al. (2000) Nature 4051:503-511) and the CCC phenotype (Monti et al. (2005) Blood 105:1851-1861). Table 1 summarizes the results and reports both nominal p-values and MHT-corrected q-values, with the correction accounting for the total number of alterations (n=19 amp+ 26del=45) and the total number of phenotypes (n=3) tested. Outcome data regarding progression and overall survival was collected and tested separately for patients treated with a non-Rituxan® (rituximab) or Rituxan® (rituximab) containing anthracycline-based polychemotherapy and differences in overall survival were tested using the logrank test (Kalbfleisch and Prentice. The statistical analysis of failure time data. Wiley Publishers). Differences between the ordered categories of the full IPI were assessed using the exact version of the Kruskal-Wallis test (Dawson-Saunders et al. (1994) In Basic and Clinical Biostatistics (Appleton & Lange: Norwalk, Conn.)) in 68 patients (24 low, 17 low/intermediate, 15 high/intermediate, and 12 high risk). A Cox-proporational hazard (CPH) model was used to test whether the "complex vs. clean" phenotype had predictive power independent of the IPI index. To this end, a likelihood ratio test (LRT) was computed to compare i) the CPH model fitted on the IPI index and the "complex vs. clean" phenotype with ii) the CPH model fitted on the IPI index only. The p-value of the LRT score was computed based on a chi-square distribution with one degree of freedom.

Global View of Copy Number Alterations:

To visualize the distribution of alterations across samples, a matrix with each entry indicating the presence/absence of an alteration (row) in a given sample (column) was created. Color-coded versions of the full and selected matrices in FIGS. 6 and 5A, respectively. Specifically, copy-number alterations were organized by pathway and by chromosomal location across samples to assess whether global alteration patterns would emerge. To this end, alteration-based matrices were defined, with each entry in a matrix indicating the presence/absence of an alteration in a given sample at a given alteration locus. The presence/absence of an alteration was established based on the thresholds $t_{amp}$ and $t_{del}$ used in the GISTIC analysis, with an alteration considered amplified (deleted) in a given sample if the average values of the SNP probesets and CN probes falling within the alteration boundaries was above $t_{amp}$ (below $t_{del}$) in that sample. The alteration-based matrix is a sample-by-alteration binary matrix listing the entire set of significant alterations detected by GISTIC analysis. A color-coded version of this matrix is shown in FIG. 6 and from selected alterations in FIG. 8A, with rows/samples and columns/alterations clustered by hierarchical clustering based on Euclidean distance and the Ward agglomeration method (Gentleman et al. (1997). The R Project for Statistical Computing; Ward, J. H. (1963) JASA 58:236-244). The legend, containing GEP-defined phenotypes, p53 mutations, BCL2 and BCL6 translocation status and the assignment to transcriptional defined CCC or COO class was plotted using GEN-E (available on the World Wide Web at broadinstitute.org/cancer/software/GENE-E/).

While clustering and classification were based on the binary matrix only listing the presence/absence of alterations, the color coding was based on a three-valued (0-2) matrix distinguishing between low-level (1-copy) and high-level (2-copy or higher) gains and losses. Low-level alteration thresholds were (in log 2(x)-1 space) tlow-amp=0.3 and tlow-del=-0.3, and high-level alteration thresholds were thigh-amp=0.9 and thigh-del=-0.9.

Figure 5:
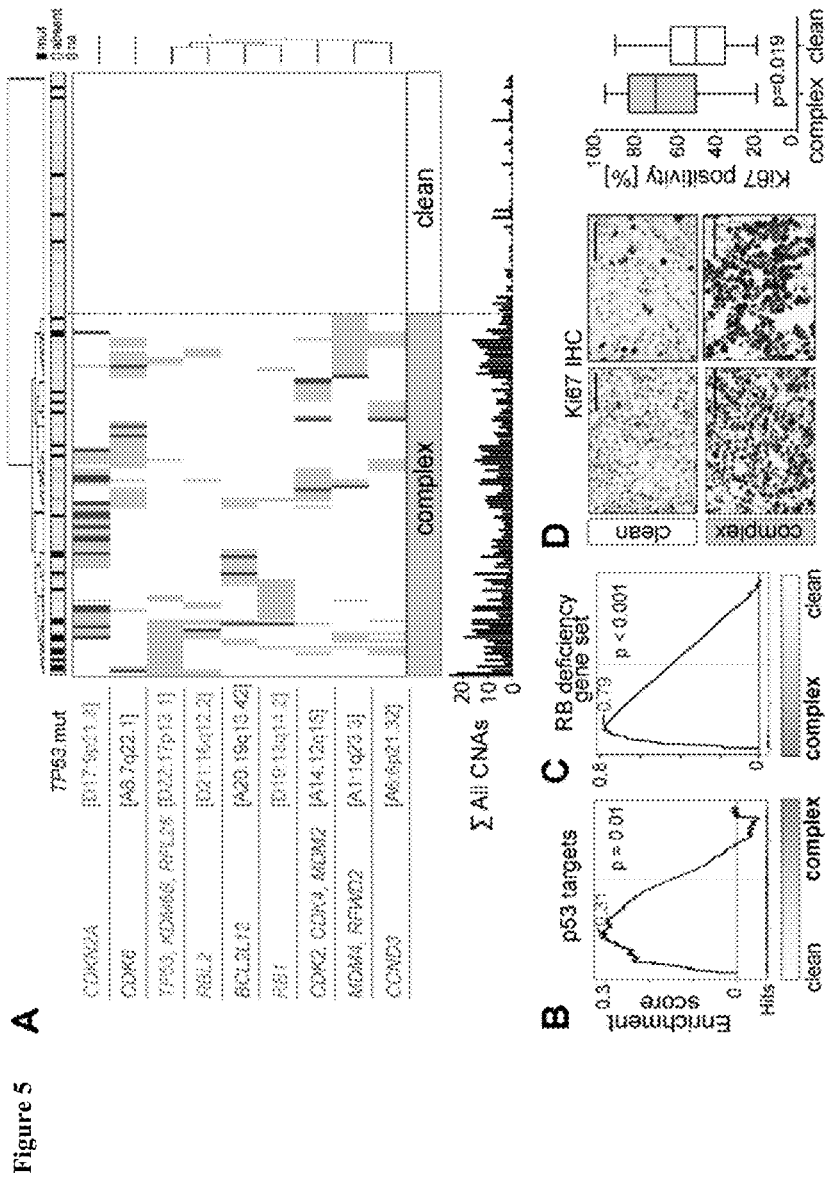
FIGS. 5A-5F show CNAs of p53 pathway and cell cycle components in individual primary DLBCLs and association with outcome, as well as the prognostic significance of "complex" vs. "clean" CAN patterns in DLBCLs.
Figure 5:
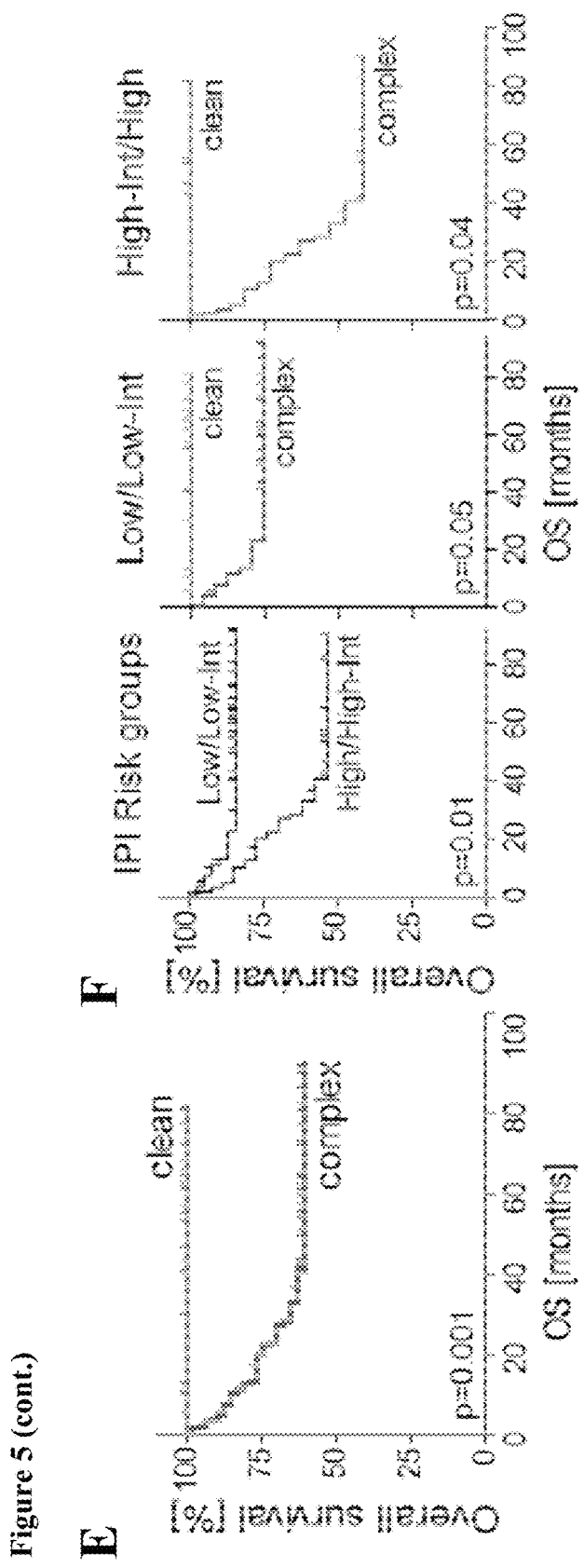
Figure 6:
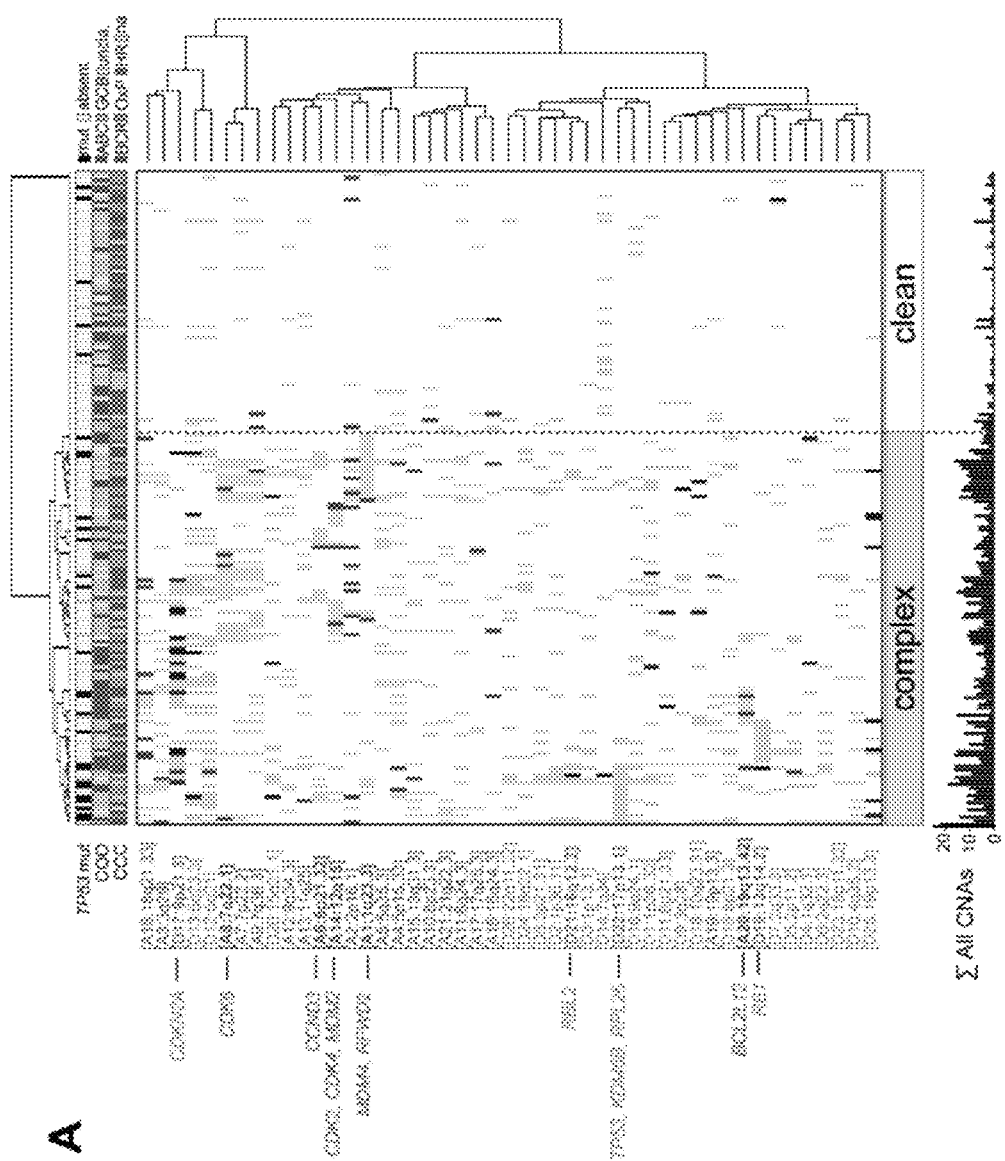
FIGS. 6A-6C show CNAs in a series of DLBCLs and an independent series and GSEA of p53 target genes.
Figure 6:
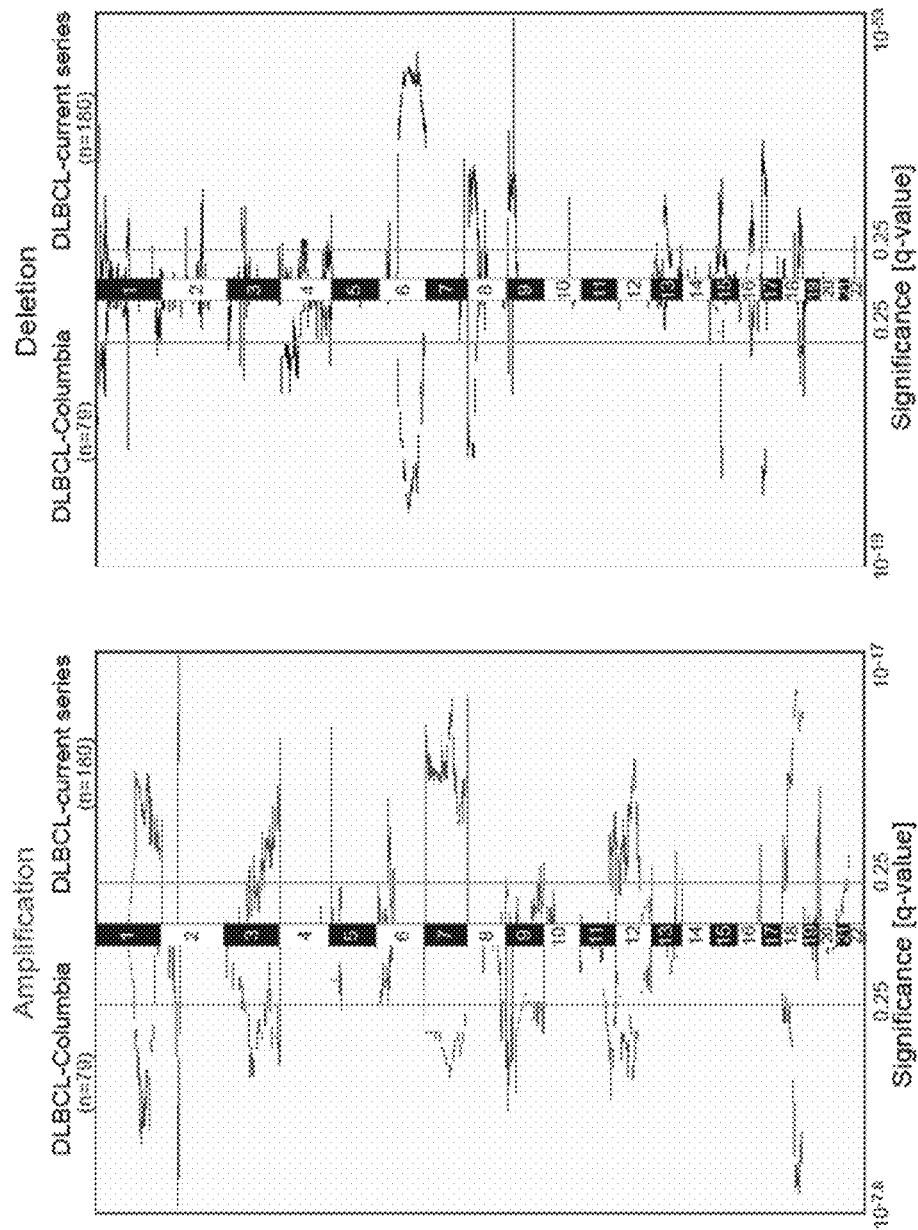
Figure 6:
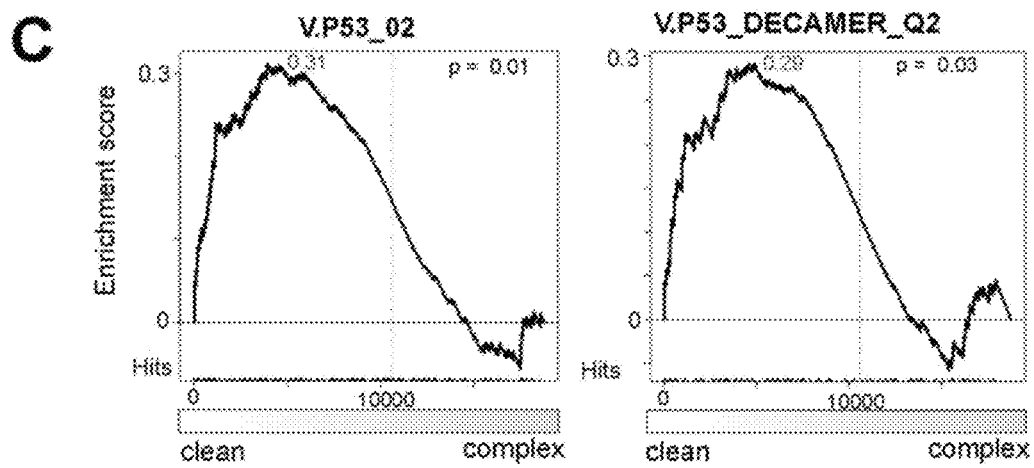

For the classification into the "clean" and "complex" groups, the simple rule of assigning samples with no (i.e., zero) alterations in the nine p53/cell cycle CNAs to the "clean" class, and samples with one or more alterations to the "complex" class was used (FIG. 5A).

Visualization of Custom Copy Number Alterations and GISTIC Plots:

The segmented copy number file and GISTIC plots were visualized for genes of interest using the "gene-centered-view" function in IGV 2.1 (Robinson et al. (2011) Nat Biotechnol 29:24-26).

The HD-SNP 6.0 and gene expression data are available through the Gene Expression omnibus, which is available on the world wide web at the ncbi.nlm.nih.gov/geo/ website under the accession number, GSE34171.

E. Direct Sanger Sequencing

For the TP53 mutation analysis in a subset of 87 primary DLBCLS, exons 5-9 including the exon-intron junctions splice sides were amplified by PCR using the tumor genomic DNA as template and standard conditions with the Phusion Hot Start High-Fidelity DNA-Polymerase (New England Biolabs, Ipswich) using the following primer pairs:

| Primer name | Sequence |
|---|---|
| Sequence-P53_Exon5/6_F (SEQ ID NO: 23) | 5'-ATC TGT TCA CTT GTG CCC TGA CT-3' |
| Sequence-P53_Exon5/6_R (SEQ ID NO: 24) | 5'-CCC TTA ACC CCT CCT CCC AGA GA-3' |
| Sequence-p53_E7_F (SEQ ID NO: 25) | 5'-CCT GCT TGC CAC AGG TCT CCC CAA-3' |
| Sequence-p53_E7_R (SEQ ID NO: 26) | 5'-CCC AGG GGT CAG AGG CAA GCA GA-3' |
| Sequence-p53_E89_F (SEQ ID NO: 27) | 5'-GCT CCA GAA AGG ACA AGG GTG GTT GGG-3' |
| Sequence-p53_E89_R (SEQ ID NO: 28) | 5'-GCA TCA CTG CCC CCT GAT GGC AAA TG-3' |

For all cases appropriate negative controls were run concordantly. PCR products were gel purified and subjected to direct Sanger sequencing with an automated sequencer from both ends using the same primers. Sequences were aligned to the reference sequence, NC_000017.9. TP53 mutation status for the cell lines was obtained by RT-PCR amplification from cDNA of all cell lines using the primers TP53_C out/TP53_N_out and appropriate negative controls.

After gel purification, the PCR products are sequenced for all base pairs from two sides using the primers TP53_C_in/TP53 N in and TP53_seq_1:

| Primer name | Sequence |
| --- | --- |
| Sequence-TP53_C_out (SEQ ID NO: 29) | 5'-GAC AAA GCA AAT GGA AGT CCTG-3' |
| Sequence-TP53_C_IN (SEQ ID NO: 30) | 5'-GCT GTC AGT GGG GAA CAA GA-3' |
| Sequence-TP53_seq_1 (SEQ ID NO: 31) | 5'-GCA GCT ACG GTT TCC GTC TG-3' |
| Sequence-TP53_N_out (SEQ ID NO: 32) | 5'-CTC AAG ACT GGC GCT AAA AGT T-3' |
| Sequence-TP53_N_IN (SEQ ID NO: 33) | 5'-CTG GAT GGA CAG CCA GAC TG-3' |

In the remaining 93 cases, the complete open reading frame was sequenced, including splice sites. Sequences were aligned to the reference NM_000546.4 and sequence variations were evaluated with the mutation validation tool available at IARC on the World Wide Web at p53.iarc.fr/MutationValidationCriteria.asp.

F. Tissue Microarray Construction and Ki67 Staining Protocol

Formalin-fixed paraffin embedded (FFPE) tissue biopsy samples corresponding to each frozen sample used for nucleic acid isolation were selected for construction of the tissue microarray (TMA). A hematoxylin and eosin stained section from each block was examined by two hematopathologists and regions of representative and viable diffuse large B-cell lymphoma circled. A technician then transferred 3×0.6 mm core punches from the annotated areas on the donor block to the recipient (TMA) block using a manual arrayer (Beecher Instruments Inc., Sun Prairie, Wis., USA). The final TMA contained 132 cores of tissue from 44 individual cases of DLBCL and an additional 12 cores of tissue from 4 control tonsils. Immunohistochemistry was performed using 5-μm-thick TMA sections. Slides were soaked in xylene, passed through graded alcohols, and put in distilled water. Slides were pretreated with DAKO retrieval solution (DAKO USA, Carpinteria, Calif.) in a steam pressure cooker (Biocare Decloaking Chamber CD2008US, Biocare Biomedical, Concord, Calif.) at manufacturer's recommended settings. All further steps were performed at room temperature in a hydrate chamber. The slides were blocked for endogenous peroxidase activity with peroxidase block (DAKO), washed 5 minutes in buffer, and followed by 20 minute incubation with serum free protein block (DAKO). The mouse anti-Ki67 (MIB-1) monoclonal antibody (DAKO, cat. M7240) was applied in DAKO diluent at 1:500 dilution for 1 hour. After washing, the antibody was detected using the mouse Envision kit (DAKO) and DAB and counterstained with Harris hematoxylin. Percent positivity per tumor cell was scored for each core. For further studies, the mean of three cores was computed for an individual case. Differential Ki67 expression between tumors based on copy number defined clusters were tested by a two-sided Mann Whitney test (Dawson-Saunders et al. (1994) In Basic and Clinical Biostatistics (Appleton & Lange: Norwalk, Conn.)).

G. Cell Lines and Cell Culture

The identities of the DLBCL cell lines used in this study were confirmed via STR profiling (PowerPlex®1.2 system [Promega]) and the online verification services of the cell banks JCRB and DSMZ (available on the World Wide Web at cellbank.nibio.go.jp/cellbank_e.html and dsmz.de/STRanalysis). All DLBCL cell lines were cultured at 37° C. in 5% C02. SU-DHL-6, SU-DHL-7, DB and Toledo were propagated in RPMI; OCI-Ly3, OCI-Ly18 and OCI-Ly19 were grown in IMDM. HEK293T cells for lentiviral production were cultured in DMEM. All media were supplemented with 10 mM HEPES buffer, 2 mM L-glutamine, 50 U/mL penicillin, 50 U/mL streptomycin and 10% heat-inactivated fetal calf serum (Invitrogen). To ensure that cells were in logarithmic growth phase, cells were diluted to 200,000 cells/ml 48 h prior to any experiment.

H. Cell Cycle Analysis

Cells were re-suspended in 1 ml of growth medium supplemented with 10 μg/ml Hoechst 33342 (Molecular Probes, Invitrogen) as final concentration. After 60 min at 37° C. in the dark. Analysis was performed on a FACS-CAriallu cytometer (BD Biosciences) using the UV laser 350 nm with 20 mW. The cell cycle was plotted as histogram after excluding doublets.

I. SDS-PAGE and Western Blot

For SDS-PAGE, total cell lysates were obtained using NP-40 lysis buffer (Tris-HCl 50 mM pH7.4, NaCl 150 mM, NaF 5 mM, EDTA 5 mM, 1% NP-40) supplemented with 1 mM activated $Na_3VO_4$ and complete proteinase inhibitor cocktail (Roche). Twenty milligrams of total protein lysates were separated on a SDS NuPage Novex 4-12% BisTris gradient gel, transferred to PVDF membrane (Millipore Corp. Bedford, Mass.), and blocked with 5% BSA (Sigma) in 0.1% Tween-20/tris-buffered-saline (TBS). After washing, membranes were probed against the indicated antigens following the manufacturer's recommendation. Polyclonal antibodies against phospho-$Ser^{780}$ RB (1:1000, #9307), and anti-rabbit IgG, HRP-linked secondary antibodies (1:2000, #7074 & #7076) were purchased from Cell Signaling Technologies (Danvers, Mass.). The anti phosho-$T^{821}$-RB1 antibody (1:1000, #44-582G) was purchased from Invitrogen. RB1 was detected using the monoclonal antibody from BD Biosciences (1:500, 554136; San Jose, Calif.). For chemoluminescence detection, enhanced ECL (GE Healthcare, Piscataway, N.J.) was used. After stripping, membranes were re-probed for GAPDH (1:3000, Santa Cruz Biotechnology) as loading control.

J. Assessment of Proliferation, Cell Cycle and Apoptosis Following Chemical CDK Inhibition The pan-CDK inhibitor, flavopiridol (Selleck Chemicals, Houston, USA), was suspended in DMSO (10 mM stock solution) and stored at −20° C. until use. Following treatment, proliferation of DLBCL cell lines was assessed with the alamarBlue assay (Invitrogen, Carlsbad, Calif.).

Cell cycle analysis was performed at 72 h using Hoechst 33342 (Supplemental Methods) and a FACSCAriaIIu cytometer (BD Biosciences) with a UV laser at 350 nm with 20 mW.

Cellular apoptosis was analyzed with an APC AnnexinV/ 7ADD Apoptosis Detection kit (BD Pharmingen). AnnexinV/7AAD plots and cell cycle graphics were generated using FlowJo software V7.6.1 for Windows (Tree Star).

K. In Vivo Studies

The DLBCL cell lines, Toledo, OCI-Ly1 and OCI-Ly4, were engineered for in vivo imaging by transduction with a VSV-G-pseudotyped lentivirus encoding the firefly luciferase, mCherry, and a puromycin-N-acetyltransferase, each separated by picornovirus ribosomal slippage peptides (Kimbrel et al. (2009) Mol. Imaging 8:140-147). The lentivirus was packaged by co-transfection of the lentiviral plasmid FUW-Luc-mCherry-puro (Kimbrel et al. (2009) Mol. Imaging 8:140-147) and the helper plasmids, pCMV-dR8.91 and pMD2.G-VSV-G into HEK293T cells using Fugene6® (Promega, Madison, Wis.), as previously described in (Moffat et al. (2006) Cell 124:1283-1298). Following transduction via spinoculation for 2 hr at 1000 g and 30° C. in the presence of 8 µg/ml polybrene (Sigma, St. Louis, Mo.) and selection with 2 µg/ml puromycin for 48 hr (Sigma, St. Louis, Mo.), luciferase activity and mCherry expression of the engineered Luc-mCherry lymphoma cells were documented. Subsequently, $5\times10^6$ viable Luc-mCherry lymphoma cells in 250 µl PBS were injected via the lateral tail veins of male, 8-week old NOD SCID Il2r$\gamma^{null}$ mice (Charles River Laboratories, Wilmington, Mass.).

Disease burden was quantified using bioluminescence imaging (IVIS Spectrum, Caliper Life Sciences) following intraperitoneal (IP) injection of 75 mg/kg d-luciferin (Promega, Madison, Wis.). Total body luminescence was quantified using the Living Image software package (Caliper Life Sciences) and expressed as photons per s per standardized region of interest (photons/s/ROI), encompassing the entire mouse. Data are presented as mean±SEM with statistical significance determined by Student's t-test.

Six days following tumor inoculation, animals with established disease documented by imaging were divided into two cohorts with equal mean bioluminescence and treated daily with 7.5 mg/kg flavopiridol (Selleck Chemicals, Houston, Tex.) or vehicle (10% DMSO in normal saline) IP. Following 12-15 days of treatment, the entire cohort was sacrificed and subjected to a complete hematologic analysis. Flow cytometry was used to analyze single cell suspensions of spleen and bone marrow for the presence of mCherry-positive lymphoma cells (excitation of 561 nm using a yellow-green laser on a BD LSRFortessa [BD Bioscience]), which were confirmed to co-express human CD45 and CD19 by flow cytometry with anti-human CD45-FITC (BD) and anti-human CD19-PE-Cy7 (BD) antibodies (FIG. 11D).

An independent cohort of mice was treated for 5 days with either 7.5 mg/kg flavopiridol or vehicle in order to assess the pharmacodynamic efficacy of flavopiridol treatment. Two hrs after the last dose, mice were euthanized and tissues fixed by intracardiac perfusion with 10% formalin. Spleens were harvested and subjected to further fixation overnight in 10% neutral-buffered formalin in preparation for immunohistochemical analyses (see IHC section). All animal studies were performed according to Dana-Farber Cancer Institute Institutional Animal Care and Use Committee (IACUC)-approved protocols.

Immunohistochemistry of mouse tissues was performed using 4 µm thick formalin-fixed, paraffin-embedded tissue sections. Briefly, slides were soaked in xylene, passed through graded alcohols and put in distilled water. Slides were then either pre-treated with 1.0 mM EDTA pH 8.0 (Zymed, South San Francisco, Calif.) or citrate buffer pH 6.0 or DAKO retrieval solution (DAKO USA, Carpinteria, Calif.) in a steam pressure cooker (Decloaking Chamber, BioCare Medical, Walnut Creek, Calif.) as per manufacturer's instructions followed by washing in distilled water. All further steps were performed at room temperature in a hydrated chamber. Slides were pre-treated with Peroxidase Block (DAKO) for 5 min to quench endogenous peroxidase activity. Primary antibodies were applied in DAKO diluent for 1 hr. Slides were washed in 50-mM Tris-C1, pH 7.4, and detected with anti-mouse or anti-rabbit Envision+ kit (DAKO) as per manufacturer's instructions. After further washing, immunoperoxidase staining was developed using a DAB chromogen (DAKO) and counterstained with hematoxylin.

For immunohistochemical studies, fixed tissues were subjected to staining of Ki67 (1:250, EDTA, Vector labs cat. #VP-RM04) as proliferation marker and human CD20 (Ready-to-use, DAKO retrieval solution cat. # S1700, clone L26, cat.#N1502).

All animal studies were performed according to Dana-Farber Cancer Institute Institutional Animal Care and Use Committee (IACUC)-approved protocols.

Example 2: Recurrent Copy Number Alterations Mapped in Primary DLBCL

Figure 1:
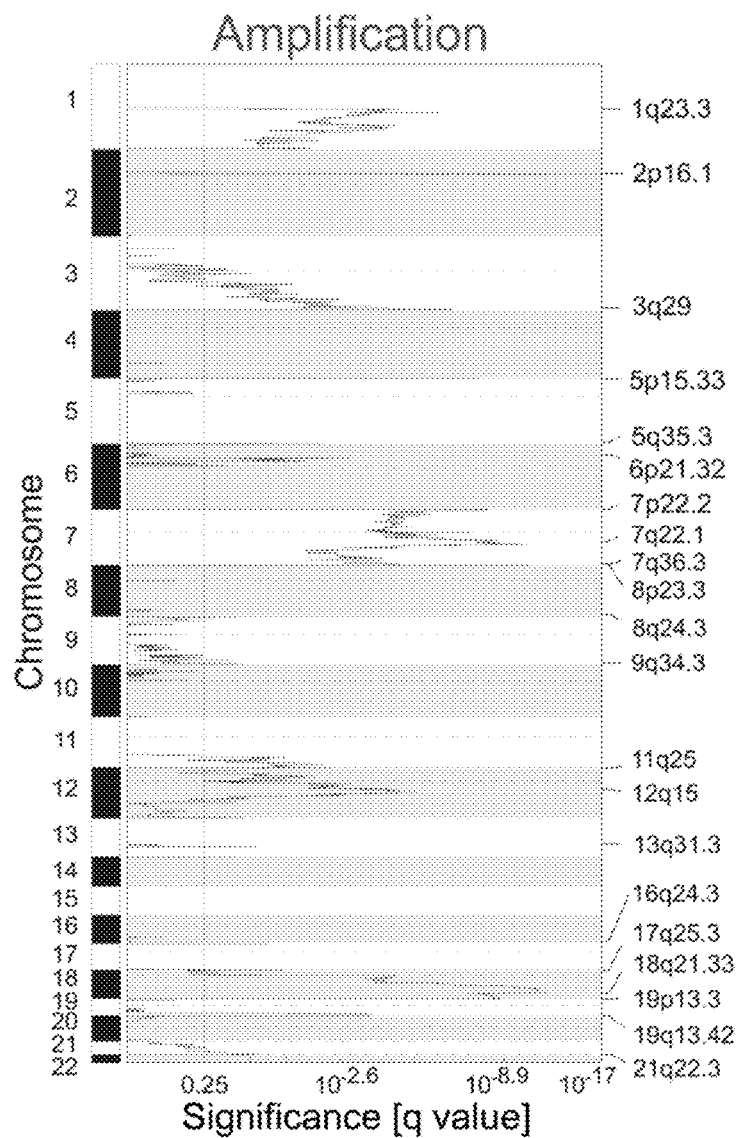
FIG. 1 shows recurrent copy number aberrations (CNAs) in newly diagnosed DLBCLs. GISTIC summary plots of the significant copy number (CN) gains (left panel) and CN losses (right panel) in 180 primary DLBCLs are displayed by chromosomal position (y-axis). False discovery rate (FDR) q values of <0.25 (to the right of the line, x-axis) were considered statistically significant. The chromosomal bands, GISTIC peak boundaries, frequencies of alterations (n [%]) and top 5 genes by integrative analyses of CN and transcript abundance are listed below. The full list of such criteria is provided in Table 1.
Figure 1:
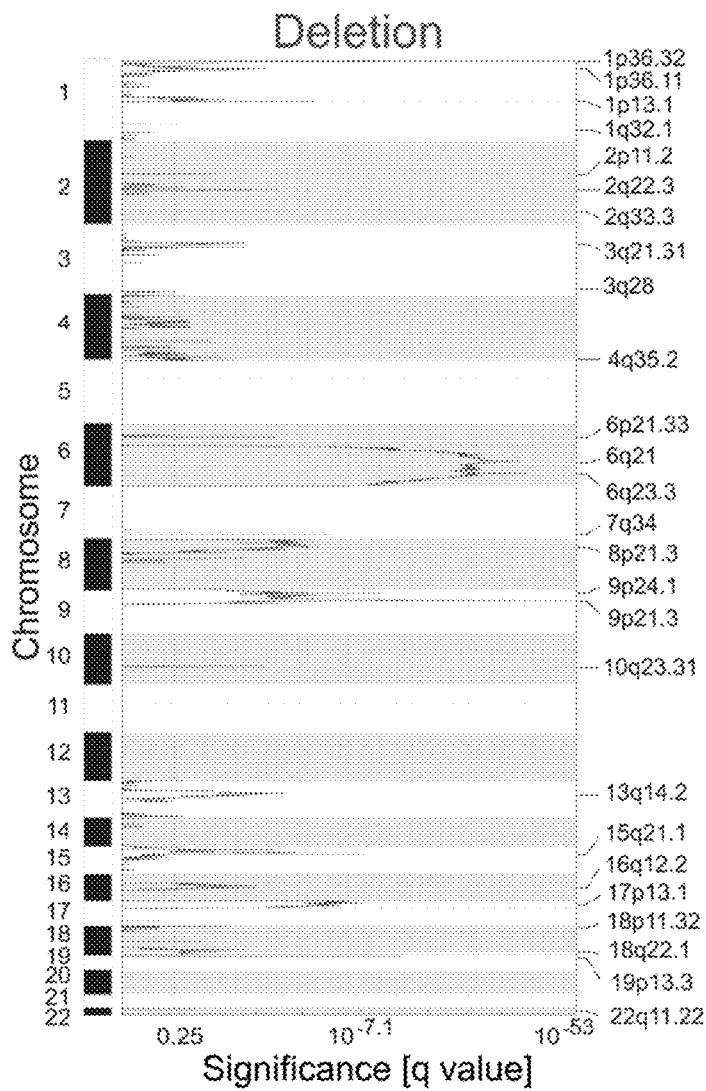

Recurrent CNAs in the 180 primary DLBCLs were detected using the GISTIC (Genomic Identification of Significant Targets in Cancer) algorithm. Within the identified regions of significant copy number (CN) gain or loss, narrower peaks of maximally significant CN change were identified. Forty-seven recurrent CNAs, including 21 copy gains and 26 copy losses, with frequencies of 4% to 27%, were identified (FIG. 1 and Table 1). The GISTIC-defined CNAs range from narrow focal alterations, such as amplification peak 2p16.1 to chromosome arm and whole-chromosome alterations, including gain of 1 q, loss of 6 q and gain of chromosome 7 (FIG. 1).

Example 3: Comparison of CNAs in DLBCLs and Non-Hematological Cancers

To distinguish between CNAs that are unique to DLBCL and those that are found in other tumors, the DLBCL GISTIC analysis results were compared to that of 2,433 non-hematological cancers (Beroukhim et al. (2010) Nature 463:899-905). The CNAs in DLBCLs and the non-hematologic cancers were visualized with a mirror plot (FIG. 2A) and the CNA overlap in the two series was computed (Table 2). Seven of 21 (33%) regions of copy gain and 16/26 (62%) regions of copy loss were common to both series. Additional regions of copy gain exhibited partial overlap (FIG. 2B and Table 2). Examples of shared alterations include gains of chromosome 7 and chromosome 1 q and loss of chromosome 6 q, indicating a broader role for these alterations in multiple tumor types. In contrast, 9/21 (43%) regions of copy gain and 10/26 (38%) regions of copy loss were only identified in DLBCL, including gains of 2p16.1 and 19q13.42 (FIG. 2B and Table 2). These DLBCL-selective CNAs were largely absent in a lymphoid malignancy of non-GC origin (FIG. 2C).

Example 4: Integrative Analysis of CNAs and Transcript Abundance

It was anticipated that DLBCL CNAs would alter the corresponding gene transcript levels and prioritized genes with the most significant association between transcript abundance and CNA. All genes within the 47 defined CNA peaks and regions (Table 3) were analyzed for the association between transcript abundance and the presence/absence of the gene alteration (peak or region) across the DLBCL series. The "cis-signature" of a given CNA was defined as the set of within-peak (or within-region) genes with the most significant association between CN and transcript abundance (FDR q-values ≤0.25). The top 5 peak transcripts are shown in FIG. 1 and Table 1. The complete list is shown in Table 4. Finally, summary statistics are shown in Table 5.

Example 5: CNAs of Genes with Known Roles in Lymphomagenesis

The two genes most closely associated with the 6q21 and 6q23.3 copy loss were PRDM1 (BLIMP1) and TNFAIP3 (A20), respectively (FIG. 1 and Table 4). Both genes are tumor suppressors that can be inactivated by several mechanisms, including copy loss (Calado et al. (2010) Cancer Cell 18:580-589; Compagno et al. (2009) Nature 459:717-722; Kato et al. (2009) Nature 459:712-716; and Pasqualucci et al. (2006) J Exp Med 203:311-317). Deletion of the ubiquitin-editing enzyme, TNFAIP3, contributes to lymphoid transformation, in part, by deregulating NFκB signaling (Shembade et al. (2010) Science 327:1135-1139). Inactivation of the PRDM1 transcriptional repressor promotes lymphomagenesis by blocking normal plasma cell differentiation (Mandelbaum et al. (2010) Cancer Cell 18:568-579 and Pasqualucci et al. (2006) J Exp Med 203:311-317).

The additional tumor suppressor genes, CDKN2A, RB1, FAS and TP53, were closely associated with 9p21.3, 13q14.2, 10q23.31 and 17p13.1 copy loss, respectively (FIG. 1), consistent with earlier analyses (Jardin et al. (2010) Blood 116:1092-1104 and Sanchez-Beato et al. (2003) Blood 101:1220-1235). Furthermore, two well-known oncogenes were tightly linked with amplification peaks, REL at 2p16.1 and BCL2 at 18q21.33 (FIG. 1). Copy gains of 2p16.1/REL and 12q15 were more frequent in GCB DLBCLs, whereas gains of 18q21.32/BCL2 and 19q13.42 were more common in ABC tumors (see Tables 1 and 6; Bea et al. (2005) Blood 106:3183-3190 and Lenz et al. (2008) Proc Natl Acad Sci USA 105(36):13520-13525).

Example 6: CNAs of Newly Identified Genes in DLBCL

The genes most closely associated with amplification of 1q23.3 (seen in 15% of DLBCLs) encode the low-affinity receptors for the IgG Fc receptors, FCGR2B (CD32B) and FCGR2C, and the related protein, FCRLA (FCRL1) (FIG. 1). Increased FCGR2B expression was previously associated with adverse outcome in DLBCL (Camilleri-Broet et al. (2004) Br J Haematol 124:55-62) and FCGR2C copy number variation and overexpression was linked with certain autoimmune diseases (Breunis et al. (2008) Blood 111:1029-1038). In addition, FCRLA was preferentially expressed in B cells and postulated to be an activating co-receptor (Leu et al. (2005) Blood 105:1121-1126).

Genes associated with amplification of the 19q13.42 region include PRMT1 (protein arginine methyl tranferase 1) and BCL2L12 (Table 1). PRMT1 specifically dimethylates histone H4 at arginine 3 which generally serves as an activation signal (Nicholson et al. (2009) Pharmacol Res 60:466-474). In addition, PRMT1 modifies transcription factors including FOXO1 (Yamagata et al. (2008) Mol Cell 32:221-231) and signaling intermediaries such as the Igα subunit of the B-cell receptor (Infantino et al. (2010) J Exp Med 207:711-719). BCL2L12 is an atypical BCL2 family member with cytoplasmic and nuclear roles that are best characterized in glioblastoma multiforme (Stegh et al. (2011) Cell Cycle 10:33-38). Cytoplasmic BCL2L12 inhibits caspases 3 and 7 whereas nuclear BCL2L12 interacts with p53 and inhibits its binding to target gene promoters (Stegh et al. (2011) Cell Cycle 10:33-38).

Example 7: CNAs of Genes Required for Tumor Immune Recognition

In addition to identifying individual genes targeted by specific CNAs, several alterations that perturbed genes required for tumor immune recognition were identified. Copy loss of 6q21.33 decreased the abundance of the MHC class I molecules, HLA-B and HLA-C, at the peak and the MHC class I polypeptide-related sequences A and B, MICA and MICB, in the region (FIG. 1 and Table 1). In addition, copy loss of 15q21.1 and 1p13.1 reduced the abundance of the peak β2 microglobulin (β2M) and CD58 transcripts, respectively (FIG. 1). Copy loss of 19p13.3 decreased the levels of the region TNFSF9 (CD137L) transcripts (Table 1).

The β2M polypeptide associates with HLA class I heavy chains on the cell surface to present antigen. In the absence of β2M, stable antigen-HLA class I complexes cannot be formed. Both HLA class I and B2M copy loss were previously described in large B-cell lymphomas of immunoprivileged sites (Booman et al. (2008) J Pathol 216:209-217 and Jordanov et al. (2003) Int J Cancer 103:393-398) and inactivating mutations and deletions of B2M were recently reported in DLBCLs (Pasqualucci et al. (2011) Nature Genetics 43:830-837).

The 6q21.33 region genes, MICA and MICB (Table 1), encode ligands of the activating NKG2D receptor, which is expressed by NK cells and a subset of T cells (Raulet, 2003). Decreased expression of these NKG2D ligands likely limits an innate NK-cell mediated anti-tumor immune response. To our knowledge, this is the first description of MICA or MICB copy loss in DLBCL. However, MICA deletion was recently associated with an increased risk for the development of nasopharyngeal carcinoma (Tse et al., 2011) suggesting a more general role for these ligands in tumor immune evasion.

The 1p131 peak gene, CD58 (LFA3) (FIG. 1), encodes a member of the immunoglobulin superfamily that is a ligand for the co-stimulatory CD2 receptor on T and NK cells (Davis et al. (1996) Science 273:1241-1242). CD58 was recently reported to be the target of inactivating somatic mutations in a small subset of DLBCLs (Challa-Malladi et al. (2011) Cancer Cell 20:728-740 and Pasqualucci et al. (2011) Nature Genetics 43:830-837), providing additional evidence that CD58 loss promotes tumor immune escape.

The 19p13.3 region gene, TNFSF9 (Table 1), encodes the ligand for the CD137 costimulatory receptor which is expressed by follicular dendritic cells (FDC) and primed CD8+ memory T cells (Middendrop et al. (2009) Blood 114:2280-2289). Recent studies suggest that interactions between TNFSF9 on GC B cells and CD137 on FDC and T cells regulate the GC B-cell response and TNFSF9 loss promotes the development of GCB lymphomas (Middendrop et al. (2009) Blood 114:2280-2289).

Figure 3:
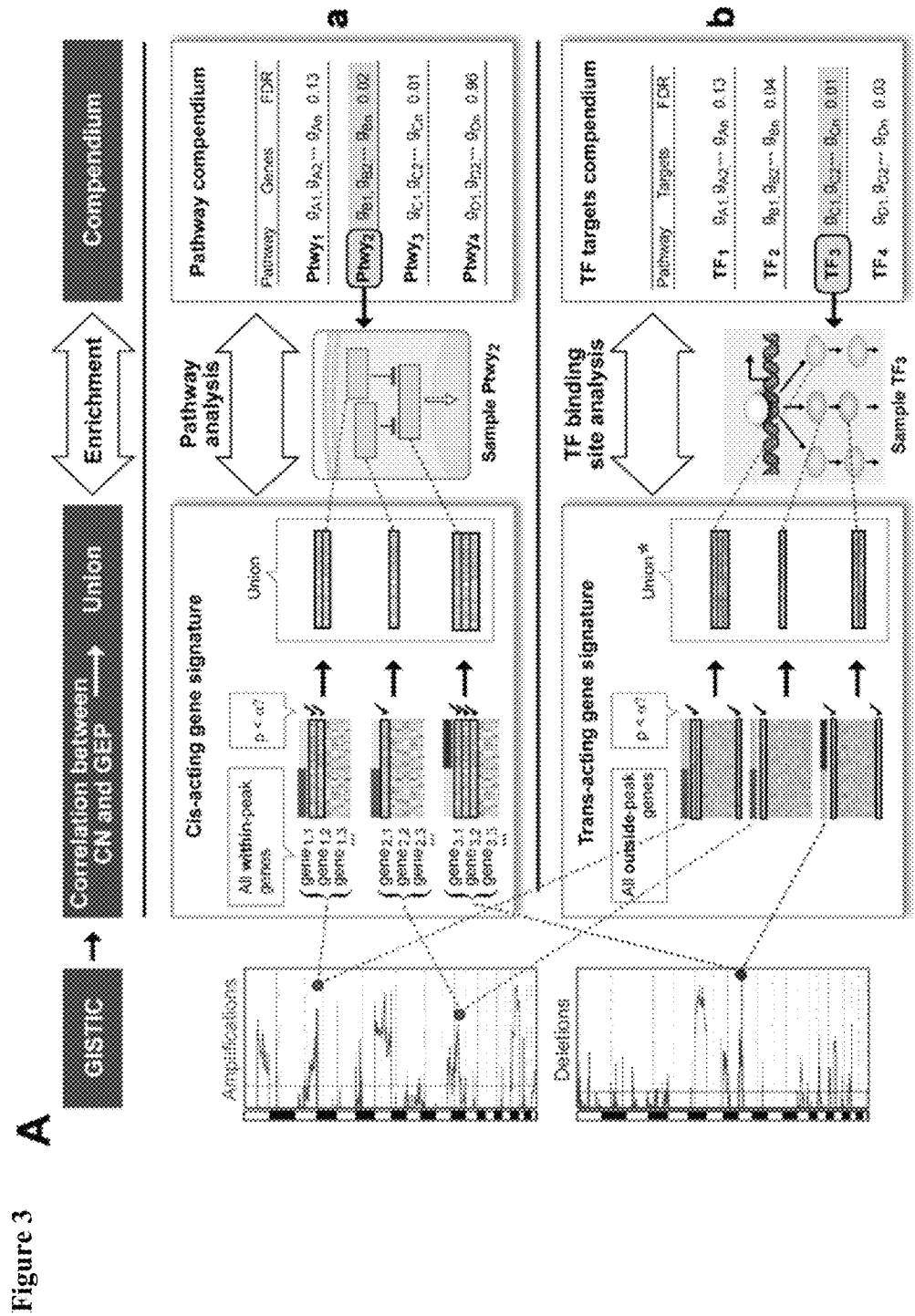
FIGS. 3A-3C show pathway and transcription factor (TF) binding site enrichment.

Example 8: Pathway Enrichment Analyses Reveal Coordinate Deregulation of p53 Signaling and Cell Cycle After identifying CNAs of several genes required for tumor immune recognition, a more comprehensive method to characterize additional pathways perturbed by CNAs in DLBCL was sought. First, global cis-acting peak or region signatures as the union of all individual cis-acting peak or region signatures were defined (Table 5 and FIG. 3A). Thereafter, pathway enrichment of the global signatures was performed using a curated series of gene sets and ranked the results by FDR (FIGS. 3A and 3B, top pathways; Table 7 provides the full analysis). In the global peak signature, 13 of 15 of the most significantly enriched gene sets reflect related aspects of p53 signaling, apoptosis and cell cycle regulation (FIG. 3B, top panel, FDR<0.10). Although the gene sets have different names, they include common genes that are targeted by CNAs—TP53, CDKN2A, RB1 and RBL2 (all copy loss) and BCL2 (copy gain) (FIG. 3B, top panel).

In the global region signature, the most significantly enriched gene set is the "p53 signaling pathway" (FIG. 3B, bottom panel, FDR 0.0003). Additional p53 pathway components altered by CNAs include the p53 modifiers, MDM2, MDM4, RFWD2 (COP1) (all copy gain); p53 targets, PERP, SCOTIN, TNFRSF10 (DR5/TRAIL receptor) and FAS (all copy loss); and critical cell cycle regulators, CCND3 (cyclin D3), CDK4, CDK6 and CDK2 (all copy gain) (FIG. 3B, bottom panel).

Figure 4:
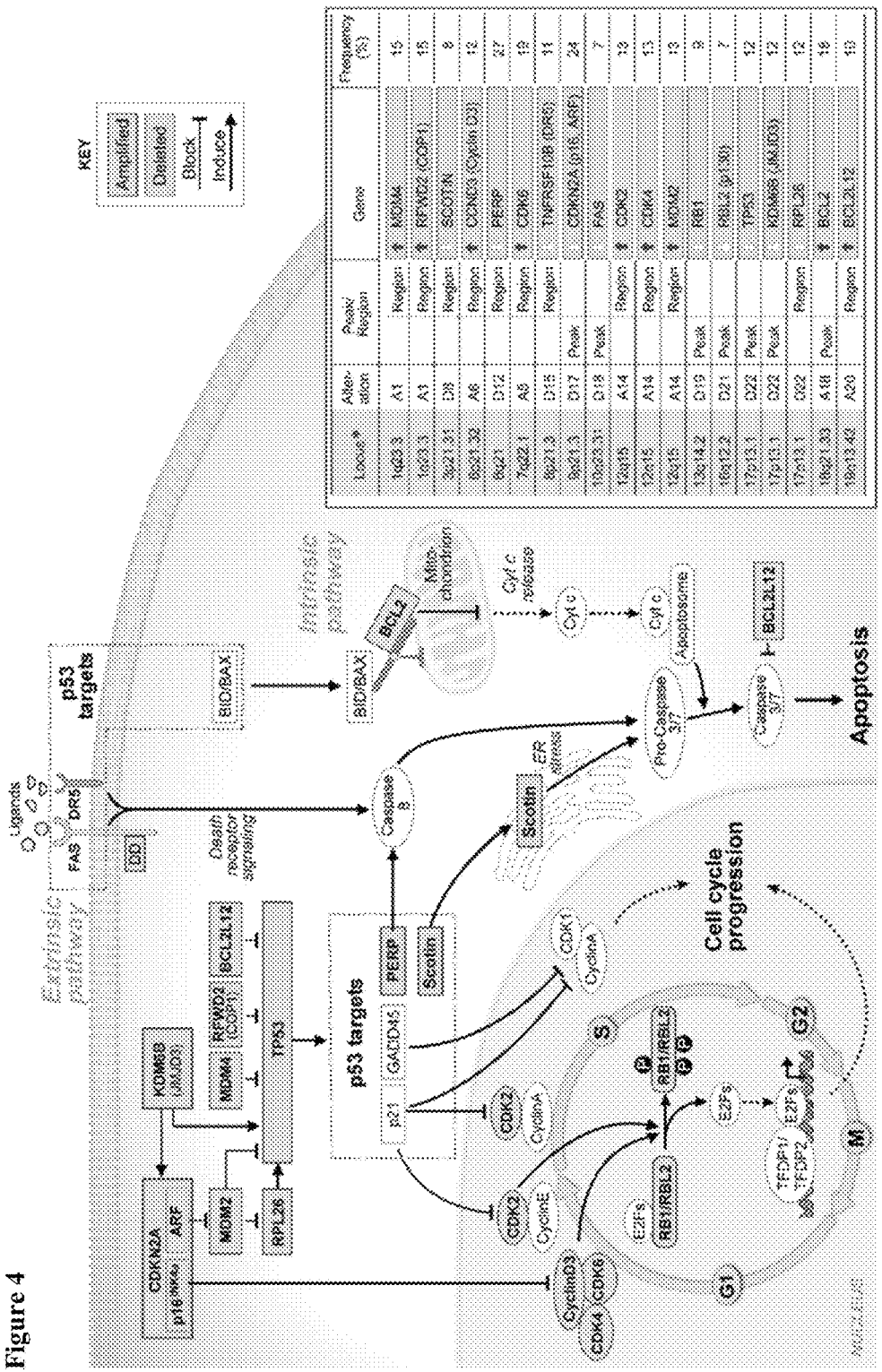
FIG. 4 shows components of the p53, apoptotic and cell cycle pathways perturbed by CNAs. Components include genes identified by the cis-signature pathway enrichment (FIG. 3B) and three p53 modifiers and cis-signature genes, RPL26, KDM6B/JMJD3 and BCL2L12, that are not captured by the current annotated gene sets. Amplified genes are shown in light shading (up arrows). Deleted genes are shown in dark shading (down arrows). For each CNA, the locus, peak or region gene and frequency of alteration are noted (right).

Example 9: Components of the p53, Apoptotic and Cell Cycle Pathways Perturbed by CNAs CNAs of p53, apoptotic and cell cycle pathway members are illustrated in FIG. 4.

The p53 Pathway:

CNAs of p53 pathway components all had the same predicted downstream effect of a decreased abundance of functional p53 and reduced levels of associated p53 targets. Copy loss of CDKN2A, at 9p21.3, occurs in 24% of DLBCLs (FIG. 4). The two alternative transcripts derived from the CDKN2A locus, p16$^{INK4A}$ and ARF, have complementary roles in p53 signaling and cell cycle regulation. ARF interferes with binding of the MDM2 E3 ligase to p53, decreasing its ubiquitylation and proteasomal degradation (Brooks et al. (2006) Mol Cell 21:307-315). As a consequence, CDKNA2 deletion (ARF loss) and MDM2 (12q15) amplification both increase the ubiquitylation and subsequent degradation of p53 (FIG. 4). Two additional E3 ligases with complementary but largely non-overlapping functions in destabilizing cellular p53 levels, MDM4 and RFWD2 (COP1), are increased by 1q23.3 copy gain (FIG. 4; Dornan et al. (2004) Cancer Res 64:7226-7230). Moreover, TP53 itself and two positive p53 modifiers, RPL26 and KDM6B (JMJD3), are targeted by 17p13.1 copy loss (FIG. 4). The H3K27 demethylase, KDM6B, participates in the active removal of the repressive methyl mark from p16$^{INK4A}$-ARF, contributing to its transcriptional activation (Agger et al. (2009) Genes Dev. 23:1171-1176). Therefore, KDM6B copy loss represents an additional mechanism of indirectly reducing functional p53 activity (FIG. 4). KDM6B also directly modulates p53 methylation, cellular distribution and function (Sola et al. (2011) PloS 6:1-10). The other positive modifier of p53 activity, RPL26, binds to the 5' UTR of TP53, promotes its translation and significantly increases stress-induced p53 levels (FIG. 4; Chen et al. (2010) Genes Dev 24:2146-2156 and Takagi et al. (2005) Cell 123:49-63). RPL26 is also a target of MDM2 which polyubiquitylates the ribosomal protein and enhances its proteasomal degradation (FIG. 4; Ofir-Rosenfeld et al. (2008) Mol Cell 32:180-189). In addition, the recently identified negative modulator of p53 transcriptional activity, BCL2L12 (at 19q13.42), is amplified in a subset of DLBCLs (FIG. 4).

Apoptotic Pathways:

Independent of its role in regulating p53, BCL2L12 amplification limits apoptosis by blocking the effector caspases 3 and 7 (FIG. 4). An additional means of perturbing the intrinsic apoptotic pathway is BCL2 copy gain (18q21.33) (FIG. 4). Copy loss also decreases the abundance of several p53 targets that promote apoptosis, including the extrinsic apoptotic pathway components, FAS, TNFRF10B, SCOTIN and PERP (FIG. 4; Beaudry et al. (2010) PLoS Genet. 6:e1001168; Bourdon, et al. (2002) J Cell Biol 158:235-246; and Wilson et al. (2009) Nature Immunol 10:348-355).

Cell Cycle Deregulation:

The loss of p16$^{INK4A}$ and decreased abundance of p53 targets, such as p21 and GADD45, relieve repression of the cell cycle components, CCND3 (cyclin D3), CDK2 and CDK1, respectively (FIG. 4; Shapiro, G. I. (2006) J Clin Oncol 24:1770-1783). In addition, CDK2, CCND3 and the cyclin D-associated CDKs, CDK4 and CDK6 are increased by copy gain (FIG. 4). Together, the identified CNAs increase the cyclin/CDK-dependent phosphorylation of RB and liberation of E2Fs (FIG. 4). In addition, RB1 and the related RB locus, RBL2 (p130), are targeted by copy loss in a subset of DLBCLs (FIG. 4). RB1 is also a recognized target of the MDM2 E3 ligase (Polager et al. (2009) Nature Rev Cancer 9:738-748).

Example 10: Signature of E2F Activation

An unbiased approach was sought to assess the relationship between CNA-dependent changes and the abundance of E2F target genes. Because transcription factors (TF) such as E2F will target genes outside the identified CNAs, the "trans-acting signature" of each CNA (those genes outside the CNA with the most significant association between transcript abundance and the CAN; FIG. 3A) were first defined. The union of the cis- and trans-acting signatures, termed the "global cis/trans-acting transcriptional signature," was then tested for enrichment of genes with common TF binding sites (FIG. 3A). The "global cis/trans-acting transcriptional signature" was significantly enriched for genes containing E2F binding sites. Specifically, 7/7 of top-ranked binding sites were either E2F, E2F/DP1 or E2F/DP2 (FIG. 3C; see Table 8 for the full list). These data indicate that DLBCL CNAs are tightly associated with cell cycle deregulation and increased abundance of E2F target genes.

Example 11: Patterns of CNAs of Pathway Components

The analysis of CNAs that perturb p53 signaling, apoptosis and cell cycle regulation also illustrates four important principles. First, a single CNA may alter several genes which synergistically modulate the same pathway, as in 17p13.1 copy loss decreasing expression of p53 itself and the p53 modifiers, RPL26 and KDM6B (JMJD3) (FIG. 4).

Second, several CNAs may modify the same pathway. For example, 1q23.3 copy gain (MDM4 and RFWD2), 9p21.3 copy loss (CDKN2A), 12q15 copy gain (MDM2), 17p13.1 copy loss (TP53, RPL26 and KDM6B) and 19q13.42 copy gain (BCL2L12) all function to decrease p53 activity (FIG. 4). Third, certain single CNAs may alter complementary pathways, such as 12q15 amplification (CDK2, CDK4 and MDM2) enhancing cell cycle progression and reducing p53 activity (FIG. 4). Fourth, multiple CNAs may modify complementary pathways such as p53 signaling, apoptosis and cell cycle regulation (FIG. 4).

Example 12: CNAs of p53 Pathway and Cell Cycle Components in Individual Primary DLBCLs After comprehensively defining CNAs that perturb p53 signaling and cell cycle pathways in DLBCLs, the patterns and combinations of alterations that occur in individual tumors was assessed. When the 180 primary DLBCLs were clustered in the space of the CNAs that alter p53 pathway and cell cycle components, 66% (118/180) of tumors had multiple alterations (termed "complex"), whereas the remaining 34% of tumors lacked these lesions (designated "clean", FIG. 5A). Primary DLBCLs with single copy loss of 17p13.1 (TP53/RPL26/KDM6B) often had CNAs perturbing an additional p53 modifier—9p21.3 (CDKN2A/ARF), 19q13.42 (BCL2L12), 12q15 (MDM2) or 1q23.3 (MDM4/RFWD2) (FIG. 5A). Of interest, CNAs of the respective p53 modifiers, CDKN2A (ARF, 9p21.3), MDM2 (12q15) and MDM4/RFWD2 (1q23.3) occurred in largely separate groups of tumors (FIG. 5A). DLBCLs with CNAs of p53 pathway members frequently exhibited concurrent alterations of additional cell cycle components, such as CCND3 (6p21.32), CDK6 (7q22.1), CDK2/CDK4 (12q15) and/or RB1 (13q14.2) or RBL2 (16q12.2) (FIG. 5A). Tumors with "complex" patterns of p53 pathway and cell cycle components also had more total CNAs than DLBCLs with "clean" p53/cell cycle signatures (FIG. 5A, bottom panel, Call CNAs, "complex" vs. "clean" p<0.0001, Mann-Whitney U test and FIG. 6) and more frequent TP53 mutations (FIG. 5A, top panel, "complex" 22% vs. "clean" 7%, p<0.005, FIG. 6, and Table 6). The patterns of "complex" vs. "clean" CNAs of p53 pathway and cell cycle components and the association between "complex" signature and total CNAs were confirmed in an independent series of 79 primary DLBCLs (FIG. 6B).

To further characterize "complex" vs. "clean" tumors, gene set enrichment analysis (GSEA) was performed with publicly available series of p53 target genes and a RB-deficiency, which included multiple E2F targets (Knudsen et al. (2008) Nat Rev Cancer 8:714-724). The GSEA computational method identifies statistically significant, concordant differences in the transcript abundance of a previously defined set of genes (such as p53 targets) in two biological states (i.e., "clean" versus "complex" primary DLBCLs) (Subramanian et al. (2005) PNAS 102:15545-15550). The p53 target transcripts were significantly less abundant in "complex" DLBCLs, directly linking their genetic signature of p53 deficiency with decreased p53 activity (FIG. 5B and FIG. 6C). Furthermore, the RB-deficiency gene set was significantly enriched in "complex" DLBCLs suggesting that these tumors had increased E2F-mediated cell cycle progression (FIG. 5C). Consistent with these observations, DLBCLs with "complex" CNA patterns also had significantly higher proliferation indices, as determined by Ki67 immunostaining (FIG. 5D, left and right panels).

Example 13: Structural Complexity as a Significant Predictor of Outcome

The prognostic significance of the "complex" CNA pattern in the subset of patients who were treated with R-CHOP (Rituxan® (rituximab), cyclophosphamide, Adriamycin® (doxorubicin), Oncovin® (vincristine), prednisone) therapy and had long-term followup was assessed (Table 9). R-CHOP treated patients with "complex" CNA patterns had a 5-year overall survival of only 62% whereas 100% of patients with "clean" CNA signatures were cured (FIG. 6A, p=0.001).

Figure 7:
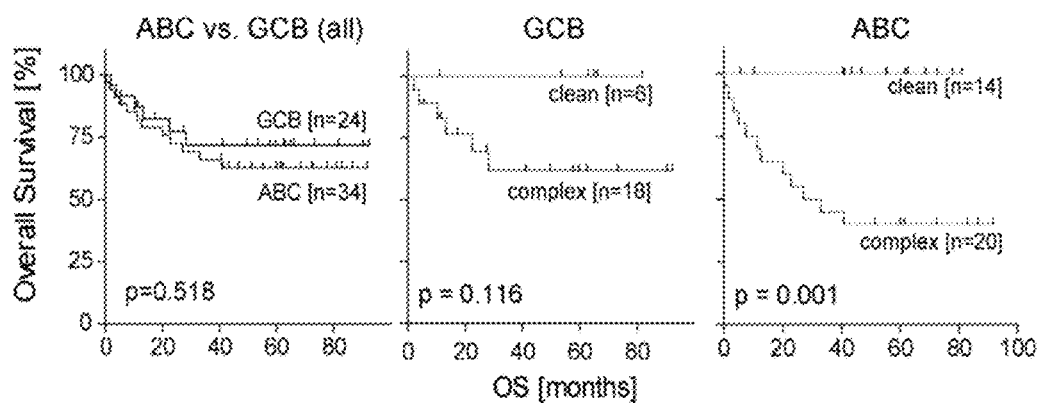
FIG. 7 shows the overall survival of R-CHOP treated DLBCL patients according to COO designation (ABC vs. GC only, left panel) and GC or ABC and "complex" vs. "clean" CAN pattern (middle and right panel) using a logrank test. P values are also shown.

The association between CN complexity and outcome was independent of transcriptional COO categories (FIG. 7).

The relationship of CN complexity and the clinical IPI risk model was next assessed. Although the IPI was highly predictive of outcome (Low/Low-Intermediate vs. High-Intermediate/High, FIG. 5F, left panel), the CNA pattern significantly increased prognostic accuracy (FIG. 5F, middle and right panel). In both the Low/Low-Intermediate and High-Intermediate/High-risk groups, patients whose tumors had "complex" CNAs had significantly shorter overall survivals, whereas all patients with "clean" CNA patterns were cured (FIG. 5F, middle and right panel). The contribution of the CNA pattern to IPI outcome stratification by IPI was also confirmed by a Cox-proportional hazard model (p<0.001). Taken together, these data provide a structural basis for deregulated cell cycle, increased cellular proliferation and unfavorable outcome in DLBCL.

Example 14: Targeting Deregulated Cell Cycle with Broad-Acting CDK Inhibitors

Figure 8:
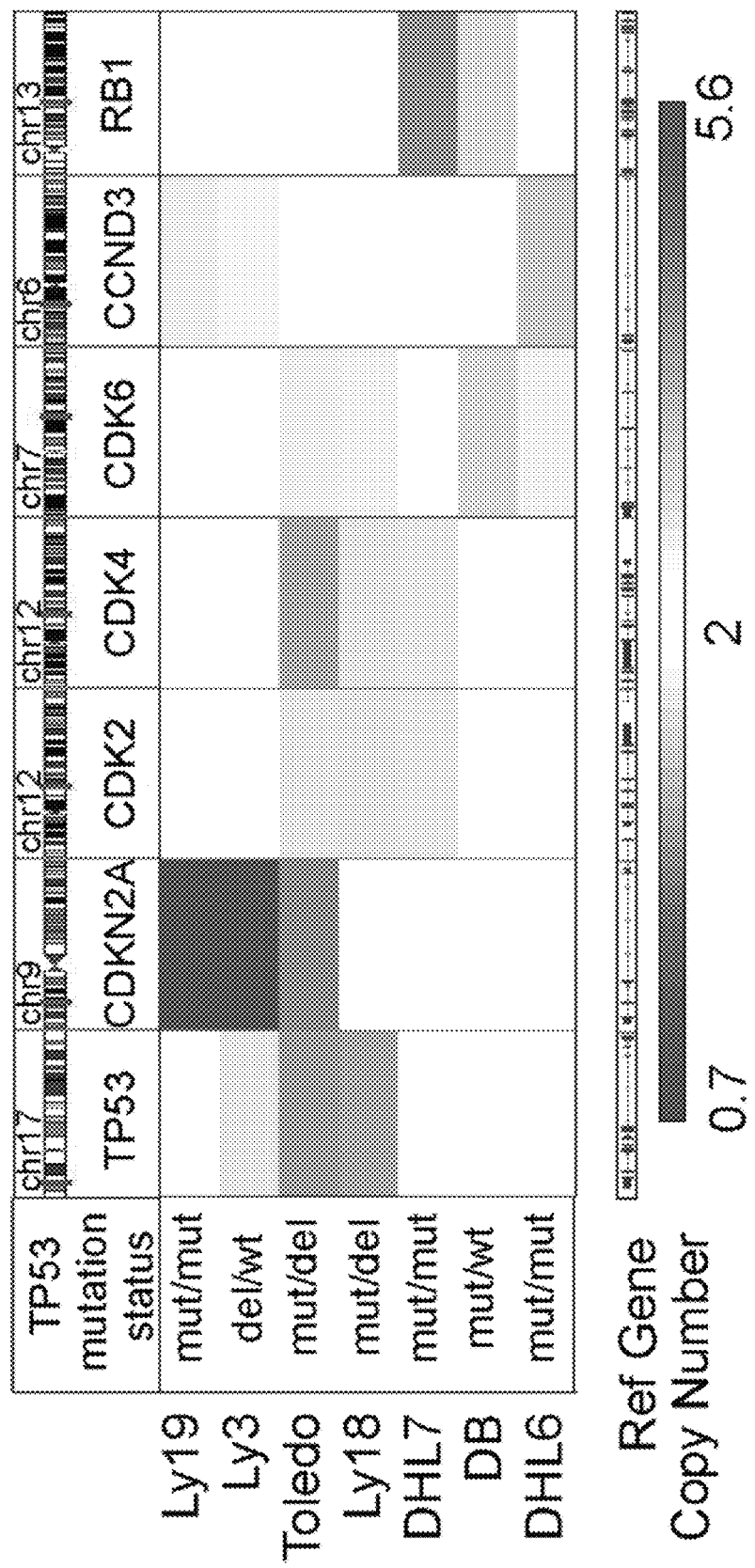
FIGS. 8A-8B show CNAs of cell cycle components and p53 in DLBCL cell lines. TP53 mutation status (left) and CNAs of TP53, CDKN2A, CDK2, CDK4, CDK6, CCND3, RFWD2, MDM2, MDM4, and RB1 are shown. CN gains are shown in light shading and CN losses are shown in dark shading. The color intensity corresponds to the magnitude of the CNA. Note that DHL7 has only one copy of RB1.
Figure 8:
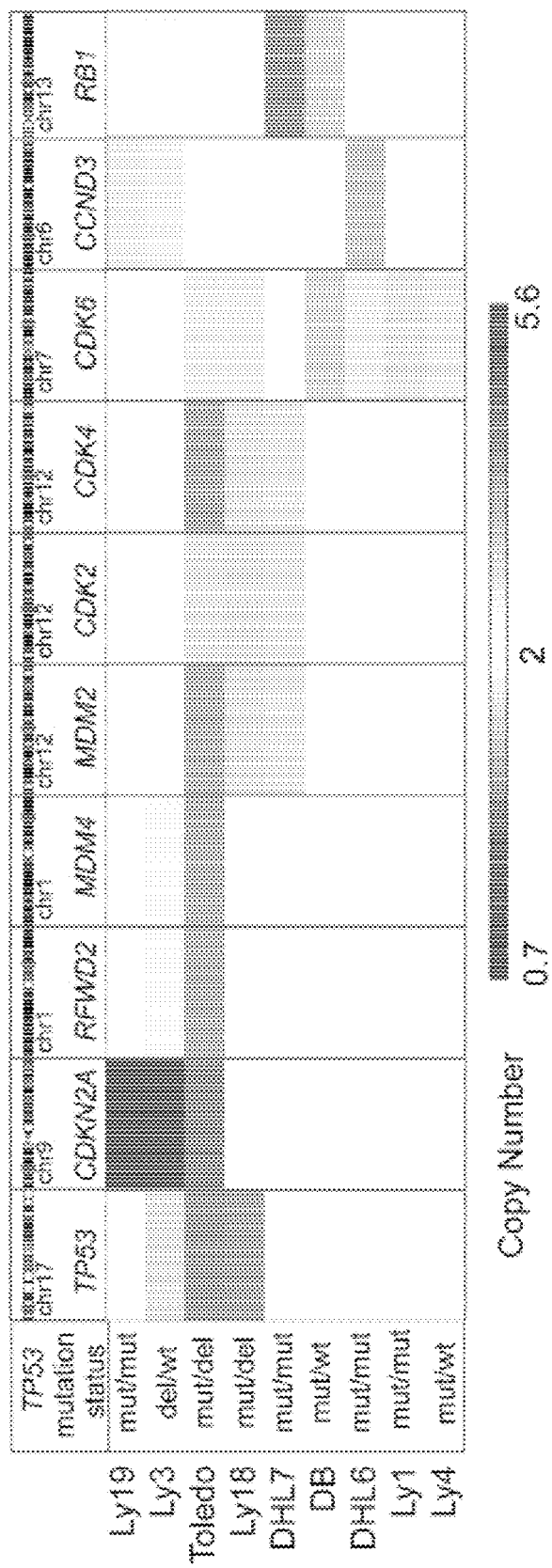
Figure 9:
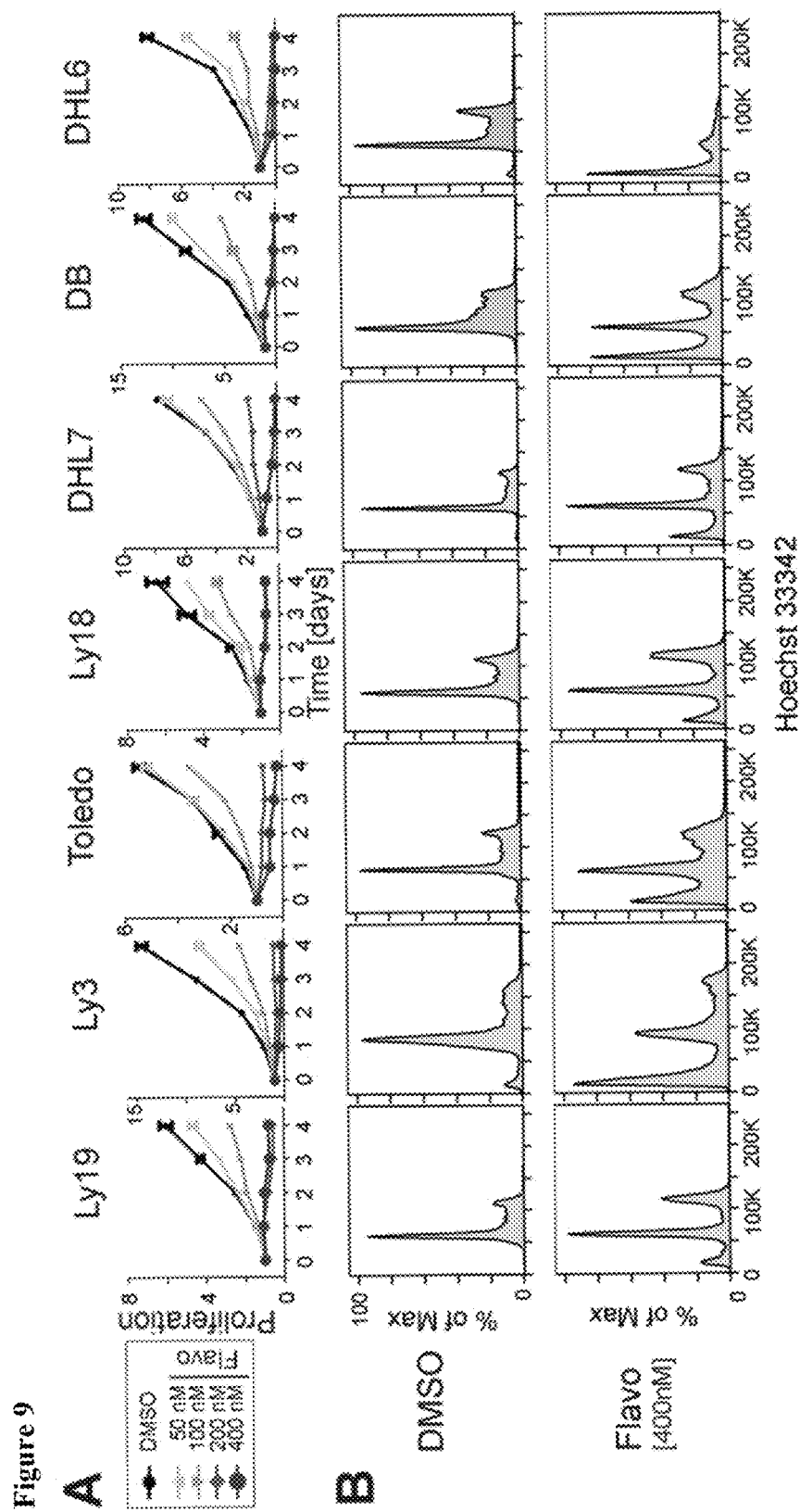
FIGS. 9A-9H show the results of treating DLBCL cell lines with a pan-CDK inhibitor. DLBCL cell lines with decreased or absent p53 activity and CNAs of CDKN2A, CCND3, CDK4, CDK6, CDK2 and/or copy loss of RB1 were treated with a pan-CDK inhibitor, flavopiridol, which blocks CDKs 4/6, 2 and 1 (and CDK9).
Figure 9:
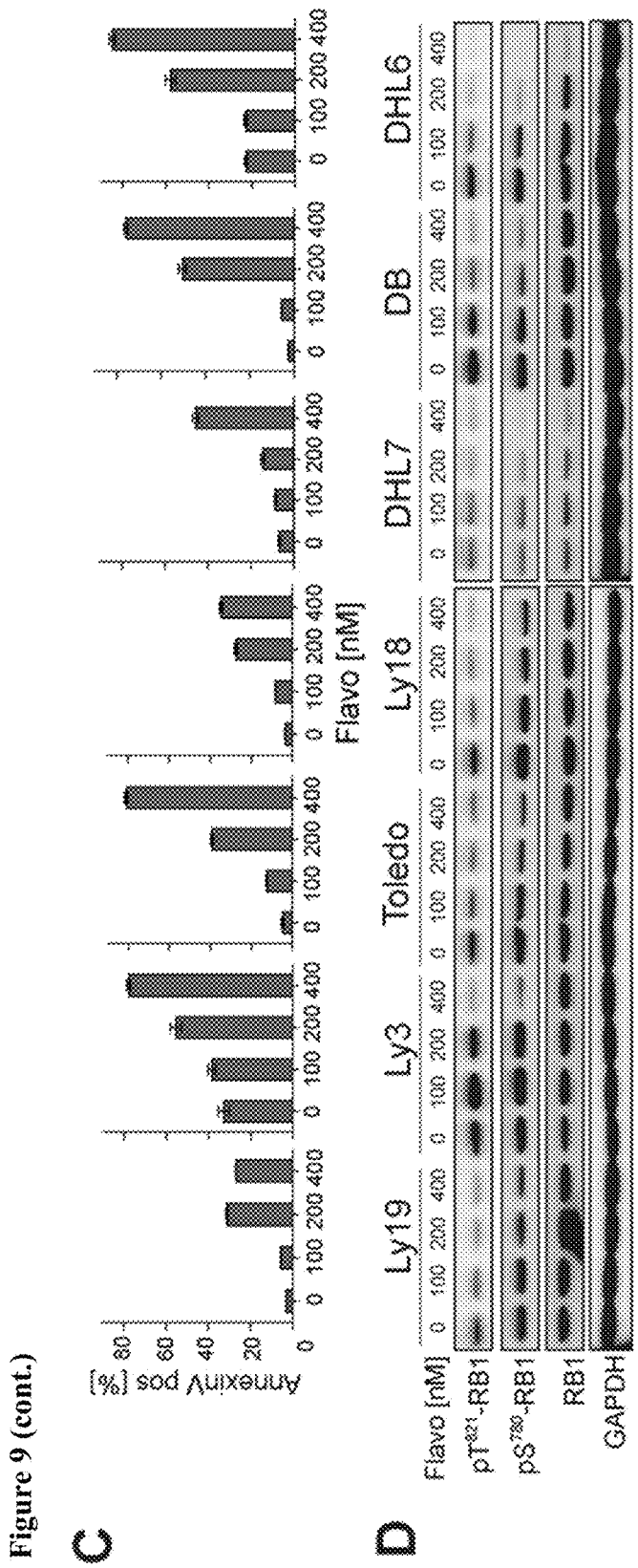
Figure 9:
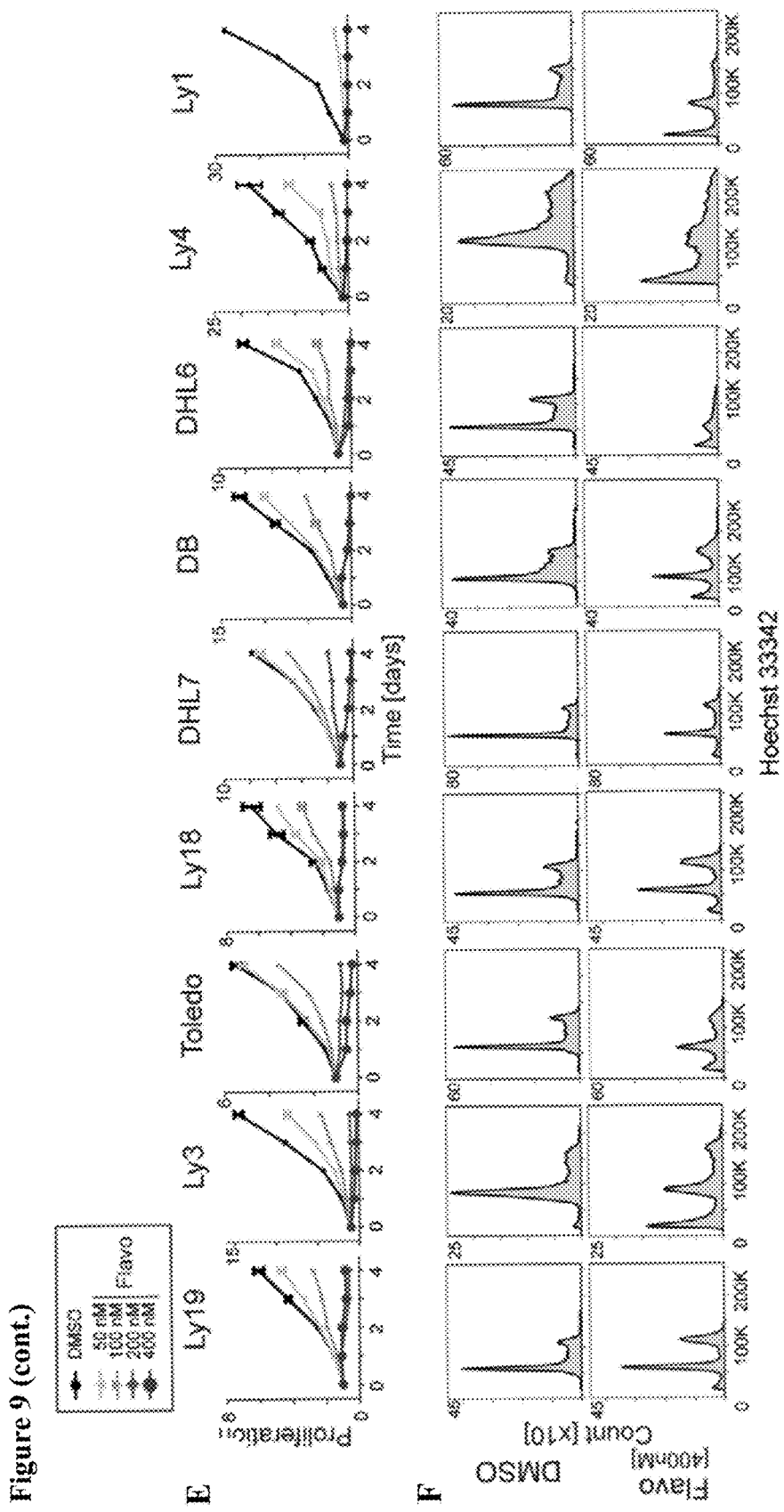
Figure 9:
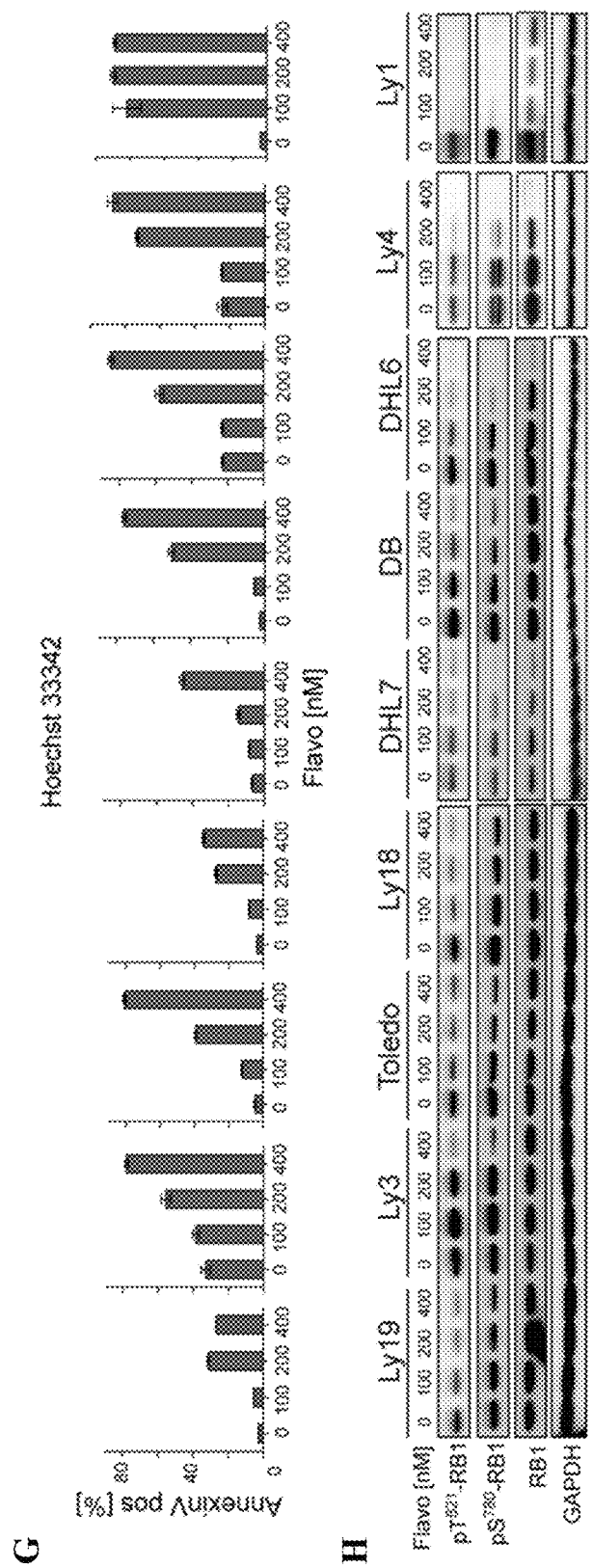
Figure 10:
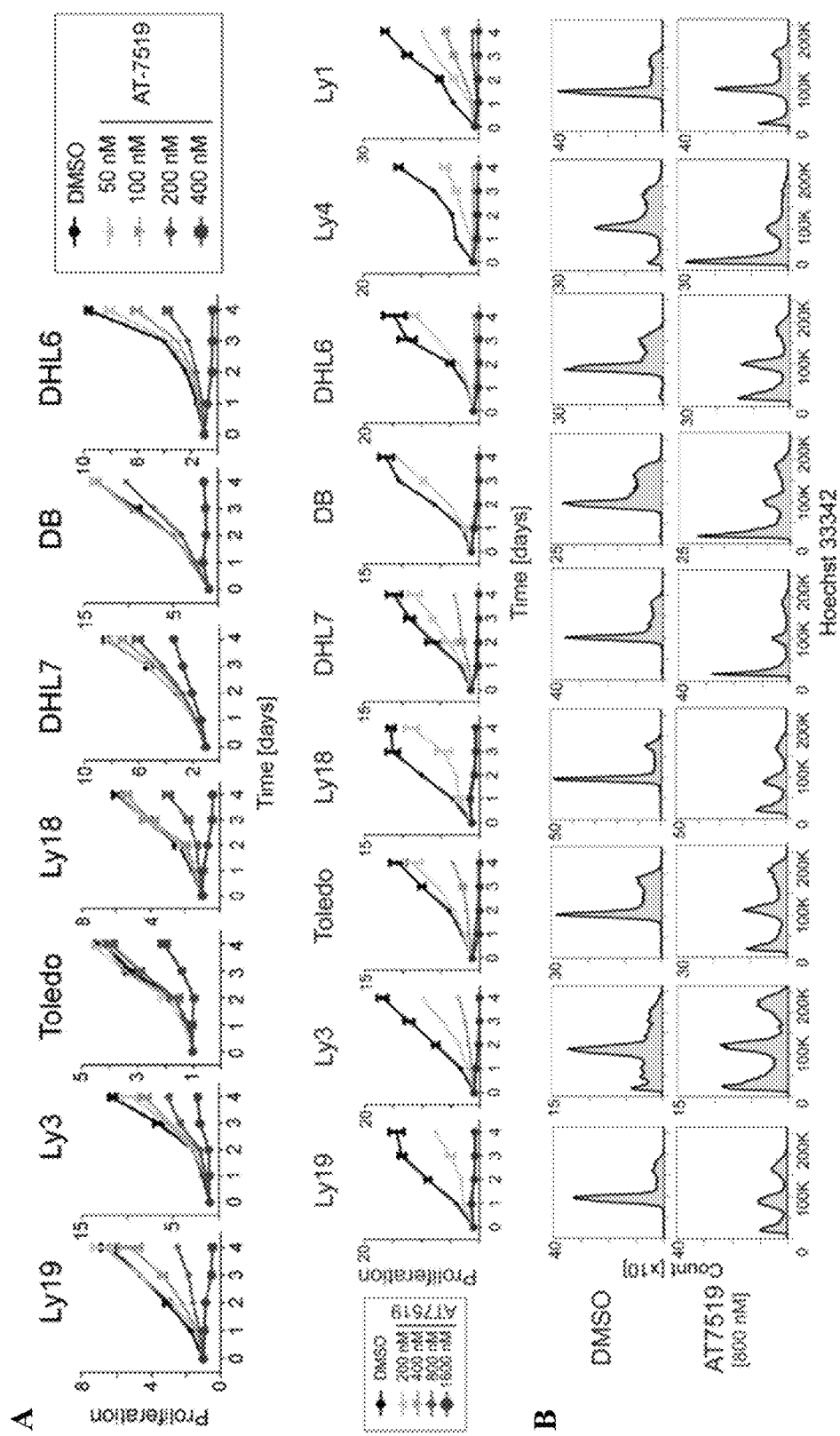
Figure 10:
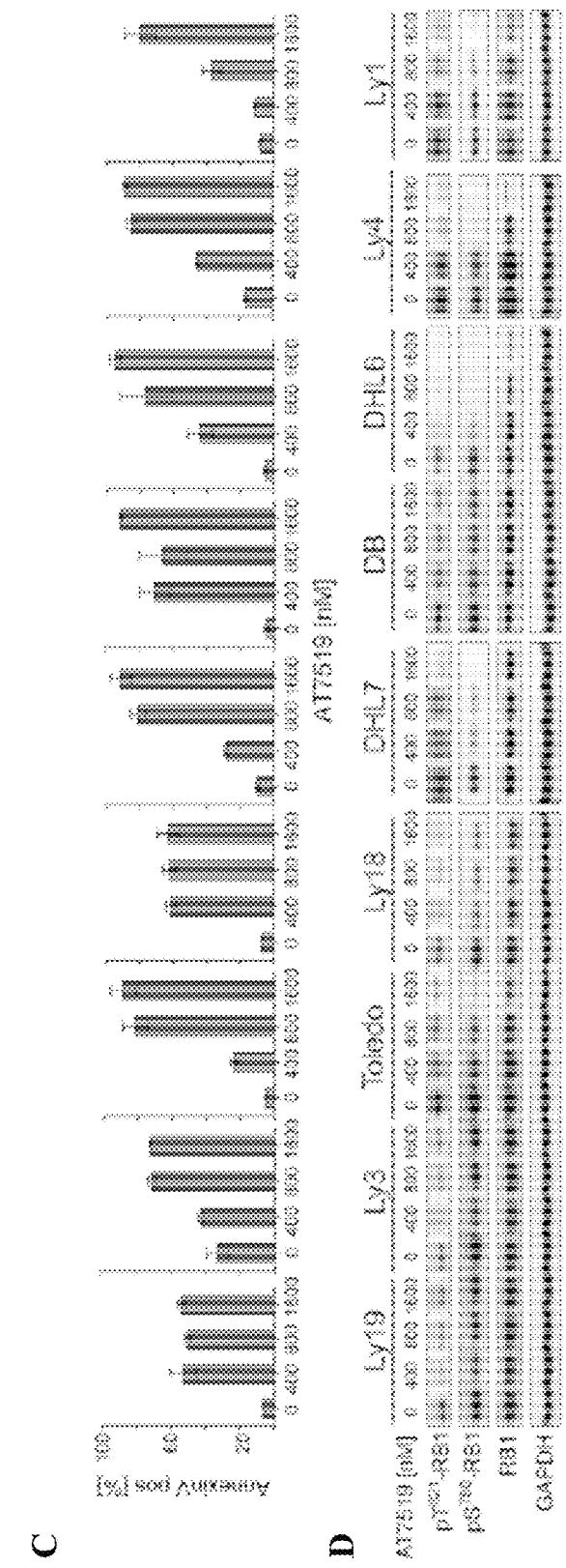

The predictive value of the "complex" CNA pattern and its association with deregulated cell cycle and increased activation of CDK4/6, CDK2 and, likely CDK1 (FIG. 4) prompted an analysis of the activity of a broad-acting CDK inhibitor, such as flavopiridol (Lapenna et al. (2009) Nat Rev Drug Discov 8:547-566 and Shapiro, G. I. (2006) J Clin Oncol 24:1770-1783) in DLBCL. A panel of DLBCL cell lines derived from patients with relapsed/refractory disease was used. All cell lines have decreased or absent p53 activity and CNAs of cell cycle components including CDKN2A, CCND3, CDK4, CDK6, CDK2 and/or copy loss of RB1 (FIG. 8A-8B). Flavopiridol, which inhibits CDKs 4/6, 2 and 1 (and CDK9), decreased the cellular proliferation of the DLBCL cell lines at nanomolar doses (FIG. 9). Similar results were obtained with a second pan-CDK inhibitor, AT-7519 (FIG. 10). Of interest, a DLBCL cell line with single copy RB1 loss (DHL7), was less sensitive to lower doses of flavopiridol (FIG. 9A), which is consistent with RB1 being downstream of the targeted CDKs. In these DLBCL cell lines, treatment with the pan-CDK inhibitor decreased S phase and induced cell cycle arrest (FIG. 9B). In addition, the broad-acting CDK inhibitor also increased apoptosis, as assessed by subG1 peaks and Annexin V/7-AAD staining (FIG. 8B-8C), and decreased the phosphorylation of RB1 at CDK4/6 and CDK2-specific sites (pS780 and pT821, respectively) (FIGS. 9D and 10). In multiple DLBCL xenograft models, flavopiridol treatment significantly reduced tumor growth and lymphoma infiltration of bone marrow and spleen (FIGS. 11A-11C). These data indicate that genetically driven cell cycle deregulation in DLBCL is amenable to targeted therapy.

Taken together, the combination of HD-SNP arrays, gene expression profiling and pathway analyses described herein has allowed for comprehensive definition of CNAs, associated candidate driver genes, and perturbed signaling pathways in a large series of newly diagnosed DLBCLs. The precision of the HD-SNP platform allowed for precise determination of the boundaries of recurrent CNAs and distinguish alterations that were unique to DLBCL from ones that were shared with multiple non-hematologic malignancies. By integrating data on CNAs with transcriptional profiles, driver genes with known functions in lymphomagenesis and identified additional candidates with previously unappreciated roles in DLBCL were identified and characterized. The multiple low-frequency (4% to 27%) CNAs prompted systematic evaluation of the alterations and associated genes with pathway analyses. The approach revealed a large complementary set of CNAs that decreased p53 activity and perturbed cell cycle regulation. The CNA-associated signature of p53 deficiency and cell cycle deregulation was highly predictive for outcome and potentially amenable to targeted therapy.

The CNA-associated pattern of deregulated p53 signaling was detected in 66% of newly diagnosed DLBCLs. This finding is of particular interest because somatic inactivating mutations of p53 are much less common in DLBCLs than in multiple epithelial malignancies. For example, only 16% of tumors in the current series of primary DLBCLs exhibited hemizygous TP53 mutations and the majority of these were in "complex" tumors with additional CNAs of p53 pathway members. All of the alterations of p53 modulators and signaling pathway components had the same functional effect—decreased abundance of functional p53 and reduced levels of p53 targets. In addition to identifying previously described CNAs of p53 modifiers such as CDKN2A (ARF) and MDM2 and TP53 itself, we found CNAs of the p53 regulators, MDM4, RFWD2 and BCL2L12 in DLBCL. Furthermore, a "deletion block" on chromosome 17p13 was identified that includes two additional p53 modifiers, KDM6B and RPL26, as well as TP53. The concurrent loss of TP53, RPL26 and KDM6B perturbs p53 signaling to a greater degree than anticipated in tumors with hemizygous 17p13 deletions. The gain of both MDM4 and RFWD2 at 1q23.3 delineates an additional "amplicon block" that serves to decrease p53 activity. These insights regarding genetic mechanisms that reduce normal p53 activity in DLBCL will inform targeted treatment strategies. For example, two recently developed p53 inhibitors are predicated on disrupting the interaction between functional p53 and the p53 modifiers, MDM2 and MDM4 (Bernal et al. (2010) Cancer Cell 18:411-422 and Shangary et al. (2008) Clin Cancer Res 14:5318-5324).

Besides copy loss of the cyclin D-dependent kinase inhibitor, p16$^{INK4A}$, copy gain of CDK4, CDK6 and CCND3, the most abundant and essential D-type cyclin in germinal center B cells, was also identified (Cato et al. (2011) Mol Cell Biol 31:127-137 and Peled et al. (2010) Cell Res 20:631-646). In addition to the likely relief of p53/p21-dependent CDK2 inhibition, copy gain of CDK2 in association with CDK4 (and MDM2) in a chromosome 12q15 "amplicon block" and copy loss of both RB1 and RBL2 were also found. There was a highly significant CNA-associated signature of increased E2F transcriptional activity underscoring the functional consequences of the identified genetic alterations.

The p53 and cell cycle component CNAs occur together in a comprehensive "complex" pattern in 66% of the primary DLBCLs. The remaining tumors have only rare CNAs. GSEA revealed that DLBCLs with "complex" CNAs had significantly less abundant expression of p53 target genes, directly linking their genetic signature of p53 deficiency with decreased p53 activity. In addition, these "complex" tumors exhibited enrichment of E2F targets by GSEA and increased cellular proliferation, as reflected by Ki67 immunostaining. Most importantly, the "complex" CNA pattern is highly predictive for outcome in DLBCL patients treated with R-CHOP. These data provide a mechanistic basis for previous observations regarding the prognostic significance of cellular proliferation in DLBCL (Grogan et al. (1988) Blood 71:1157 and Salles et al. (2011) Blood 117:7070-7078). In addition, the results described herein highlight the value of a comprehensive approach to identify CNA-defined alterations of p53 and cell cycle regulatory pathways, some of which have been characterized on an individual or selective basis and associated with outcome in earlier studies (Faber et al. (2007) Cell Cycle 6:2982-2989; Jardin et al. (2010) Blood 116:1092-1104; Sanchez-Beato et al. (2003) Blood 101:1220-1235; Winter et al. (2010) Clin Cancer Res 16:2435-2442; and Young et al. (2008) Blood 112:3088-3098). It was found that a single CNA (17p13.1) targets several p53 modulators, multiple CNAs perturb p53 activity (1q23.3, 9p21.3, 12q15, 17p13.1 and 19q13.42), and a single CNA (12q15/MDM2, CDK2 and CDK4) modulates both p53 signaling and cell cycle progression. Because the majority of these CNAs are shared with additional non-hematologic malignancies (FIG. 2), these findings are likely applicable to other tumor types. In addition, the "complex" pattern of CNAs represents an alternative mechanism for perturbing TP53 and deregulating cell cycle. In fact, an array CGH-defined "complex" pattern of copy gains and losses was recently associated with high mitotic counts and TP53 alterations in breast cancer (Kwei et al. (2010) Mol. Oncol. 4:255-266).

In the DLBCL series, tumors with "complex" CNAs of p53 and cell cycle components also had significantly more of the additional recurrent CNAs including focal and regional alterations and gains or losses of half or whole chromosomes (FIG. 6). The basis for the increased genomic instability is likely linked to the deficiencies in p53 signaling and perturbed cell cycle regulation. Numerical and structural chromosome instability (CIN) is better tolerated in a p53-deficient background and alterations of TP53, MDM2, MDM4 (MDMX), the CDK2 partner, CCNE1 (cyclin E1), and RB1 all foster CIN (Hernando et al. (2004) Nature 430:797-802; Matijasevic et al. (2008) Cell Cycle 7:2967-2973; Shlien et al. (2008) PNAS 105:11264-11269; Thompson et al. (2010) Current Biol 20:R285-R295; and Wang et al. (2008) Oncogene 27:1590-1598). In the setting of hyperactive CDKs and DNA damage, cell cycle progression further increases genomic instability (Malumbres et al. (2009) Nature Rev Cancer 9:153-166).

In addition to CNAs of the p53 apoptotic pathway, DLBCLs with the "complex" pattern exhibit alterations of other apoptotic members, including BCL2/18q21.33, FAS 10q23.32 and TNFRF10B/8p21.3 (FIG. 6). CNAs of immune recognition molecules, including HLA-B, HLA-C, MICA and MICB (6q21.33), B2M (15q21.1), CD58/1p13.1 and TNFSF9 (19p13.3), also largely occur in DLBCLs with "complex" alteration patterns (FIG. 6). These data indicate that additional defects in apoptosis and immune recognition are found in tumors with p53 deficiency, cell cycle deregulation and more widespread genomic instability. These data emphasize the importance of evaluating specific genetic alterations in the context of a more comprehensive assessment of CNAs and associated genomic instability.

Given the prognostic significance of the perturbed p53 signaling/cell cycle deregulation signature, the alterations indicate approaches to rational targeted therapy. The perturbed regulation of CDK4/CDK6, CDK2 and CDK1 and copy gains of CDK4/CDK6 and CDK2 prompted an evaluation of the activity of candidate broad-based CDK inhibitors. DLBCL cell lines with CNAs of p53 signaling and cell cycle components (with or without additional p53 mutations) all exhibited significant decreases in cellular proliferation in association with cell-cycle arrest, decreased RB phosphorylation and increased apoptosis in vitro and significantly reduced tumor growth in vivo. Therefore, prognostically significant, genetically driven cell cycle deregulation in DLBCL are amenable to targeted treatment.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

TABLE 9

| Parameter | n (%) |
|---|---|
| Sex | |
| female | 29 (40) |
| male | 43 (60) |

TABLE 9-continued

| Parameter | n (%) |
|---|---|
| Age (n = 72) | |
| under 60 | 28 (39) |
| 60 or older | 44 (61) |
| IPI (n = 68) | |
| Low | 24 (35) |
| Low-Intermediate | 17 (25) |
| High-Intermediate | 15 (22) |
| High | 12 (18) |
| OS median [range] in months | 48 (0-92) |
| COO (n = 170) | |
| ABC | 34 (49) |
| GCB | 24 (34) |
| unclassified | 12 (17) |
| CCC (n = 70) | |
| BCR | 19 (27) |
| OxP | 25 (36) |
| HR | 17 (24) |
| unclassified | 9 (13) |

| | Clean BLBCL N = 24 (R-CHOP-like treated) | Complex DLBCL N = 40 (R-CHOP-like treated) | Kruskal Wallis test p |
|---|---|---|---|
| Age median [range] | 60 (27-83) | 68 (32-86) | |
| Sex Male/Female | 18 (75%)/ 6 (25%) | 25 (52%)/ 23 (48%) | |
| IPI (n = 68) | | | 0.003 |
| Low | 14 | 10 | |
| Low-Intermediate | 2 | 15 | |
| High-Intermediate | 3 | 12 | |
| High | 2 | 10 | |

TABLE 10

| | SNParray Before Filtering | SNParray After Filtering | Paired Expression |
|---|---|---|---|
| DLBCL | 199 | 180 | 169 |
| Normals | 41 | 41 | |
| Total | 240 | 224 | 169 |

What is claimed is:

1. A method of treating a human subject afflicted with diffuse large B-cell lymphoma (DLBCL), the method comprising:
   i) obtaining gene profiles of the human subject comprising an analysis of whether the human subject has an increased copy number of 1q23.3 and an increased level of expression of at least one of MDM4 and RFWD2, wherein the analysis is achieved by:
      a) determining the copy number of 1q23.3 and the level of expression of at least one of MDM4 and RFWD2 in a sample from the human subject, wherein the sample comprises DLBCL cells;
      b) determining the normal copy number of 1q23.3 and the level of expression of at least one of MDM4 and RFWD2 in a control sample; and
      c) comparing the copy number of 1q23.3 and the level of expression of at least one of MDM4 and RFWD2 detected in steps a) and b); and
   ii) administering a cyclin-dependent kinase (CDK) inhibitor to the human subject having increased copy number of 1q23.3 and increased level of expression of at least one of MDM4 and RFWD2 relative to the normal copy number and the level of expression in the control sample, wherein the CDK inhibitor is a small molecule that inhibits CDK1, CDK2, CDK4, CDK6, and CDK9.

2. The method of claim 1, wherein said human subject has at least twenty percent increase of the level of expression of at least one of MDM4 and RFWD2 relative to the normal level of expression in the control sample.

3. A method for treating diffuse large B-cell lymphoma (DLBCL) in a human subject, the method comprising:
   i) monitoring the progression of the DLBCL in the human subject, comprising:
      a) detecting in a sample from the human subject at a first point in time the copy number of 1q23.3 and the level of expression of at least one of MDM4 and RFWD2, wherein the sample comprises DLBCL cells;
      b) repeating step a) at a subsequent point in time; and
      c) comparing the copy number of 1q23.3 and the level of expression of at least one of MDM4 and RFWD2 detected in steps a) and b) to monitor the progression of the DLBCL; and
   ii) administering a cyclin-dependent kinase (CDK) inhibitor to the human subject having increased copy number of 1q23.3 and increased level of expression of at least one of MDM4 and RFWD2 relative to the first point in time at the subsequent point in time, wherein the CDK inhibitor is a small molecule that inhibits CDK1, CDK2, CDK4, CDK6, and CDK9.

4. The method of claim 3, wherein an at least twenty percent increase of the level of expression of at least one of MDM4 and RFWD2 in the sample at a subsequent point in time relative to in the sample at the first point in time indicates progression of the DLBCL.

5. The method of claim 3, wherein less than a twenty percent increase of the level of expression of at least one of MDM4 and RFWD2 in the sample at a subsequent point in time relative to in the sample at the first point in time indicates a lack of progression of the DLBCL.

6. The method of claim 3, wherein between the first point in time and the subsequent point in time, the subject has undergone treatment to ameliorate the DLBCL.

7. The method of claim 1, further comprising treating the human subject with one or more therapeutic agents selected from the group consisting of rituximab, cyclophosphamide, doxorubicin, vincristine, prednisone, and a chemotherapeutic.

8. The method of claim 1, wherein the human subject has a copy number aberration (CNA) pattern involving another biomarker selected from the group of biomarkers consisting of CDKN2A, CDK6, TP53, KDM6B, RPL26, RBL2, BCL2L12, RB1, CDK2, CDK4, MDM2 and CCND3.

9. The method of claim 1, wherein the sample comprises cells, tissue, blood, buccal scrape, saliva, cerebrospinal fluid, stool, mucus, or bone marrow, obtained from the human subject.

10. The method of claim 1, wherein the copy number is assessed by microarray, quantitative PCR (qPCR), high-throughput sequencing, comparative genomic hybridization (CGH), or fluorescent in situ hybridization (FISH).

11. The method of claim 1, wherein the expression level of the at least one of MDM4 and RFWD2 is assessed by detecting the presence in the samples of a polynucleotide molecule encoding MDM4 or RFWD2.

12. The method of claim 11, wherein the polynucleotide molecule is a mRNA or cDNA.

13. The method of claim 11, wherein the step of detecting further comprises amplifying the polynucleotide molecule.

14. The method of claim 1, wherein the expression level of the at least one of MDM4 and RFWD2 is assessed by annealing a nucleic acid probe with a polynucleotide encoding MDM4 or RFWD2 in the samples under stringent hybridization conditions.

15. The method of claim 1, wherein the expression level of the at least one of MDM4 and RFWD2 is assessed by detecting the presence in the samples of a protein of MDM4 or RFWD2.

16. The method of claim 15, wherein the presence of said protein is detected using an antibody or an antigen binding fragment thereof which specifically binds with said protein.

17. The method of claim 1, wherein the human subject further has a copy loss at 17p13.1.

18. The method of claim 1, wherein the human subject further has copy number aberration (CNA) of at least one of 9q21.3, 19q13.42, 12q15, 6p21.32, 7q22.1, 13q14.2, and 16q12.2.

19. The method of claim 8, wherein the human subject further has copy number gain of at least one of CDK6, BCL2L12, CDK2, CDK4, MDM2, and CCND3.

20. The method of claim 8, wherein the human subject further has copy number loss of at least one of CDKN2A, TP53, KDM6B, RPL26, RBL2, and RB1.

* * * * *

UNITED STATES PATENT AND TRADEMARK OFFICE
CERTIFICATE OF CORRECTION

PATENT NO. : 9,890,429 B2
APPLICATION NO. : 14/381004
DATED : February 13, 2018
INVENTOR(S) : Margaret A. Shipp et al.

Page 1 of 1

It is certified that error appears in the above-identified patent and that said Letters Patent is hereby corrected as shown below:

In the Specification

At Column 1, before Large Files please add:
--Government Support
This invention was made with government support under grant number CA092625 awarded by The National Institutes of Health. The government has certain rights in the invention.--.

Signed and Sealed this
Twenty-fourth Day of September, 2019

Andrei Iancu
*Director of the United States Patent and Trademark Office*

```
SEQUENCE LISTING

<160> NUMBER OF SEQ ID NOS: 33

<210> SEQ ID NO 1
<211> LENGTH: 5049
<212> TYPE: DNA
<213> ORGANISM: Homo sapiens

<400> SEQUENCE: 1
atgcatcggg cagtggaccc tccaggggcc cgcgctgcac gggaagcctt tgcccttggg      60
ggcctgagct gtgctggggc ctggagctcc tgcccgcctc atccccctcc tcgtagcgca     120
tggctgcctg gaggcagatg ctcagccagc attgggcagc ccccgcttcc tgctccccta     180 ccccccttcac atggcagtag ttctgggcac cccagcaaac catattatgc tccaggggcg     240
cccactccaa gaccccctcca tgggaagctg gaatccctgc atggctgtgt gcaggcattg    300
```

```
ctccgggagc cagcccagcc agggctttgg gaacagcttg ggcaactgta cgagtcagag    360
cacgatagtg aggaggccac acgctgctac cacagcgccc ttcgatacgg aggaagcttc    420
gctgagctgg ggccccgcat tggccgactg cagcaggccc agctctggaa ctttcatact    480
ggctcctgcc agcaccgagc caaggtcctg cccccactgg agcaagtgtg aacttgcta    540 caccttgagc acaaacggaa ctatggagcc aagcggggag gtcccccggt gaagcgagct    600
gctgaacccc cagtggtgca gcctgtgcct cctgcagcac tctcaggccc tcaggggag    660 gagggcctca gcctggagg caagcgaagg agaggctgca actctgaaca gactggcctt    720
cccccagggc tgccactgcc tccaccacca ttaccaccac caccaccacc accaccaca    780 ccaccaccac ccctgcctgg cctggctacc agccccccat ttcagctaac caagccaggg    840
ctgtggagta ccctgcatgg agatgcctgg ggcccagagc gcaagggttc agcaccccca    900
gagcgccagg agcagcggca ctcgctgcct cacccatatc catacccagc tccagcgtac    960
accgcgcacc cccctggcca ccggctggtc ccggctgctc cccaggccc aggccccgc    1020 cccccaggag cagagagcca tggctgcctg cctgccaccc gtcccccgg aagtgacctt    1080 agagagagca gagttcagag gtcgcggatg gactccagcg tttcaccagc agcaaccacc    1140
gcctgcgtgc cttacgcccc ttcccggccc cctggcctcc ccggcaccac caccagcagc    1200
agcagtagca gcagcagcaa cactggtctc cggggcgtgg agccgaaccc aggcattccc    1260
ggcgctgacc attaccaaac tcccgcgctg gaggtctctc accatggccg cctggggccc    1320
tcggcacaca gcagtcggaa accgttcttg ggggctcccg ctgccactcc ccacctatcc    1380
ctgccacctg gaccttcctc accccctcca ccccctgtc cccgcctctt acgccccca    1440 ccacccctg cctggttgaa gggtccggcc tgccgggcag cccgagagga tggagagatc    1500
ttagaagagc tcttctttgg gactgaggga ccccccgcc ctgccccacc acccctcccc    1560
catcgcgagg gcttcttggg gcctccggcc tcccgcttt ctgtgggcac tcaggattct    1620
cacacccctc ccactccccc aaccccaacc accagcagta gcaacagcaa cagtggcagc    1680
cacagcagca gccctgctgg gcctgtgtcc tttcccccac caccctatct ggccagaagt    1740
atagaccccc ttccccggcc tcccagccca gcacagaacc cccaggaccc acctcttgta    1800
cccctgactc ttgccctgcc tccagcccct ccttcctcct gccaccaaaa tacctcagga    1860
agcttcaggc gccggagag cccccggccc agggtctcct tcccaaagac ccccgaggtg    1920
gggccggggc cacccccagg cccctgagt aaagccccc agcctgtgcc gcccggggtt    1980
ggggagctgc ctgcccgagg ccctcgactc tttgattttc cccccactcc gctgaggac    2040 cagtttgagg agccagccga attcaagatc ctacctgatg ggctggccaa catcatgaag    2100
atgctggacg aatccattcg caaggaagag gaacagcaac aacacgaagc aggcgtggcc    2160
ccccaacccc cgctgaagga gccctttgca tctctgcagt ctccttcccc caccgacaca    2220
gcccccacca ctactgctcc tgctgtcgcc gtcaccacca ccaccaccac caccaccacc    2280
accacggcca cccaggaaga ggagaagaag ccaccaccag cctaccacc accacggcct    2340 ctagccaagt ccctccacc ctctcagcca cagccaccac caccccccacc cccagcccg    2400 gccagcctgc tcaaatcctt ggcctccgtg ctggaggac aaaagtactg ttatcggggg    2460
actggagcag ctgttccac ccggcctggg cccttgccca ccactcagta ttcccctgc    2520 ccccatcag gtgctaccgc cctgccgccc acctcagcgg ccctagcgc caggctcc    2580 ccacagccct ctgcttcctc gtcatctcag ttctctacct caggcgggcc ctgggcgg    2640
```

```
gagcgcaggg cgggcgaaga gccagtcccg ggccccatga ccccacccca accgccccca    2700
cccctatctc tgcccctgc tcgctctgag tctgaggtgc tagaagagat cagccgggct     2760
tgcgagaccc ttgtggagcg ggtgggccgg agtgccactg acccagccga cccagtggac    2820
acagcagagc cagcggacag tgggactgag cgactgctgc ccccgcaca ggccaaggag     2880 gaggctggcg gggtggcggc agtgtcaggc agctgtaagc ggcgacagaa ggagcatcag    2940
aaggagcatc ggcggcacag gcgggcctgt aaggacagtg tgggtcgtcg gccccgtgag    3000
ggcagggcaa aggccaaggc caaggtcccc aaagaaaaga gccgccgggt gctggggaac    3060
ctggacctgc agagcgagga gatccagggt cgtgagaagt cccggcccga tcttggcggg    3120
gcctccaagg ccaagccacc cacagctcca gcccctccat cagctcctgc accttctgcc    3180
cagcccacac ccccgtcagc ctctgtccct ggaaagaagg ctcggaggag agccccaggg    3240
ccaccgggtg tcagccgggc cgacatgctg aagctgcgct cacttagtga ggggccccc    3300 aaggagctga agatccggct catcaaggta gagagtggtg acaaggagac ctttatcgcc    3360
tctgaggtgg aagagcggcg gctgcgcatg gcagacctca ccatcagcca ctgtgctgct    3420
gacgtcgtgc gcgccagcag gaatgccaag gtgaaaggga gtttcgaga gtcctacctt      3480 tcccctgccc agtctgtgaa accgaagatc aacactgagg agaagctgcc ccgggaaaaa    3540
ctcaaccccc ctacacccag catctatctg gagagcaaac gggatgcctt ctcacctgtc    3600
ctgctgcagt tctgtacaga ccctcgaaat cccatcacag tgatccgggg cctggcgggc    3660
tccctgcggc tcaacttggg cctcttctcc accaagaccc tggtggaagc gagtggcgaa    3720
cacaccgtgg aagttcgcac ccaggtgcag cagcccctcag atgagaactg ggatctgaca    3780
ggcactcggc agatctggcc ttgtgagagc tcccgttccc acaccaccat tgccaagtac    3840
gcacagtacc aggcctcatc cttccaggag tctctgcagg aggagaagga gagtgaggat    3900
gaggagtcag aggagccaga cagcaccact ggaaccctc ctagcagcgc accagacccg    3960
aagaaccatc acatcatcaa gtttggcacc aacatcgact tgtctgatgc taagcggtgg    4020
aagccccagc tgcaggagct gctgaagctg cccgccttca tgcgggtaac atccacgggc    4080
aacatgctga ccacgtgggg ccacaccatc ctgggcatga acacggtgca gctgtacatg    4140
aaggtgcccg gcagccgaac gccaggccac caggagaata caacttctg ctccgtcaac     4200 atcaacattg gccaggcga ctgcgagtgg ttcgcggtgc acgagcacta ctgggagacc    4260
atcagcgctt tctgtgatcg gcacggcgtg gactacttga cgggttcctg gtggccaatc    4320
ctggatgatc tctatgcatc caatattcct gtgtaccgct tcgtgcagcg acccggagac    4380
ctcgtgtgga ttaatgcggg gactgtgcac tgggtgcagg ccaccggctg gtgcaacaac    4440
attgcctgga acgtggggcc cctcaccgcc tatcagtacc agctggccct ggaacgatac    4500
gagtggaatg aggtgaagaa cgtcaaatcc atcgtgccca tgattcacgt gtcatggaac    4560
gtggctcgca cggtcaaaat cagcgacccc gacttgttca agatgatcaa gttctgcctg    4620
ctgcagtcca tgaagcactg ccaggtgcaa cgcgagagcc tggtgcgggc agggaagaaa    4680
atcgcttacc agggccgtgt caaggacgag ccagcctact actgcaacga gtgcgatgtg    4740 gaggtgtttta acatcctgtt cgtgacaagt gagaatggca gccgcaacac gtacctggta    4800
cactgcgagg gctgtgcccg gcgccgcagc gcaggcctgc agggcgtggt ggtgctggag    4860
cagtaccgca ctgaggagct ggctcaggcc tacgacgcct tcacgctggt gagggccggg    4920
cgggcgcgcg gcagcggag gagggcactg gggcaggctg cagggacggg cttcgggagc    4980
ccggccgcgc cttttccctga gcccccgccg gctttctccc ccaggccccc agccagcacg    5040
```

```
tcgcgatga                                                        5049
```

<210> SEQ ID NO 2
<211> LENGTH: 1682
<212> TYPE: PRT
<213> ORGANISM: Homo sapiens

<400> SEQUENCE: 2

```
Met His Arg Ala Val Asp Pro Gly Ala Arg Ala Arg Glu Ala
1               5                   10                  15

Phe Ala Leu Gly Gly Leu Ser Cys Ala Gly Ala Trp Ser Ser Cys Pro
                20                  25                  30

Pro His Pro Pro Arg Ser Ala Trp Leu Pro Gly Gly Arg Cys Ser
            35                  40                  45

Ala Ser Ile Gly Gln Pro Pro Leu Pro Ala Pro Leu Pro Pro Ser His
    50                  55                  60

Gly Ser Ser Gly His Pro Ser Lys Pro Tyr Tyr Ala Pro Gly Ala
65                  70                  75                  80

Pro Thr Pro Arg Pro Leu His Gly Lys Leu Glu Ser Leu His Gly Cys
                85                  90                  95

Val Gln Ala Leu Leu Arg Glu Pro Ala Gln Pro Gly Leu Trp Glu Gln
                100                 105                 110

Leu Gly Gln Leu Tyr Glu Ser Glu His Asp Ser Glu Glu Ala Thr Arg
            115                 120                 125

Cys Tyr His Ser Ala Leu Arg Tyr Gly Gly Ser Phe Ala Glu Leu Gly
    130                 135                 140

Pro Arg Ile Gly Arg Leu Gln Gln Ala Gln Leu Trp Asn Phe His Thr
145                 150                 155                 160

Gly Ser Cys Gln His Arg Ala Lys Val Leu Pro Pro Leu Glu Gln Val
                165                 170                 175

Trp Asn Leu Leu His Leu Glu His Lys Arg Asn Tyr Gly Ala Lys Arg
            180                 185                 190

Gly Gly Pro Pro Val Lys Arg Ala Ala Glu Pro Pro Val Val Gln Pro
        195                 200                 205

Val Pro Pro Ala Ala Leu Ser Gly Pro Ser Gly Glu Glu Gly Leu Ser
    210                 215                 220

Pro Gly Gly Lys Arg Arg Arg Gly Cys Asn Ser Glu Gln Thr Gly Leu
225                 230                 235                 240

Pro Pro Gly Leu Pro Leu Pro Pro Pro Leu Pro Pro Pro Pro
                245                 250                 255

Pro Pro Pro Pro Pro Pro Pro Leu Pro Gly Leu Ala Thr Ser Pro
            260                 265                 270

Pro Phe Gln Leu Thr Lys Pro Gly Leu Trp Ser Thr Leu His Gly Asp
    275                 280                 285

Ala Trp Gly Pro Glu Arg Lys Gly Ser Ala Pro Pro Glu Arg Gln Glu
    290                 295                 300

Gln Arg His Ser Leu Pro His Pro Tyr Pro Tyr Pro Ala Pro Ala Tyr
305                 310                 315                 320

Thr Ala His Pro Pro Gly His Arg Leu Val Pro Ala Pro Pro Gly
                325                 330                 335

Pro Gly Pro Arg Pro Pro Gly Ala Glu Ser His Gly Cys Leu Pro Ala
            340                 345                 350

Thr Arg Pro Pro Gly Ser Asp Leu Arg Glu Ser Arg Val Gln Arg Ser
    355                 360                 365
```

```
Arg Met Asp Ser Ser Val Ser Pro Ala Ala Thr Thr Ala Cys Val Pro
        370             375             380
Tyr Ala Pro Ser Arg Pro Pro Gly Leu Pro Gly Thr Thr Thr Ser Ser
385             390             395             400
Ser Ser Ser Ser Ser Ser Asn Thr Gly Leu Arg Gly Val Glu Pro Asn
                405             410             415
Pro Gly Ile Pro Gly Ala Asp His Tyr Gln Thr Pro Ala Leu Glu Val
            420             425             430
Ser His His Gly Arg Leu Gly Pro Ser Ala His Ser Ser Arg Lys Pro
        435             440             445
Phe Leu Gly Ala Pro Ala Ala Thr Pro His Leu Ser Leu Pro Pro Gly
    450             455             460
Pro Ser Ser Pro Pro Pro Pro Cys Pro Arg Leu Leu Arg Pro Pro
465             470             475             480
Pro Pro Pro Ala Trp Leu Lys Gly Pro Ala Cys Arg Ala Ala Arg Glu
            485             490             495
Asp Gly Glu Ile Leu Glu Leu Phe Phe Gly Thr Glu Gly Pro Pro
            500             505             510
Arg Pro Ala Pro Pro Leu Pro His Arg Glu Gly Phe Leu Gly Pro
        515             520             525
Pro Ala Ser Arg Phe Ser Val Gly Thr Gln Asp Ser His Thr Pro Pro
    530             535             540
Thr Pro Pro Thr Pro Thr Thr Ser Ser Ser Asn Ser Asn Ser Gly Ser
545             550             555             560
His Ser Ser Ser Pro Ala Gly Pro Val Ser Phe Pro Pro Pro Tyr
                565             570             575
Leu Ala Arg Ser Ile Asp Pro Leu Pro Arg Pro Pro Ser Pro Ala Gln
            580             585             590
Asn Pro Gln Asp Pro Pro Leu Val Pro Leu Thr Leu Ala Leu Pro Pro
        595             600             605
Ala Pro Pro Ser Ser Cys His Gln Asn Thr Ser Gly Ser Phe Arg Arg
    610             615             620
Pro Glu Ser Pro Arg Pro Arg Val Ser Phe Pro Lys Thr Pro Glu Val
625             630             635             640
Gly Pro Gly Pro Pro Gly Pro Leu Ser Lys Ala Pro Gln Pro Val
                645             650             655
Pro Pro Gly Val Gly Glu Leu Pro Ala Arg Gly Pro Arg Leu Phe Asp
            660             665             670
Phe Pro Pro Thr Pro Leu Glu Asp Gln Phe Glu Glu Pro Ala Glu Phe
        675             680             685
Lys Ile Leu Pro Asp Gly Leu Ala Asn Ile Met Lys Met Leu Asp Glu
    690             695             700
Ser Ile Arg Lys Glu Glu Gln Gln His Glu Ala Gly Val Ala
705             710             715             720
Pro Gln Pro Pro Leu Lys Glu Pro Phe Ala Ser Leu Gln Ser Pro Phe
            725             730             735
Pro Thr Asp Thr Ala Pro Thr Thr Thr Ala Pro Ala Val Ala Val Thr
        740             745             750
Thr Thr Thr Thr Thr Thr Thr Thr Thr Ala Thr Gln Glu Glu Glu
        755             760             765
Lys Lys Pro Pro Pro Ala Leu Pro Pro Pro Pro Leu Ala Lys Phe
770             775             780
```

```
Pro Pro Pro Ser Gln Pro Gln Pro Pro Pro Pro Pro Ser Pro
785                 790                 795                 800

Ala Ser Leu Leu Lys Ser Leu Ala Ser Val Leu Glu Gly Gln Lys Tyr
            805                 810                 815

Cys Tyr Arg Gly Thr Gly Ala Ala Val Ser Thr Arg Pro Gly Pro Leu
            820                 825                 830

Pro Thr Thr Gln Tyr Ser Pro Gly Pro Pro Ser Gly Ala Thr Ala Leu
            835                 840                 845

Pro Pro Thr Ser Ala Ala Pro Ser Ala Gln Gly Ser Pro Gln Pro Ser
850                 855                 860

Ala Ser Ser Ser Gln Phe Ser Thr Ser Gly Gly Pro Trp Ala Arg
865                 870                 875                 880

Glu Arg Arg Ala Gly Glu Glu Pro Val Pro Gly Pro Met Thr Pro Thr
                885                 890                 895

Gln Pro Pro Pro Leu Ser Leu Pro Pro Ala Arg Ser Glu Ser Glu
                900                 905                 910

Val Leu Glu Glu Ile Ser Arg Ala Cys Glu Thr Leu Val Glu Arg Val
            915                 920                 925

Gly Arg Ser Ala Thr Asp Pro Ala Asp Pro Val Asp Thr Ala Glu Pro
930                 935                 940

Ala Asp Ser Gly Thr Glu Arg Leu Leu Pro Ala Gln Ala Lys Glu
945                 950                 955                 960

Glu Ala Gly Gly Val Ala Ala Val Ser Gly Ser Cys Lys Arg Arg Gln
                965                 970                 975

Lys Glu His Gln Lys Glu His Arg Arg His Arg Arg Ala Cys Lys Asp
                980                 985                 990

Ser Val Gly Arg Arg Pro Arg Glu  Gly Arg Ala Lys Ala  Lys Ala Lys
            995                 1000                1005

Val Pro  Lys Glu Lys Ser Arg  Arg Val Leu Gly Asn  Leu Asp Leu
    1010                1015                1020

Gln Ser  Glu Glu Ile Gln Gly  Arg Glu Lys Ser Arg  Pro Asp Leu
    1025                1030                1035

Gly Gly  Ala Ser Lys Ala Lys  Pro Pro Thr Ala Pro  Ala Pro Pro
    1040                1045                1050

Ser Ala  Pro Ala Pro Ser Ala  Gln Pro Thr Pro  Ser Ala Ser
    1055                1060                1065

Val Pro  Gly Lys Lys Ala Arg  Glu Glu Ala Pro  Gly Pro Pro Gly
    1070                1075                1080

Val Ser  Arg Ala Asp Met Leu  Lys Leu Arg Ser Leu  Ser Glu Gly
    1085                1090                1095

Pro Pro  Lys Glu Leu Lys Ile  Arg Leu Ile Lys Val  Glu Ser Gly
    1100                1105                1110

Asp Lys  Glu Thr Phe Ile Ala  Ser Glu Val Glu Glu  Arg Arg Leu
    1115                1120                1125

Arg Met  Ala Asp Leu Thr Ile  Ser His Cys Ala Ala  Asp Val Val
    1130                1135                1140

Arg Ala  Ser Arg Asn Ala Lys  Val Lys Gly Lys Phe  Arg Glu Ser
    1145                1150                1155

Tyr Leu  Ser Pro Ala Gln Ser  Val Lys Pro Lys Ile  Asn Thr Glu
    1160                1165                1170

Glu Lys  Leu Pro Arg Glu Lys  Leu Asn Pro Pro Thr  Pro Ser Ile
    1175                1180                1185

Tyr Leu  Glu Ser Lys Arg Asp  Ala Phe Ser Pro Val  Leu Leu Gln
```

-continued

```
            1190                1195                1200
Phe Cys Thr Asp Pro Arg Asn Pro Ile Thr Val Ile Arg Gly Leu
    1205                1210                1215

Ala Gly Ser Leu Arg Leu Asn Leu Gly Leu Phe Ser Thr Lys Thr
    1220                1225                1230

Leu Val Glu Ala Ser Gly Glu His Thr Val Glu Val Arg Thr Gln
    1235                1240                1245

Val Gln Gln Pro Ser Asp Glu Asn Trp Asp Leu Thr Gly Thr Arg
    1250                1255                1260

Gln Ile Trp Pro Cys Glu Ser Ser Arg Ser His Thr Thr Ile Ala
    1265                1270                1275

Lys Tyr Ala Gln Tyr Gln Ala Ser Ser Phe Gln Glu Ser Leu Gln
    1280                1285                1290

Glu Glu Lys Glu Ser Glu Asp Glu Glu Ser Glu Glu Pro Asp Ser
    1295                1300                1305

Thr Thr Gly Thr Pro Pro Ser Ser Ala Pro Asp Pro Lys Asn His
    1310                1315                1320

His Ile Ile Lys Phe Gly Thr Asn Ile Asp Leu Ser Asp Ala Lys
    1325                1330                1335

Arg Trp Lys Pro Gln Leu Gln Glu Leu Leu Lys Leu Pro Ala Phe
    1340                1345                1350

Met Arg Val Thr Ser Thr Gly Asn Met Leu Ser His Val Gly His
    1355                1360                1365

Thr Ile Leu Gly Met Asn Thr Val Gln Leu Tyr Met Lys Val Pro
    1370                1375                1380

Gly Ser Arg Thr Pro Gly His Gln Glu Asn Asn Asn Phe Cys Ser
    1385                1390                1395

Val Asn Ile Asn Ile Gly Pro Gly Asp Cys Glu Trp Phe Ala Val
    1400                1405                1410

His Glu His Tyr Trp Glu Thr Ile Ser Ala Phe Cys Asp Arg His
    1415                1420                1425

Gly Val Asp Tyr Leu Thr Gly Ser Trp Trp Pro Ile Leu Asp Asp
    1430                1435                1440

Leu Tyr Ala Ser Asn Ile Pro Val Tyr Arg Phe Val Gln Arg Pro
    1445                1450                1455

Gly Asp Leu Val Trp Ile Asn Ala Gly Thr Val His Trp Val Gln
    1460                1465                1470

Ala Thr Gly Trp Cys Asn Asn Ile Ala Trp Asn Val Gly Pro Leu
    1475                1480                1485

Thr Ala Tyr Gln Tyr Gln Leu Ala Leu Glu Arg Tyr Glu Trp Asn
    1490                1495                1500

Glu Val Lys Asn Val Lys Ser Ile Val Pro Met Ile His Val Ser
    1505                1510                1515

Trp Asn Val Ala Arg Thr Val Lys Ile Ser Asp Pro Asp Leu Phe
    1520                1525                1530

Lys Met Ile Lys Phe Cys Leu Leu Gln Ser Met Lys His Cys Gln
    1535                1540                1545

Val Gln Arg Glu Ser Leu Val Arg Ala Gly Lys Lys Ile Ala Tyr
    1550                1555                1560

Gln Gly Arg Val Lys Asp Glu Pro Ala Tyr Tyr Cys Asn Glu Cys
    1565                1570                1575

Asp Val Glu Val Phe Asn Ile Leu Phe Val Thr Ser Glu Asn Gly
    1580                1585                1590
```

```
Ser  Arg  Asn  Thr  Tyr  Leu  Val  His  Cys  Glu  Gly  Cys  Ala  Arg  Arg
     1595                1600                1605

Arg  Ser  Ala  Gly  Leu  Gln  Gly  Val  Val  Val  Leu  Glu  Gln  Tyr  Arg
     1610                1615                1620

Thr  Glu  Glu  Leu  Ala  Gln  Ala  Tyr  Asp  Ala  Phe  Thr  Leu  Val  Arg
     1625                1630                1635

Ala  Arg  Arg  Ala  Arg  Gly  Gln  Arg  Arg  Ala  Leu  Gly  Gln  Ala
     1640                1645                1650

Ala  Gly  Thr  Gly  Phe  Gly  Ser  Pro  Ala  Ala  Pro  Phe  Pro  Glu  Pro
     1655                1660                1665

Pro  Pro  Ala  Phe  Ser  Pro  Gln  Ala  Pro  Ala  Ser  Thr  Ser  Arg
     1670                1675                1680

<210> SEQ ID NO 3
<211> LENGTH: 438
<212> TYPE: DNA
<213> ORGANISM: Homo sapiens

<400> SEQUENCE: 3
atgaagttta atccctttgt gacttccgac cgaagcaaga atcgcaaaag gcatttcaat      60
gcaccttccc acattcgaag gaagattatg tcttcccctc tttccaaaga gctgagacag     120
aagtacaacg tgcgatccat gcccatccga aaggatgatg aagttcaggt tgtacgtgga     180
cactataaag gtcagcaaat tggcaaagta gtccaggttt acaggaagaa atatgttatc     240
tacattgaac gggtgcagcg ggaaaaggct aatggcacaa ctgtccacgt aggcattcac     300
cccagcaagg tggttatcac taggctaaaa ctggacaaag accgcaaaaa gatcctcgaa     360
cggaaagcca aatctcgcca agtaggaaag gaaaagggca aatacaagga agaaaccatt     420
gagaagatgc aggaataa                                                   438

<210> SEQ ID NO 4
<211> LENGTH: 145
<212> TYPE: PRT
<213> ORGANISM: Homo sapiens

<400> SEQUENCE: 4

Met  Lys  Phe  Asn  Pro  Phe  Val  Thr  Ser  Asp  Arg  Ser  Lys  Asn  Arg  Lys
1                   5                   10                  15

Arg  His  Phe  Asn  Ala  Pro  Ser  His  Ile  Arg  Arg  Lys  Ile  Met  Ser  Ser
                    20                  25                  30

Pro  Leu  Ser  Lys  Glu  Leu  Arg  Gln  Lys  Tyr  Asn  Val  Arg  Ser  Met  Pro
         35                  40                  45

Ile  Arg  Lys  Asp  Asp  Glu  Val  Gln  Val  Val  Arg  Gly  His  Tyr  Lys  Gly
     50                  55                  60

Gln  Gln  Ile  Gly  Lys  Val  Val  Gln  Val  Tyr  Arg  Lys  Lys  Tyr  Val  Ile
65                  70                  75                  80

Tyr  Ile  Glu  Arg  Val  Gln  Arg  Glu  Lys  Ala  Asn  Gly  Thr  Thr  Val  His
                    85                  90                  95

Val  Gly  Ile  His  Pro  Ser  Lys  Val  Val  Ile  Thr  Arg  Leu  Lys  Leu  Asp
                100                 105                 110

Lys  Asp  Arg  Lys  Lys  Ile  Leu  Glu  Arg  Lys  Ala  Lys  Ser  Arg  Gln  Val
            115                 120                 125

Gly  Lys  Glu  Lys  Gly  Lys  Tyr  Lys  Glu  Glu  Thr  Ile  Glu  Lys  Met  Gln
        130                 135                 140

Glu
```

<210> SEQ ID NO 5
<211> LENGTH: 3420
<212> TYPE: DNA
<213> ORGANISM: Homo sapiens

<400> SEQUENCE: 5

| | | | | | | |
|---|---|---|---|---|---|---|
| atgccgtcgg | gaggtgacca | gtcgccaccg | cccccgcctc | ccctccggc | ggcggcagcc | 60 |
| tcggatgagg | aggaggagga | cgacggcgag | gcggaagacg | ccgcgccgcc | tgccgagtcg | 120 |
| cccaccctc | agatccagca | gcggttcgac | gagctgtgca | gccgcctcaa | catggacgag | 180 |
| gcggcgcggg | ccgaggcctg | ggacagctac | cgcagcatga | gcgaaagcta | cacgctggag | 240 |
| ggaaatgatc | ttcattggtt | agcatgtgcc | ttatatgtgg | cttgcagaaa | atctgttcca | 300 |
| actgtaagca | aagggacagt | ggaaggaaac | tatgtatctt | taactagaat | cctgaaatgt | 360 |
| tcagagcaga | gcttaatcga | atttttaat | aagatgaaga | agtgggaaga | catggcaaat | 420 |
| ctaccccac | atttcagaga | acgtactgag | agattagaaa | gaaacttcac | tgtttctgct | 480 |
| gtaatttta | agaaatatga | acccatttt | caggacatct | ttaaataccc | tcaagaggag | 540 |
| caacctcgtc | agcagcgagg | aaggaaacag | cggcgacagc | cctgtactgt | gtctgaaatt | 600 |
| ttccattttt | gttgggtgct | tttatatat | gcaaaaggta | atttcccat | gattagtgat | 660 |
| gatttggtca | attcttatca | cctgctgctg | tgtgctttgg | acttagttta | tggaaatgca | 720 |
| cttcagtgtt | ctaatcgtaa | agaacttgtg | aaccctaatt | ttaaaggctt | atctgaagat | 780 |
| tttcatgcta | aagattctaa | accttcctct | gaccccctt | gtatcattga | aaactgtgt | 840 |
| tccttacatg | atggcctagt | tttggaagca | aaggggataa | aggaacattt | ctggaaaccc | 900 |
| tatattagga | aactttatga | aaaaaagctc | cttaagggaa | aagaagaaaa | tctcactggg | 960 |
| tttctagaac | ctgggaactt | tggagagagt | tttaaagcca | tcaataaggc | ctatgaggag | 1020 |
| tatgttttat | ctgttgggaa | tttagatgag | cggatatttc | ttggagagga | tgctgaggag | 1080 |
| gaaattggga | ctctctcaag | gtgtctgaac | gctggttcag | gaacagagac | tgctgaaagg | 1140 |
| gtgcagatga | aaaacatctt | acagcagcat | tttgacaagt | ccaaagcact | tagaatctcc | 1200 |
| acaccactaa | ctggtgttag | gtacattaag | gagaatagcc | cttgtgtgac | tccagtttct | 1260 |
| acagctacgc | atagcttgag | tcgtcttcac | accatgctga | caggcctcag | gaatgcacca | 1320 |
| agtgagaaac | tggaacagat | tctcaggaca | tgttccagag | atccaaccca | ggctattgct | 1380 |
| aacagactga | agaaatgtt | tgaaatatat | tctcagcatt | tccagccaga | cgaggatttc | 1440 |
| agtaattgtg | ctaaagaaat | tgccagcaaa | cattttcgtt | ttgcggagat | gctttactat | 1500 |
| aaagtattag | aatctgttat | tgagcaggaa | caaaaaagac | taggagacat | ggatttatct | 1560 |
| ggtattctgg | aacaagatgc | gttccacaga | tctctcttgg | cctgctgcct | tgaggtcgtc | 1620 |
| acttttctt | ataagcctcc | tgggaatttt | ccatttatta | ctgaaatatt | tgatgtgcct | 1680 |
| cttatcatt | tttataaggt | gatagaagta | ttcattagag | cagaagatgg | cctttgtaga | 1740 |
| gaggtggtaa | acaccttaa | tcagattgaa | gaacagatct | tagatcattt | ggcatggaaa | 1800 |
| ccagagtctc | cactctggga | aaaaattaga | gacaatgaaa | acagagttcc | tacatgtgaa | 1860 |
| gaggtcatgc | cacctcagaa | cctggaaagg | gcagatgaaa | tttgcattgc | tggctcccct | 1920 |
| ttgactccca | aagggtgac | tgaagttcgt | gctgatactg | gaggacttgg | aaggagcata | 1980 |
| acatctccaa | ccacattata | cgataggtac | agctccccac | cagccagcac | taccagaagg | 2040 |
| cggctatttg | ttgagaatga | tagcccctct | gatggaggga | cgcctgggcg | catgccccca | 2100 |

```
cagcccctag tcaatgctgt ccctgtgcag aatgtatctg gggagactgt ttctgtcaca   2160
ccagttcctg gacagacttt ggtcaccatg caaccgcca ctgtcacagc caacaatggg    2220
caaacggtaa ccattcctgt gcaaggtatt gccaatgaaa atggagggat aacattcttc   2280
cctgtccaag tcaatgttgg ggggcaggca caagctgtga caggctccat ccagcccctc   2340
agtgctcagg ccctggctgg aagtctgagc tctcaacagg tgacaggaac aactttgcaa   2400
gtccctggtc aagtggccat tcaacagatt tccccaggtg ccaacagca gaagcaaggc    2460 cagtctgtaa ccagcagtag taatagaccc aggaagacca gctctttatc gcttttcttt   2520
agaaaggtat accatttagc agctgtccgc cttcgggatc tctgtgccaa actagatatt   2580
tcagatgaat tgaggaaaaa atctggacc tgctttgaat tctccataat tcagtgtcct    2640
gaacttatga tggacagaca tctggaccag ttattaatgt gtgccattta tgtgatggca   2700
aaggtcacaa agaagataa gtccttccag aacattatgc gttgttatag gactcagccg    2760
caggcccgga gccaggtgta tagaagtgtt ttgataaaag ggaaaagaaa agaagaaat    2820 tctggcagca gtgatagcag aagccatcag aattctccaa cagaactaaa caaagataga   2880
accagtagag actccagtcc agttatgagg tcaagcagca ccttgccagt tccacagccc   2940
agcagtgctc ctcccacacc tactcgcctc acaggtgcca acagtgacat ggaagaagag   3000
gagaggggag acctcattca gttctacaac aacatctaca tcaaacagat taagacattt   3060
gccatgaagt actcacaggc aaatatggat gctcctccac tctctcccta tccatttgta   3120
agaacaggct cccctcgccg aatacagttg tctcaaaatc atcctgtcta catttcccca   3180
cataaaaatg aaacaatgct ttctcctcga gaaaagattt tctattactt cagcaacagt   3240
ccttcaaaga gactgagaga aattaatagt atgatacgca caggagaaac tcctactaaa   3300
aagagaggaa ttcttttgga agatggaagt gaatcacctg caaaaagaat ttgcccagaa   3360
aatcattctg ccttattacg ccgtctccaa gatgtagcta atgaccgtgg ttcccactga   3420
```

<210> SEQ ID NO 6
<211> LENGTH: 1139
<212> TYPE: PRT
<213> ORGANISM: Homo sapiens

<400> SEQUENCE: 6

```
Met Pro Ser Gly Gly Asp Gln Ser Pro Pro Pro Pro Pro Pro Pro Pro
1               5                   10                  15

Ala Ala Ala Ala Ser Asp Glu Glu Glu Asp Asp Gly Glu Ala Glu
            20                  25                  30

Asp Ala Ala Pro Pro Ala Glu Ser Pro Thr Pro Gln Ile Gln Gln Arg
        35                  40                  45

Phe Asp Glu Leu Cys Ser Arg Leu Asn Met Asp Glu Ala Ala Arg Ala
    50                  55                  60

Glu Ala Trp Asp Ser Tyr Arg Ser Met Ser Glu Ser Tyr Thr Leu Glu
65                  70                  75                  80

Gly Asn Asp Leu His Trp Leu Ala Cys Ala Leu Tyr Val Ala Cys Arg
                85                  90                  95

Lys Ser Val Pro Thr Val Ser Lys Gly Thr Val Glu Gly Asn Tyr Val
                100                 105                 110

Ser Leu Thr Arg Ile Leu Lys Cys Ser Glu Gln Ser Leu Ile Glu Phe
            115                 120                 125

Phe Asn Lys Met Lys Lys Trp Glu Asp Met Ala Asn Leu Pro Pro His
        130                 135                 140
```

-continued

Phe Arg Glu Arg Thr Glu Arg Leu Glu Arg Asn Phe Thr Val Ser Ala
145                 150                 155                 160

Val Ile Phe Lys Lys Tyr Glu Pro Ile Phe Gln Asp Ile Phe Lys Tyr
            165                 170                 175

Pro Gln Glu Gln Pro Arg Gln Gln Arg Gly Arg Lys Gln Arg Arg
        180                 185                 190

Gln Pro Cys Thr Val Ser Glu Ile Phe His Phe Cys Trp Val Leu Phe
            195                 200                 205

Ile Tyr Ala Lys Gly Asn Phe Pro Met Ile Ser Asp Asp Leu Val Asn
        210                 215                 220

Ser Tyr His Leu Leu Leu Cys Ala Leu Asp Leu Val Tyr Gly Asn Ala
225                 230                 235                 240

Leu Gln Cys Ser Asn Arg Lys Glu Leu Val Asn Pro Asn Phe Lys Gly
            245                 250                 255

Leu Ser Glu Asp Phe His Ala Lys Asp Ser Lys Pro Ser Ser Asp Pro
        260                 265                 270

Pro Cys Ile Ile Glu Lys Leu Cys Ser Leu His Asp Gly Leu Val Leu
        275                 280                 285

Glu Ala Lys Gly Ile Lys Glu His Phe Trp Lys Pro Tyr Ile Arg Lys
290                 295                 300

Leu Tyr Glu Lys Lys Leu Leu Lys Gly Lys Glu Glu Asn Leu Thr Gly
305                 310                 315                 320

Phe Leu Glu Pro Gly Asn Phe Gly Glu Ser Phe Lys Ala Ile Asn Lys
            325                 330                 335

Ala Tyr Glu Glu Tyr Val Leu Ser Val Gly Asn Leu Asp Glu Arg Ile
        340                 345                 350

Phe Leu Gly Glu Asp Ala Glu Glu Ile Gly Thr Leu Ser Arg Cys
        355                 360                 365

Leu Asn Ala Gly Ser Gly Thr Glu Thr Ala Glu Arg Val Gln Met Lys
370                 375                 380

Asn Ile Leu Gln Gln His Phe Asp Lys Ser Lys Ala Leu Arg Ile Ser
385                 390                 395                 400

Thr Pro Leu Thr Gly Val Arg Tyr Ile Lys Glu Asn Ser Pro Cys Val
            405                 410                 415

Thr Pro Val Ser Thr Ala Thr His Ser Leu Ser Arg Leu His Thr Met
            420                 425                 430

Leu Thr Gly Leu Arg Asn Ala Pro Ser Glu Lys Leu Glu Gln Ile Leu
        435                 440                 445

Arg Thr Cys Ser Arg Asp Pro Thr Gln Ala Ile Ala Asn Arg Leu Lys
        450                 455                 460

Glu Met Phe Glu Ile Tyr Ser Gln His Phe Gln Pro Asp Glu Asp Phe
465                 470                 475                 480

Ser Asn Cys Ala Lys Glu Ile Ala Ser Lys His Phe Arg Phe Ala Glu
            485                 490                 495

Met Leu Tyr Tyr Lys Val Leu Glu Ser Val Ile Glu Gln Glu Gln Lys
        500                 505                 510

Arg Leu Gly Asp Met Asp Leu Ser Gly Ile Leu Glu Gln Asp Ala Phe
        515                 520                 525

His Arg Ser Leu Leu Ala Cys Cys Leu Glu Val Val Thr Phe Ser Tyr
        530                 535                 540

Lys Pro Pro Gly Asn Phe Pro Phe Ile Thr Glu Ile Phe Asp Val Pro
545                 550                 555                 560

```
Leu Tyr His Phe Tyr Lys Val Ile Glu Val Phe Ile Arg Ala Glu Asp
            565                 570                 575
Gly Leu Cys Arg Glu Val Val Lys His Leu Asn Gln Ile Glu Glu Gln
        580                 585                 590
Ile Leu Asp His Leu Ala Trp Lys Pro Glu Ser Pro Leu Trp Glu Lys
    595                 600                 605
Ile Arg Asp Asn Glu Asn Arg Val Pro Thr Cys Glu Glu Val Met Pro
610                 615                 620
Pro Gln Asn Leu Glu Arg Ala Asp Glu Ile Cys Ile Ala Gly Ser Pro
625                 630                 635                 640
Leu Thr Pro Arg Arg Val Thr Glu Val Arg Ala Asp Thr Gly Gly Leu
            645                 650                 655
Gly Arg Ser Ile Thr Ser Pro Thr Thr Leu Tyr Asp Arg Tyr Ser Ser
            660                 665                 670
Pro Pro Ala Ser Thr Thr Arg Arg Leu Phe Val Glu Asn Asp Ser
        675                 680                 685
Pro Ser Asp Gly Gly Thr Pro Gly Arg Met Pro Pro Gln Pro Leu Val
    690                 695                 700
Asn Ala Val Pro Val Gln Asn Val Ser Gly Glu Thr Val Ser Val Thr
705                 710                 715                 720
Pro Val Pro Gly Gln Thr Leu Val Thr Met Ala Thr Ala Thr Val Thr
            725                 730                 735
Ala Asn Asn Gly Gln Thr Val Thr Ile Pro Val Gln Gly Ile Ala Asn
            740                 745                 750
Glu Asn Gly Gly Ile Thr Phe Phe Pro Val Gln Val Asn Val Gly Gly
        755                 760                 765
Gln Ala Gln Ala Val Thr Gly Ser Ile Gln Pro Leu Ser Ala Gln Ala
    770                 775                 780
Leu Ala Gly Ser Leu Ser Ser Gln Gln Val Thr Gly Thr Thr Leu Gln
785                 790                 795                 800
Val Pro Gly Gln Val Ala Ile Gln Gln Ile Ser Pro Gly Gly Gln Gln
            805                 810                 815
Gln Lys Gln Gly Gln Ser Val Thr Ser Ser Ser Asn Arg Pro Arg Lys
            820                 825                 830
Thr Ser Ser Leu Ser Leu Phe Phe Arg Lys Val Tyr His Leu Ala Ala
        835                 840                 845
Val Arg Leu Arg Asp Leu Cys Ala Lys Leu Asp Ile Ser Asp Glu Leu
    850                 855                 860
Arg Lys Lys Ile Trp Thr Cys Phe Glu Phe Ser Ile Ile Gln Cys Pro
865                 870                 875                 880
Glu Leu Met Met Asp Arg His Leu Asp Gln Leu Leu Met Cys Ala Ile
            885                 890                 895
Tyr Val Met Ala Lys Val Thr Lys Glu Asp Lys Ser Phe Gln Asn Ile
            900                 905                 910
Met Arg Cys Tyr Arg Thr Gln Pro Gln Ala Arg Ser Gln Val Tyr Arg
        915                 920                 925
Ser Val Leu Ile Lys Gly Lys Arg Lys Arg Arg Asn Ser Gly Ser Ser
    930                 935                 940
Asp Ser Arg Ser His Gln Asn Ser Pro Thr Glu Leu Asn Lys Asp Arg
945                 950                 955                 960
Thr Ser Arg Asp Ser Ser Pro Val Met Arg Ser Ser Ser Thr Leu Pro
            965                 970                 975
Val Pro Gln Pro Ser Ser Ala Pro Pro Thr Pro Thr Arg Leu Thr Gly
```

Ala Asn Ser Asp Met Glu Glu Glu Arg Gly Asp Leu Ile Gln Phe
    980             985                 990

Tyr Asn Asn Ile Tyr Ile Lys Gln Ile Lys Thr Phe Ala Met Lys
    995             1000                1005

Tyr Ser Gln Ala Asn Met Asp Ala Pro Pro Leu Ser Pro Tyr Pro
    1010            1015                1020

Phe Val Arg Thr Gly Ser Pro Arg Arg Ile Gln Leu Ser Gln Asn
    1025            1030                1035

His Pro Val Tyr Ile Ser Pro His Lys Asn Glu Thr Met Leu Ser
    1040            1045                1050

Pro Arg Glu Lys Ile Phe Tyr Tyr Phe Ser Asn Ser Pro Ser Lys
    1055            1060                1065

Arg Leu Arg Glu Ile Asn Ser Met Ile Arg Thr Gly Glu Thr Pro
    1070            1075                1080

Thr Lys Lys Arg Gly Ile Leu Leu Glu Asp Gly Ser Glu Ser Pro
    1085            1090                1095

Ala Lys Arg Ile Cys Pro Glu Asn His Ser Ala Leu Leu Arg Arg
    1100            1105                1110

Leu Gln Asp Val Ala Asn Asp Arg Gly Ser His
    1115            1120                1125

Leu Gln Asp Val Ala Asn Asp Arg Gly Ser His
    1130            1135

<210> SEQ ID NO 7
<211> LENGTH: 1005
<212> TYPE: DNA
<213> ORGANISM: Homo sapiens

<400> SEQUENCE: 7
atgggacggc cgctgggct gttcccgccc ctatgcccctt ttttgggttt ccggccagag   60
gcatgctggg agcgtcacat gcaaattgag cgtgcaccca gcgttccgcc ctttctacgc  120
tgggccggtt atcgacccgg cccagtgcgc aggcgcggga agttgaact aataaagttt  180
gtacgagttc agtggaggag accgcaagtt gagtggagga ggcggcggtg gggccccgga  240
ccaggtgcct ccatggcagg ctctgaagag ctggggctcc gggaagacac gctgagggtc  300
ctagctgcct tccttaggcg tggtgaggct gccgggtctc ctgttccaac tccacctaga  360
agccctgccc aagaagagcc aacagacttc ctgagccgcc ttcgaagatg tcttccctgc  420
tccctggggc gaggagcagc ccctctgag tccctcggc cttgctctct gcccatccgc  480
ccctgctatg gttagagcc tggcccagct actccagact tctatgcttt ggtgccccag  540
cggctggaac agctggtcca agagcagctg aaatctccgc ccagcccaga attacagggt  600
cccccatcga cagagaagga agccatactg cggaggctgg tggccctgct ggaggaggag  660
gcagaagtca ttaaccagaa gctggcctcg accccgccc tgcgcagcaa gctggtccgc  720
ctgtcctccg actctttcgc ccgcctggtg gagctgttct gtagccggga tgacagctct  780
cgcccaagcc gagcatgccc cgggccccg cctccttccc cggagcccct ggcccgcctg  840
gccctagcca tggagctgag ccggcgcgtg gccgggctgg ggggcacccct ggccggactc  900
agcgtggagc acgtgcacag cttcacgccc tggatccagg cccacggggg ctgggagggc  960
atcctggctg tttcacccgt ggacttgaac ttgccattgg actga            1005

<210> SEQ ID NO 8
<211> LENGTH: 334
<212> TYPE: PRT
<213> ORGANISM: Homo sapiens

<400> SEQUENCE: 8

| | | | | | | | | | | | | | | |
|---|---|---|---|---|---|---|---|---|---|---|---|---|---|---|
|Met|Gly|Arg|Pro|Ala|Gly|Leu|Phe|Pro|Pro|Leu|Cys|Pro|Phe|Leu|Gly
1| | | |5| | | | |10| | | | |15|

Phe Arg Pro Glu Ala Cys Trp Glu Arg His Met Gln Ile Glu Arg Ala
             20                25                30

Pro Ser Val Pro Pro Phe Leu Arg Trp Ala Gly Tyr Arg Pro Gly Pro
             35                40                45

Val Arg Arg Arg Gly Lys Val Glu Leu Ile Lys Phe Val Arg Val Gln
 50                 55                60

Trp Arg Arg Pro Gln Val Glu Trp Arg Arg Arg Trp Gly Pro Gly
65                70                75             80

Pro Gly Ala Ser Met Ala Gly Ser Glu Glu Leu Gly Leu Arg Glu Asp
             85                90                95

Thr Leu Arg Val Leu Ala Ala Phe Leu Arg Arg Gly Glu Ala Ala Gly
            100               105              110

Ser Pro Val Pro Thr Pro Pro Arg Ser Pro Ala Gln Glu Pro Thr
            115               120              125

Asp Phe Leu Ser Arg Leu Arg Arg Cys Leu Pro Cys Ser Leu Gly Arg
   130                135               140

Gly Ala Ala Pro Ser Glu Ser Pro Arg Pro Cys Ser Leu Pro Ile Arg
145                150               155          160

Pro Cys Tyr Gly Leu Glu Pro Gly Pro Ala Thr Pro Asp Phe Tyr Ala
             165               170              175

Leu Val Ala Gln Arg Leu Glu Gln Leu Val Gln Glu Gln Leu Lys Ser
            180               185              190

Pro Pro Ser Pro Glu Leu Gln Gly Pro Pro Ser Thr Glu Lys Glu Ala
            195               200              205

Ile Leu Arg Arg Leu Val Ala Leu Leu Glu Glu Glu Ala Glu Val Ile
   210                215               220

Asn Gln Lys Leu Ala Ser Asp Pro Ala Leu Arg Ser Lys Leu Val Arg
225                230               235          240

Leu Ser Ser Asp Ser Phe Ala Arg Leu Val Glu Leu Phe Cys Ser Arg
            245               250              255

Asp Asp Ser Ser Arg Pro Ser Arg Ala Cys Pro Gly Pro Pro Pro Pro
            260               265              270

Ser Pro Glu Pro Leu Ala Arg Leu Ala Leu Ala Met Glu Leu Ser Arg
            275               280              285

Arg Val Ala Gly Leu Gly Gly Thr Leu Ala Gly Leu Ser Val Glu His
   290                295               300

Val His Ser Phe Thr Pro Trp Ile Gln Ala His Gly Gly Trp Glu Gly
305                310               315          320

Ile Leu Ala Val Ser Pro Val Asp Leu Asn Leu Pro Leu Asp
            325               330

<210> SEQ ID NO 9
<211> LENGTH: 1002
<212> TYPE: DNA
<213> ORGANISM: Homo sapiens

<400> SEQUENCE: 9
atgggacggc cgctgggct gttcccgccc ctatgccctt ttttgggttt ccggccagag    60
gcatgctggg agcgtcacat gcaaattgag cgtgcaccca gcgttccgcc ctttctacgc   120
tgggccggtt atcgacccgg cccagtgcgc aggcgcggga aagttgaact aataaagttt   180

```
gtacgagttc agtggaggag accgcaagtt gagtggagga ggcggcggtg gggccccgga    240
ccaggtgcct ccatggcagg ctctgaagag ctggggctcc gggaagacac gctgagggtc    300
ctagctgcct tccttaggcg tggtgaggct gccgggtctc ctgttccaac tccacctagc    360
cctgcccaag aagagccaac agacttcctg agccgccttc gaagatgtct tccctgctcc    420
ctggggcgag gagcagcccc ctctgagtcc cctcggcctt gctctctgcc catccgcccc    480
tgctatggtt tagagcctgg cccagctact ccagacttct atgctttggt ggcccagcgg    540
ctggaacagc tggtccaaga gcagctgaaa tctccgccca gcccagaatt acagggtccc    600
ccatcgacag agaaggaagc catactgcgg aggctggtgg ccctgctgga ggaggaggca    660
gaagtcatta accagaagct ggcctcggac cccgccctgc gcagcaagct ggtccgcctg    720
tcctccgact ctttcgcccg cctggtggag ctgttctgta gccgggatga cagctctcgc    780
ccaagccgag catgccccgg gcccccgcct ccttccccgg agcccctggc ccgcctggcc    840
ctagccatgg agctgagccg gcgcgtggcc gggctggggg gcaccctggc cggactcagc    900
gtggagcacg tgcacagctt cacgccctgg atccaggccc acgggggctg ggagggcatc    960
ctggctgttt cacccgtgga cttgaacttg ccattggact ga                      1002

<210> SEQ ID NO 10
<211> LENGTH: 333
<212> TYPE: PRT
<213> ORGANISM: Homo sapiens

<400> SEQUENCE: 10

Met Gly Arg Pro Ala Gly Leu Phe Pro Pro Leu Cys Pro Phe Leu Gly
1               5                   10                  15

Phe Arg Pro Glu Ala Cys Trp Glu Arg His Met Gln Ile Glu Arg Ala
            20                  25                  30

Pro Ser Val Pro Pro Phe Leu Arg Trp Ala Gly Tyr Arg Pro Gly Pro
        35                  40                  45

Val Arg Arg Arg Gly Lys Val Glu Leu Ile Lys Phe Val Arg Val Gln
    50                  55                  60

Trp Arg Arg Pro Gln Val Glu Trp Arg Arg Arg Arg Trp Gly Pro Gly
65                  70                  75                  80

Pro Gly Ala Ser Met Ala Gly Ser Glu Glu Leu Gly Leu Arg Glu Asp
                85                  90                  95

Thr Leu Arg Val Leu Ala Ala Phe Leu Arg Arg Gly Glu Ala Ala Gly
            100                 105                 110

Ser Pro Val Pro Thr Pro Pro Ser Pro Ala Gln Glu Glu Pro Thr Asp
        115                 120                 125

Phe Leu Ser Arg Leu Arg Arg Cys Leu Pro Cys Ser Leu Gly Arg Gly
    130                 135                 140

Ala Ala Pro Ser Glu Ser Pro Arg Pro Cys Ser Leu Pro Ile Arg Pro
145                 150                 155                 160

Cys Tyr Gly Leu Glu Pro Gly Pro Ala Thr Pro Asp Phe Tyr Ala Leu
                165                 170                 175

Val Ala Gln Arg Leu Glu Gln Leu Val Gln Glu Gln Leu Lys Ser Pro
            180                 185                 190

Pro Ser Pro Glu Leu Gln Gly Pro Pro Ser Thr Glu Lys Glu Ala Ile
        195                 200                 205

Leu Arg Arg Leu Val Ala Leu Leu Glu Glu Glu Ala Glu Val Ile Asn
    210                 215                 220
```

```
Gln Lys Leu Ala Ser Asp Pro Ala Leu Arg Ser Lys Leu Val Arg Leu
225                 230                 235                 240

Ser Ser Asp Ser Phe Ala Arg Leu Val Glu Leu Phe Cys Ser Arg Asp
                245                 250                 255

Asp Ser Ser Arg Pro Ser Arg Ala Cys Pro Gly Pro Pro Pro Pro Ser
            260                 265                 270

Pro Glu Pro Leu Ala Arg Leu Ala Leu Ala Met Glu Leu Ser Arg Arg
        275                 280                 285

Val Ala Gly Leu Gly Gly Thr Leu Ala Gly Leu Ser Val Glu His Val
    290                 295                 300

His Ser Phe Thr Pro Trp Ile Gln Ala His Gly Gly Trp Glu Gly Ile
305                 310                 315                 320

Leu Ala Val Ser Pro Val Asp Leu Asn Leu Pro Leu Asp
                325                 330
```

<210> SEQ ID NO 11
<211> LENGTH: 1473
<212> TYPE: DNA
<213> ORGANISM: Homo sapiens

<400> SEQUENCE: 11

| | | |
|---|---|---|
| atgacatcat tttccacctc tgctcagtgt tcaacatctg acagtgcttg caggatctct | 60 |
| cctggacaaa tcaatcaggt acgaccaaaa ctgccgcttt tgaagatttt gcatgcagca | 120 |
| ggtgcgcaag gtgaaatgtt cactgttaaa gaggtcatgc actatttagg tcagtacata | 180 |
| atggtgaagc aactttatga tcagcaggag cagcatatgg tatattgtgg tggagatctt | 240 |
| ttgggagaac tactgggacg tcagagcttc tccgtgaaag acccaagccc tctctatgat | 300 |
| atgctaagaa agaatcttgt cactttagcc actgctacta cagatgctgc tcagactctc | 360 |
| gctctcgcac aggatcacag tatggatatt ccaagtcaag accaactgaa gcaaagtgca | 420 |
| gaggaaagtt ccacttccag aaaaagaact acagaagacg atatcccac actgcctacc | 480 |
| tcagagcata aatgcataca ttctagagaa gatgaagact taattgaaaa tttagcccaa | 540 |
| gatgaaacat ctaggctgga ccttggattt gaggagtggg atgtagctgg cctgccttgg | 600 |
| tggtttttag gaaacttgag aagcaactat acacctagaa gtaatggctc aactgattta | 660 |
| cagacaaatc aggatgtggg tactgccatt gtttcagata ctacagatga cttgtggttt | 720 |
| ttgaatgagt cagtatcaga gcagttaggt gttggaataa aagttgaagc tgctgatact | 780 |
| gaacaaacaa gtgaagaagt agggaaagta agtgacaaaa aggtgattga agtgggaaaa | 840 |
| aatgatgacc tggaggactc taagtcctta agtgatgata ccgatgtaga ggttacctct | 900 |
| gaggatgagt ggcagtgtac tgaatgcaag aaatttaact ctccaagcaa gaggtactgt | 960 |
| tttcgttgtt gggccttgag gaaggattgg tattcagatt gttcaaagtt aacccattct | 1020 |
| ctctccacgt ctgatatcac tgccatacct gaaaaggaaa atgaaggaaa tgatgtccct | 1080 |
| gattgtcgaa gaaccatttc ggctcctgtc gttagaccta agatgcgta tataaagaaa | 1140 |
| gaaaactcca acttttttga tccctgcaac tcagtggaat tcttggattt ggctcacagt | 1200 |
| tctgaaagcc aagagaccat ctcaagcatg ggagaacagt tagataacct ttctgaacag | 1260 |
| agaacagata cagaaaacat ggaggattgc cagaatctct tgaagccatg tagcttatgt | 1320 |
| gagaaaagac cacgagacgg gaacattatt catggaagga cgggccatct tgtcacttgt | 1380 |
| tttcactgtg ccagaagact aaagaaggct ggggcttcat gccctatttg caagaaagag | 1440 |
| attcagctgg ttattaaggt ttttatagca taa | 1473 |

<210> SEQ ID NO 12
<211> LENGTH: 490
<212> TYPE: PRT
<213> ORGANISM: Homo sapiens

<400> SEQUENCE: 12

| Met | Thr | Ser | Phe | Ser | Thr | Ser | Ala | Gln | Cys | Ser | Thr | Ser | Asp | Ser | Ala |
|---|---|---|---|---|---|---|---|---|---|---|---|---|---|---|---|
| 1 | | | | 5 | | | | | 10 | | | | | 15 | |

| Cys | Arg | Ile | Ser | Pro | Gly | Gln | Ile | Asn | Gln | Val | Arg | Pro | Lys | Leu | Pro |
| | | | 20 | | | | | 25 | | | | | 30 | | |

| Leu | Leu | Lys | Ile | Leu | His | Ala | Ala | Gly | Ala | Gln | Gly | Glu | Met | Phe | Thr |
| | | 35 | | | | | 40 | | | | | 45 | | | |

| Val | Lys | Glu | Val | Met | His | Tyr | Leu | Gly | Gln | Tyr | Ile | Met | Val | Lys | Gln |
| | 50 | | | | | 55 | | | | | 60 | | | | |

| Leu | Tyr | Asp | Gln | Gln | Glu | Gln | His | Met | Val | Tyr | Cys | Gly | Gly | Asp | Leu |
| 65 | | | | | 70 | | | | | 75 | | | | | 80 |

| Leu | Gly | Glu | Leu | Leu | Gly | Arg | Gln | Ser | Phe | Ser | Val | Lys | Asp | Pro | Ser |
| | | | | 85 | | | | | 90 | | | | | 95 | |

| Pro | Leu | Tyr | Asp | Met | Leu | Arg | Lys | Asn | Leu | Val | Thr | Leu | Ala | Thr | Ala |
| | | | 100 | | | | | 105 | | | | | 110 | | |

| Thr | Thr | Asp | Ala | Ala | Gln | Thr | Leu | Ala | Leu | Ala | Gln | Asp | His | Ser | Met |
| | | | 115 | | | | | 120 | | | | | 125 | | |

| Asp | Ile | Pro | Ser | Gln | Asp | Gln | Leu | Lys | Gln | Ser | Ala | Glu | Glu | Ser | Ser |
| | 130 | | | | | 135 | | | | | 140 | | | | |

| Thr | Ser | Arg | Lys | Arg | Thr | Thr | Glu | Asp | Ile | Pro | Thr | Leu | Pro | Thr |
| 145 | | | | | 150 | | | | | 155 | | | | | 160 |

| Ser | Glu | His | Lys | Cys | Ile | His | Ser | Arg | Glu | Asp | Glu | Asp | Leu | Ile | Glu |
| | | | | 165 | | | | | 170 | | | | | 175 | |

| Asn | Leu | Ala | Gln | Asp | Glu | Thr | Ser | Arg | Leu | Asp | Leu | Gly | Phe | Glu | Glu |
| | | | 180 | | | | | 185 | | | | | 190 | | |

| Trp | Asp | Val | Ala | Gly | Leu | Pro | Trp | Trp | Phe | Leu | Gly | Asn | Leu | Arg | Ser |
| | | 195 | | | | | 200 | | | | | 205 | | | |

| Asn | Tyr | Thr | Pro | Arg | Ser | Asn | Gly | Ser | Thr | Asp | Leu | Gln | Thr | Asn | Gln |
| | 210 | | | | | 215 | | | | | 220 | | | | |

| Asp | Val | Gly | Thr | Ala | Ile | Val | Ser | Asp | Thr | Thr | Asp | Asp | Leu | Trp | Phe |
| 225 | | | | | 230 | | | | | 235 | | | | | 240 |

| Leu | Asn | Glu | Ser | Val | Ser | Glu | Gln | Leu | Gly | Val | Gly | Ile | Lys | Val | Glu |
| | | | | 245 | | | | | 250 | | | | | 255 | |

| Ala | Ala | Asp | Thr | Glu | Gln | Thr | Ser | Glu | Glu | Val | Gly | Lys | Val | Ser | Asp |
| | | | 260 | | | | | 265 | | | | | 270 | | |

| Lys | Lys | Val | Ile | Glu | Val | Gly | Lys | Asn | Asp | Asp | Leu | Glu | Asp | Ser | Lys |
| | | 275 | | | | | 280 | | | | | 285 | | | |

| Ser | Leu | Ser | Asp | Asp | Thr | Asp | Val | Glu | Val | Thr | Ser | Glu | Asp | Glu | Trp |
| | 290 | | | | | 295 | | | | | 300 | | | | |

| Gln | Cys | Thr | Glu | Cys | Lys | Lys | Phe | Asn | Ser | Pro | Ser | Lys | Arg | Tyr | Cys |
| 305 | | | | | 310 | | | | | 315 | | | | | 320 |

| Phe | Arg | Cys | Trp | Ala | Leu | Arg | Lys | Asp | Trp | Tyr | Ser | Asp | Cys | Ser | Lys |
| | | | | 325 | | | | | 330 | | | | | 335 | |

| Leu | Thr | His | Ser | Leu | Ser | Thr | Ser | Asp | Ile | Thr | Ala | Ile | Pro | Glu | Lys |
| | | | 340 | | | | | 345 | | | | | 350 | | |

| Glu | Asn | Glu | Gly | Asn | Asp | Val | Pro | Asp | Cys | Arg | Arg | Thr | Ile | Ser | Ala |
| | | 355 | | | | | 360 | | | | | 365 | | | |

| Pro | Val | Val | Arg | Pro | Lys | Asp | Ala | Tyr | Ile | Lys | Lys | Glu | Asn | Ser | Lys |
| | 370 | | | | | 375 | | | | | 380 | | | | |

Leu Phe Asp Pro Cys Asn Ser Val Glu Phe Leu Asp Leu Ala His Ser
385                 390                 395                 400

Ser Glu Ser Gln Glu Thr Ile Ser Ser Met Gly Glu Gln Leu Asp Asn
            405                 410                 415

Leu Ser Glu Gln Arg Thr Asp Thr Glu Asn Met Glu Asp Cys Gln Asn
        420                 425                 430

Leu Leu Lys Pro Cys Ser Leu Cys Glu Lys Arg Pro Arg Asp Gly Asn
    435                 440                 445

Ile Ile His Gly Arg Thr Gly His Leu Val Thr Cys Phe His Cys Ala
450                 455                 460

Arg Arg Leu Lys Lys Ala Gly Ala Ser Cys Pro Ile Cys Lys Lys Glu
465                 470                 475                 480

Ile Gln Leu Val Ile Lys Val Phe Ile Ala
                485                 490

<210> SEQ ID NO 13
<211> LENGTH: 1323
<212> TYPE: DNA
<213> ORGANISM: Homo sapiens

<400> SEQUENCE: 13
atgacatcat tttccacctc tgctcagtgt tcaacatctg acagtgcttg caggatctct      60
cctggacaaa tcaatcaggt acgaccaaaa ctgccgcttt tgaagatttt gcatgcagca     120
ggtgcgcaag gtgaaatgtt cactgttaaa gaggtcatgc actatttagg tcagtacata     180
atggtgaagc aactttatga tcagcaggag cagcatatgg tatattgtgg tggagatctt     240
ttgggagaac tactgggacg tcagagcttc tccgtgaaag acccaagccc tctctatgat     300
atgctaagaa agaatcttgt cactttagcc actgctacta cagatgctgc tcagactctc     360
gctctcgcac aggatcacag tatggatatt ccaagtcaag accaactgaa gcaaagtgca     420
gaggaaagtt ccacttccag aaaaagaact acagaagacg atatccccac actgcctacc     480
tcagagcata aatgcataca ttctagagaa gatgaagact taattgaaaa tttagcccaa     540
gatgaaacat ctaggctgga ccttggattt gaggagtggg atgtagctgg cctgccttgg     600
tggtttttag gaaacttgag aagcaactat acacctagaa gtaatggctc aactgattta     660
cagacaaatc aggtgattga agtgggaaaa atgatgacc tggaggactc taagtcctta      720
agtgatgata ccgatgtaga ggttacctct gaggatgagt ggcagtgtac tgaatgcaag     780
aaatttaact ctccaagcaa gaggtactgt tttcgttgtt gggccttgag aaggattgg      840
tattcagatt gttcaaagtt aacccattct ctctccacgt ctgatatcac tgccatacct     900
gaaaaggaaa atgaaggaaa tgatgtccct gattgtcgaa gaaccatttc ggctcctgtc     960
gttagaccta agatgcgta tataaagaaa gaaaactcca acttttttga tccctgcaac    1020
tcagtggaat tcttggattt ggctcacagt tctgaaagcc aagagaccat ctcaagcatg    1080
ggagaacagt tagataacct ttctgaacag agaacagata cagaaaacat ggaggattgc    1140
cagaatctct tgaagccatg tagcttatgt gagaaaagac cacgagacgg aaacattatt    1200
catggaagga cgggccatct tgtcacttgt tttcactgtg ccagaagact aaagaaggct    1260
ggggcttcat gccctatttg caagaaagag attcagctgg ttattaaggt ttttatagca    1320
taa                                                                 1323

<210> SEQ ID NO 14
<211> LENGTH: 440

<212> TYPE: PRT
<213> ORGANISM: Homo sapiens

<400> SEQUENCE: 14

```
Met Thr Ser Phe Ser Thr Ser Ala Gln Cys Ser Thr Ser Asp Ser Ala
1               5                   10                  15

Cys Arg Ile Ser Pro Gly Gln Ile Asn Gln Val Arg Pro Lys Leu Pro
            20                  25                  30

Leu Leu Lys Ile Leu His Ala Ala Gly Ala Gln Gly Glu Met Phe Thr
        35                  40                  45

Val Lys Glu Val Met His Tyr Leu Gly Gln Tyr Ile Met Val Lys Gln
50                  55                  60

Leu Tyr Asp Gln Gln Glu Gln His Met Val Tyr Cys Gly Gly Asp Leu
65                  70                  75                  80

Leu Gly Glu Leu Leu Gly Arg Gln Ser Phe Ser Val Lys Asp Pro Ser
                85                  90                  95

Pro Leu Tyr Asp Met Leu Arg Lys Asn Leu Val Thr Leu Ala Thr Ala
            100                 105                 110

Thr Thr Asp Ala Ala Gln Thr Leu Ala Leu Ala Gln Asp His Ser Met
        115                 120                 125

Asp Ile Pro Ser Gln Asp Gln Leu Lys Gln Ser Ala Glu Glu Ser Ser
    130                 135                 140

Thr Ser Arg Lys Arg Thr Thr Glu Asp Ile Pro Thr Leu Pro Thr
145                 150                 155                 160

Ser Glu His Lys Cys Ile His Ser Arg Glu Asp Glu Asp Leu Ile Glu
                165                 170                 175

Asn Leu Ala Gln Asp Glu Thr Ser Arg Leu Asp Leu Gly Phe Glu Glu
            180                 185                 190

Trp Asp Val Ala Gly Leu Pro Trp Trp Phe Leu Gly Asn Leu Arg Ser
        195                 200                 205

Asn Tyr Thr Pro Arg Ser Asn Gly Ser Thr Asp Leu Gln Thr Asn Gln
210                 215                 220

Val Ile Glu Val Gly Lys Asn Asp Asp Leu Glu Asp Ser Lys Ser Leu
225                 230                 235                 240

Ser Asp Asp Thr Asp Val Glu Val Thr Ser Glu Asp Glu Trp Gln Cys
                245                 250                 255

Thr Glu Cys Lys Lys Phe Asn Ser Pro Ser Lys Arg Tyr Cys Phe Arg
            260                 265                 270

Cys Trp Ala Leu Arg Lys Asp Trp Tyr Ser Asp Cys Ser Lys Leu Thr
        275                 280                 285

His Ser Leu Ser Thr Ser Asp Ile Thr Ala Ile Pro Glu Lys Glu Asn
    290                 295                 300

Glu Gly Asn Asp Val Pro Asp Cys Arg Arg Thr Ile Ser Ala Pro Val
305                 310                 315                 320

Val Arg Pro Lys Asp Ala Tyr Ile Lys Lys Glu Asn Ser Lys Leu Phe
                325                 330                 335

Asp Pro Cys Asn Ser Val Glu Phe Leu Asp Leu Ala His Ser Ser Glu
            340                 345                 350

Ser Gln Glu Thr Ile Ser Ser Met Gly Glu Gln Leu Asp Asn Leu Ser
        355                 360                 365

Glu Gln Arg Thr Asp Thr Glu Asn Met Glu Asp Cys Gln Asn Leu Leu
    370                 375                 380

Lys Pro Cys Ser Leu Cys Glu Lys Arg Pro Arg Asp Gly Asn Ile Ile
385                 390                 395                 400
```

```
His Gly Arg Thr Gly His Leu Val Thr Cys Phe His Cys Ala Arg Arg
            405                 410                 415

Leu Lys Lys Ala Gly Ala Ser Cys Pro Ile Cys Lys Lys Glu Ile Gln
        420                 425                 430

Leu Val Ile Lys Val Phe Ile Ala
        435                 440

<210> SEQ ID NO 15
<211> LENGTH: 495
<212> TYPE: DNA
<213> ORGANISM: Homo sapiens

<400> SEQUENCE: 15
atgacatcat tttccacctc tgctcagtgt tcaacatctg acagtgcttg caggatctct      60
cctggacaaa tcaatcagga aaatgaagga aatgatgtcc ctgattgtcg aagaaccatt     120
tcggctcctg tcgttagacc taaagatgcg tatataaaga aagaaaactc caaactttttt   180 gatccctgca actcagtgga attcttggat ttggctcaca gttctgaaag ccaagagacc     240
atctcaagca tgggagaaca gttagataac ctttctgaac agagaacaga tacagaaaac     300
atggaggatt gccagaatct cttgaagcca tgtagcttat gtgagaaaag accacgagac     360
gggaacatta ttcatggaag gacgggccat cttgtcactt gttttcactg tgccagaaga     420
ctaaagaagg ctggggcttc atgccctatt tgcaagaaag agattcagct ggttattaag     480
gtttttatag cataa                                                       495

<210> SEQ ID NO 16
<211> LENGTH: 164
<212> TYPE: PRT
<213> ORGANISM: Homo sapiens

<400> SEQUENCE: 16

Met Thr Ser Phe Ser Thr Ser Ala Gln Cys Ser Thr Ser Asp Ser Ala
1               5                   10                  15

Cys Arg Ile Ser Pro Gly Gln Ile Asn Gln Glu Asn Glu Gly Asn Asp
            20                  25                  30

Val Pro Asp Cys Arg Arg Thr Ile Ser Ala Pro Val Val Arg Pro Lys
        35                  40                  45

Asp Ala Tyr Ile Lys Lys Glu Asn Ser Lys Leu Phe Asp Pro Cys Asn
    50                  55                  60

Ser Val Glu Phe Leu Asp Leu Ala His Ser Ser Glu Ser Gln Glu Thr
65                  70                  75                  80

Ile Ser Ser Met Gly Glu Gln Leu Asp Asn Leu Ser Glu Gln Arg Thr
                85                  90                  95

Asp Thr Glu Asn Met Glu Asp Cys Gln Asn Leu Leu Lys Pro Cys Ser
            100                 105                 110

Leu Cys Glu Lys Arg Pro Arg Asp Gly Asn Ile Ile His Gly Arg Thr
        115                 120                 125

Gly His Leu Val Thr Cys Phe His Cys Ala Arg Arg Leu Lys Lys Ala
    130                 135                 140

Gly Ala Ser Cys Pro Ile Cys Lys Lys Glu Ile Gln Leu Val Ile Lys
145                 150                 155                 160

Val Phe Ile Ala

<210> SEQ ID NO 17
<211> LENGTH: 2196
```

<212> TYPE: DNA
<213> ORGANISM: Homo sapiens

<400> SEQUENCE: 17

| | | | | | |
|---|---|---|---|---|---|
| atgtctggta | gccgccaggc | cgggtcgggc | tccgctggga | caagccccgg | gtcctcggcg | 60
| gcctcctcgg | tgacttccgc | ctcctcgtct | ttatcctctt | ccccgtcgcc | gccttccgtg | 120
| gcggtttcgg | cggcagcgct | ggtgtccggc | ggggtggccc | aggccgccgg | ctcgggcggc | 180
| ctcgggggcc | cggtgcggcc | tgtgttggtg | gcgcccgccg | tatcgggtag | cggcggcggg | 240
| gcggtgtcca | cgggcctgtc | ccggcacagc | tgcgcggcca | ggcccagcgc | cggcgtagga | 300
| ggcagcagct | ccagcctagg | cagcggcagc | aggaagcgac | ctctcctcgc | cccctctgc | 360
| aacgggctca | tcaactccta | cgaggacaaa | agcaacgact | tcgtatgccc | catctgcttt | 420
| gatatgattg | aagaagcata | catgacaaaa | tgtggccaca | gcttttgcta | caagtgtatt | 480
| catcagagtt | tggaggacaa | taatagatgt | cccaagtgta | actatgttgt | ggacaatatt | 540
| gaccatctgt | atcctaattt | cttggtgaat | gaactcattc | ttaaacagaa | gcaaagattt | 600
| gaggaaaaga | ggttcaaatt | ggaccactca | gtgagtagca | ccaatggcca | caggtggcag | 660
| atatttcaag | attggttggg | aactgaccaa | gataaccttg | atttggccaa | tgtcaatctt | 720
| atgttggagt | tactagtgca | gaagaagaaa | caactggaag | cagaatcaca | tgcagcccaa | 780
| ctacagattc | ttatggaatt | cctcaaggtt | gcaagaagaa | ataagagaga | gcaactggaa | 840
| cagatccaga | aggagctaag | tgttttggaa | gaggatatta | agagagtgga | agaaatgagt | 900
| ggcttatact | ctcctgtcag | tgaggatagc | acagtgcctc | aatttgaagc | tccttctcca | 960
| tcacacagta | gtattattga | ttccacagaa | tacagccaac | ctccaggttt | cagtggcagt | 1020
| tctcagacaa | agaaacagcc | ttggtataat | agcacgttag | catcaagacg | aaaacgactt | 1080
| actgctcatt | ttgaagactt | ggagcagtgt | tacttttcta | caaggatgtc | tcgtatctca | 1140
| gatgacagtc | gaactgcaag | ccagttggat | gaatttcagg | aatgcttgtc | caagtttact | 1200
| cgatataatt | cagtacgacc | tttagccaca | ttgtcatatg | ctagtgatct | ctataatggt | 1260
| tccagtatag | tctctagtat | tgaatttgac | cgggattgtg | actattttgc | gattgctgga | 1320
| gttacaaaga | agattaaagt | ctatgaatat | gacactgtca | tccaggatgc | agtggatatt | 1380
| cattaccctg | agaatgaaat | gacctgcaat | tcgaaaatca | gctgtatcag | ttggagtagt | 1440
| taccataaga | acctgttagc | tagcagtgat | tatgaaggca | ctgttatttt | atgggatgga | 1500
| ttcacaggac | agaggtcaaa | ggtctatcag | gagcatgaga | agaggtgttg | gagtgttgac | 1560
| tttaatttga | tggatcctaa | actcttggct | tcaggttctg | atgatgcaaa | agtgaagctg | 1620
| tggtctacca | atctagacaa | ctcagtggca | agcattgagg | caaaggctaa | tgtgtgctgt | 1680
| gttaaattca | gcccctcttc | cagataccat | ttggctttcg | gctgtgcaga | tcactgtgtc | 1740
| cactactatg | atcttcgtaa | cactaaacag | ccaatcatgg | tattcaaagg | acaccgtaaa | 1800
| gcagtctctt | atgcaaagtt | tgtgagtggt | gaggaaattg | tctctgcctc | aacagacagt | 1860
| cagctaaaac | tgtggaatgt | agggaaacca | tactgcctac | gttccttcaa | gggtcatatc | 1920
| aatgaaaaaa | actttgtagg | cctggcttcc | aatggagatt | atatagcttg | tggaagtgaa | 1980
| aataactctc | tctacctgta | ctataaagga | ctttctaaga | ctttgctaac | ttttaagttt | 2040
| gatacagtca | aaagtgttct | cgacaaagac | cgaaaagaag | atgatacaaa | tgaatttgtt | 2100
| agtgctgtgt | gctggagggc | actaccagat | ggggagtcca | atgtgctgat | tgctgctaac | 2160
| agtcagggta | caattaaggt | gctagaattg | gtatga | | | 2196

<210> SEQ ID NO 18
<211> LENGTH: 731
<212> TYPE: PRT
<213> ORGANISM: Homo sapiens

<400> SEQUENCE: 18

```
Met Ser Gly Ser Arg Gln Ala Gly Ser Gly Ser Ala Gly Thr Ser Pro
1               5                   10                  15

Gly Ser Ser Ala Ala Ser Ser Val Thr Ser Ala Ser Ser Ser Leu Ser
            20                  25                  30

Ser Ser Pro Ser Pro Ser Val Ala Val Ser Ala Ala Ala Leu Val
        35                  40                  45

Ser Gly Gly Val Ala Gln Ala Ala Gly Ser Gly Gly Leu Gly Gly Pro
    50                  55                  60

Val Arg Pro Val Leu Val Ala Pro Ala Val Ser Gly Ser Gly Gly Gly
65                  70                  75                  80

Ala Val Ser Thr Gly Leu Ser Arg His Ser Cys Ala Ala Arg Pro Ser
                85                  90                  95

Ala Gly Val Gly Gly Ser Ser Ser Leu Gly Ser Gly Ser Arg Lys
            100                 105                 110

Arg Pro Leu Leu Ala Pro Leu Cys Asn Gly Leu Ile Asn Ser Tyr Glu
            115                 120                 125

Asp Lys Ser Asn Asp Phe Val Cys Pro Ile Cys Phe Asp Met Ile Glu
        130                 135                 140

Glu Ala Tyr Met Thr Lys Cys Gly His Ser Phe Cys Tyr Lys Cys Ile
145                 150                 155                 160

His Gln Ser Leu Glu Asp Asn Asn Arg Cys Pro Lys Cys Asn Tyr Val
                165                 170                 175

Val Asp Asn Ile Asp His Leu Tyr Pro Asn Phe Leu Val Asn Glu Leu
            180                 185                 190

Ile Leu Lys Gln Lys Gln Arg Phe Glu Glu Lys Arg Phe Lys Leu Asp
        195                 200                 205

His Ser Val Ser Ser Thr Asn Gly His Arg Trp Gln Ile Phe Gln Asp
    210                 215                 220

Trp Leu Gly Thr Asp Gln Asp Asn Leu Asp Leu Ala Asn Val Asn Leu
225                 230                 235                 240

Met Leu Glu Leu Leu Val Gln Lys Lys Gln Leu Glu Ala Glu Ser
                245                 250                 255

His Ala Ala Gln Leu Gln Ile Leu Met Glu Phe Leu Lys Val Ala Arg
            260                 265                 270

Arg Asn Lys Arg Glu Gln Leu Glu Gln Ile Gln Lys Glu Leu Ser Val
        275                 280                 285

Leu Glu Glu Asp Ile Lys Arg Val Glu Glu Met Ser Gly Leu Tyr Ser
    290                 295                 300

Pro Val Ser Glu Asp Ser Thr Val Pro Gln Phe Glu Ala Pro Ser Pro
305                 310                 315                 320

Ser His Ser Ser Ile Ile Asp Ser Thr Glu Tyr Ser Gln Pro Pro Gly
                325                 330                 335

Phe Ser Gly Ser Ser Gln Thr Lys Lys Gln Pro Trp Tyr Asn Ser Thr
            340                 345                 350

Leu Ala Ser Arg Arg Lys Arg Leu Thr Ala His Phe Glu Asp Leu Glu
        355                 360                 365

Gln Cys Tyr Phe Ser Thr Arg Met Ser Arg Ile Ser Asp Asp Ser Arg
    370                 375                 380
```

Thr Ala Ser Gln Leu Asp Glu Phe Gln Glu Cys Leu Ser Lys Phe Thr
385                 390                 395                 400

Arg Tyr Asn Ser Val Arg Pro Leu Ala Thr Leu Ser Tyr Ala Ser Asp
            405                 410                 415

Leu Tyr Asn Gly Ser Ser Ile Val Ser Ser Ile Glu Phe Asp Arg Asp
            420                 425                 430

Cys Asp Tyr Phe Ala Ile Ala Gly Val Thr Lys Lys Ile Lys Val Tyr
            435                 440                 445

Glu Tyr Asp Thr Val Ile Gln Asp Ala Val Asp Ile His Tyr Pro Glu
        450                 455                 460

Asn Glu Met Thr Cys Asn Ser Lys Ile Ser Cys Ile Ser Trp Ser Ser
465                 470                 475                 480

Tyr His Lys Asn Leu Leu Ala Ser Ser Asp Tyr Glu Gly Thr Val Ile
            485                 490                 495

Leu Trp Asp Gly Phe Thr Gly Gln Arg Ser Lys Val Tyr Gln Glu His
            500                 505                 510

Glu Lys Arg Cys Trp Ser Val Asp Phe Asn Leu Met Asp Pro Lys Leu
        515                 520                 525

Leu Ala Ser Gly Ser Asp Asp Ala Lys Val Lys Leu Trp Ser Thr Asn
530                 535                 540

Leu Asp Asn Ser Val Ala Ser Ile Glu Ala Lys Ala Asn Val Cys Cys
545                 550                 555                 560

Val Lys Phe Ser Pro Ser Ser Arg Tyr His Leu Ala Phe Gly Cys Ala
            565                 570                 575

Asp His Cys Val His Tyr Tyr Asp Leu Arg Asn Thr Lys Gln Pro Ile
            580                 585                 590

Met Val Phe Lys Gly His Arg Lys Ala Val Ser Tyr Ala Lys Phe Val
        595                 600                 605

Ser Gly Glu Glu Ile Val Ser Ala Ser Thr Asp Ser Gln Leu Lys Leu
610                 615                 620

Trp Asn Val Gly Lys Pro Tyr Cys Leu Arg Ser Phe Lys Gly His Ile
625                 630                 635                 640

Asn Glu Lys Asn Phe Val Gly Leu Ala Ser Asn Gly Asp Tyr Ile Ala
            645                 650                 655

Cys Gly Ser Glu Asn Asn Ser Leu Tyr Leu Tyr Tyr Lys Gly Leu Ser
            660                 665                 670

Lys Thr Leu Leu Thr Phe Lys Phe Asp Thr Val Lys Ser Val Leu Asp
        675                 680                 685

Lys Asp Arg Lys Glu Asp Thr Asn Glu Phe Val Ser Ala Val Cys
690                 695                 700

Trp Arg Ala Leu Pro Asp Gly Glu Ser Asn Val Leu Ile Ala Ala Asn
705                 710                 715                 720

Ser Gln Gly Thr Ile Lys Val Leu Glu Leu Val
            725                 730

<210> SEQ ID NO 19
<211> LENGTH: 2124
<212> TYPE: DNA
<213> ORGANISM: Homo sapiens

<400> SEQUENCE: 19
atgtctggta gccgccaggc cgggtcgggc tccgctggga caagcccgg gtcctcggcg      60 gcctcctcgg tgacttccgc ctcctcgtct ttatcctctt ccccgtcgcc gccttccgtg     120

| | | | | |
|---|---|---|---|---|
| gcggtttcgg | cggcagcgct | ggtgtccggc | ggggtggccc | aggccgccgg | ctcgggcggc | 180 |
| ctcgggggcc | cggtgcggcc | tgtgttggtg | gcgcccgccg | tatcgggtag | cggcggcggg | 240 |
| gcggtgtcca | cgggcctgtc | ccggcacagc | tgcgcggcca | ggcccagcgc | cggcgtagga | 300 |
| ggcagcagct | ccagcctagg | cagcggcagc | aggaagcgac | ctctcctcgc | cccctctgc | 360 |
| aacgggctca | tcaactccta | cgaggacaaa | agcaacgact | tcgtatgccc | catctgcttt | 420 |
| gatatgattg | aagaagcata | catgacaaaa | tgtggccaca | gcttttgcta | caagtgtatt | 480 |
| catcagagtt | tggaggacaa | taatagatgt | cccaagtgta | actatgttgt | ggacaatatt | 540 |
| gaccatctgt | atcctaattt | cttggtgaat | gaactcattc | ttaaacagaa | gcaaagattt | 600 |
| gaggaaaaga | ggttcaaatt | ggaccactca | aatggccaca | ggtggcagat | atttcaagat | 660 |
| tggttgggaa | ctgaccaaga | taaccttgat | ttggccaatg | tcaatcttat | gttggagtta | 720 |
| ctagtgcaga | agaagaaaca | actggaagca | gaatcacatg | cagcccaact | acagattctt | 780 |
| atggaattcc | tcaaggttgc | aagaagaaat | aagagagagg | aaatgagtgg | cttatactct | 840 |
| cctgtcagtg | aggatagcac | agtgcctcaa | tttgaagctc | cttctccatc | acacagtagt | 900 |
| attattgatt | ccacagaata | cagccaacct | ccaggtttca | gtggcagttc | tcagacaaag | 960 |
| aaacagcctt | ggtataatag | cacgttagca | tcaagacgaa | aacgacttac | tgctcatttt | 1020 |
| gaagacttgg | agcagtgtta | cttttctaca | aggatgtctc | gtatctcaga | tgacagtcga | 1080 |
| actgcaagcc | agttggatga | atttcaggaa | tgcttgtcca | gtttactcg | atataattca | 1140 |
| gtacgacctt | tagccacatt | gtcatatgct | agtgatctct | ataatggttc | cagtatagtc | 1200 |
| tctagtattg | aatttgaccg | ggattgtgac | tattttgcga | ttgctggagt | tacaaagaag | 1260 |
| attaaagtct | atgaatatga | cactgtcatc | caggatgcag | tggatattca | ttaccctgag | 1320 |
| aatgaaatga | cctgcaattc | gaaaatcagc | tgtatcagtt | ggagtagtta | ccataagaac | 1380 |
| ctgttagcta | gcagtgatta | tgaaggcact | gttatttat | gggatggatt | cacaggacag | 1440 |
| aggtcaaagg | tctatcagga | gcatgagaag | aggtgttgga | gtgttgactt | taatttgatg | 1500 |
| gatcctaaac | tcttggcttc | aggttctgat | gatgcaaaag | tgaagctgtg | gtctaccaat | 1560 |
| ctagacaact | cagtggcaag | cattgaggca | aaggctaatg | tgtgctgtgt | taaattcagc | 1620 |
| ccctcttcca | gataccattt | ggctttcggc | tgtgcagatc | actgtgtcca | ctactatgat | 1680 |
| cttcgtaaca | ctaaacagcc | aatcatggta | ttcaaaggac | accgtaaagc | agtctcttat | 1740 |
| gcaaagtttg | tgagtggtga | ggaaattgtc | tctgcctcaa | cagacagtca | gctaaaactg | 1800 |
| tggaatgtag | ggaaaccata | ctgcctacgt | tccttcaagg | gtcatatcaa | tgaaaaaaac | 1860 |
| tttgtaggcc | tggcttccaa | tggagattat | atagcttgtg | gaagtgaaaa | taactctctc | 1920 |
| tacctgtact | ataaaggact | ttctaagact | ttgctaactt | ttaagtttga | tacagtcaaa | 1980 |
| agtgttctcg | acaaagaccg | aaaagaagat | gatacaaatg | aatttgttag | tgctgtgtgc | 2040 |
| tggagggcac | taccagatgg | ggagtccaat | gtgctgattg | ctgctaacag | tcagggtaca | 2100 |
| attaaggtgc | tagaattggt | atga | | | | 2124 |

<210> SEQ ID NO 20
<211> LENGTH: 707
<212> TYPE: PRT
<213> ORGANISM: Homo sapiens

<400> SEQUENCE: 20

Met Ser Gly Ser Arg Gln Ala Gly Ser Gly Ser Ala Gly Thr Ser Pro
1               5                   10                  15

```
Gly Ser Ser Ala Ala Ser Ser Val Thr Ser Ala Ser Ser Leu Ser
             20                  25                  30

Ser Ser Pro Ser Pro Ser Val Ala Val Ser Ala Ala Leu Val
         35                  40                  45

Ser Gly Gly Val Ala Gln Ala Ala Gly Ser Gly Leu Gly Gly Pro
     50                  55                  60

Val Arg Pro Val Leu Val Ala Pro Ala Val Ser Gly Ser Gly Gly
65                  70                  75                  80

Ala Val Ser Thr Gly Leu Ser Arg His Ser Cys Ala Ala Arg Pro Ser
                 85                  90                  95

Ala Gly Val Gly Gly Ser Ser Ser Leu Gly Ser Gly Ser Arg Lys
            100                 105                 110

Arg Pro Leu Leu Ala Pro Leu Cys Asn Gly Leu Ile Asn Ser Tyr Glu
            115                 120                 125

Asp Lys Ser Asn Asp Phe Val Cys Pro Ile Cys Phe Asp Met Ile Glu
        130                 135                 140

Glu Ala Tyr Met Thr Lys Cys Gly His Ser Phe Cys Tyr Lys Cys Ile
145                 150                 155                 160

His Gln Ser Leu Glu Asp Asn Arg Cys Pro Lys Cys Asn Tyr Val
                165                 170                 175

Val Asp Asn Ile Asp His Leu Tyr Pro Asn Phe Leu Val Asn Glu Leu
            180                 185                 190

Ile Leu Lys Gln Lys Gln Arg Phe Glu Glu Lys Arg Phe Lys Leu Asp
            195                 200                 205

His Ser Asn Gly His Arg Trp Gln Ile Phe Gln Asp Trp Leu Gly Thr
        210                 215                 220

Asp Gln Asp Asn Leu Asp Leu Ala Asn Val Asn Leu Met Leu Glu Leu
225                 230                 235                 240

Leu Val Gln Lys Lys Gln Leu Glu Ala Glu Ser His Ala Ala Gln
                245                 250                 255

Leu Gln Ile Leu Met Glu Phe Leu Lys Val Ala Arg Arg Asn Lys Arg
            260                 265                 270

Glu Glu Met Ser Gly Leu Tyr Ser Pro Val Ser Glu Asp Ser Thr Val
            275                 280                 285

Pro Gln Phe Glu Ala Pro Ser Pro Ser His Ser Ser Ile Ile Asp Ser
        290                 295                 300

Thr Glu Tyr Ser Gln Pro Pro Gly Phe Ser Gly Ser Ser Gln Thr Lys
305                 310                 315                 320

Lys Gln Pro Trp Tyr Asn Ser Thr Leu Ala Ser Arg Arg Lys Arg Leu
                325                 330                 335

Thr Ala His Phe Glu Asp Leu Glu Gln Cys Tyr Phe Ser Thr Arg Met
            340                 345                 350

Ser Arg Ile Ser Asp Asp Ser Arg Thr Ala Ser Gln Leu Asp Glu Phe
        355                 360                 365

Gln Glu Cys Leu Ser Lys Phe Thr Arg Tyr Asn Ser Val Arg Pro Leu
        370                 375                 380

Ala Thr Leu Ser Tyr Ala Ser Asp Leu Tyr Asn Gly Ser Ser Ile Val
385                 390                 395                 400

Ser Ser Ile Glu Phe Asp Arg Asp Cys Asp Tyr Phe Ala Ile Ala Gly
                405                 410                 415

Val Thr Lys Lys Ile Lys Val Tyr Glu Tyr Asp Thr Val Ile Gln Asp
            420                 425                 430

Ala Val Asp Ile His Tyr Pro Glu Asn Glu Met Thr Cys Asn Ser Lys
```

```
                435                 440                 445
Ile Ser Cys Ile Ser Trp Ser Ser Tyr His Lys Asn Leu Leu Ala Ser
450                 455                 460

Ser Asp Tyr Glu Gly Thr Val Ile Leu Trp Asp Gly Phe Thr Gly Gln
465                 470                 475                 480

Arg Ser Lys Val Tyr Gln Glu His Glu Lys Arg Cys Trp Ser Val Asp
                485                 490                 495

Phe Asn Leu Met Asp Pro Lys Leu Leu Ala Ser Gly Ser Asp Asp Ala
                500                 505                 510

Lys Val Lys Leu Trp Ser Thr Asn Leu Asp Asn Ser Val Ala Ser Ile
                515                 520                 525

Glu Ala Lys Ala Asn Val Cys Cys Val Lys Phe Ser Pro Ser Ser Arg
530                 535                 540

Tyr His Leu Ala Phe Gly Cys Ala Asp His Cys Val His Tyr Tyr Asp
545                 550                 555                 560

Leu Arg Asn Thr Lys Gln Pro Ile Met Val Phe Lys Gly His Arg Lys
                565                 570                 575

Ala Val Ser Tyr Ala Lys Phe Val Ser Gly Glu Glu Ile Val Ser Ala
                580                 585                 590

Ser Thr Asp Ser Gln Leu Lys Leu Trp Asn Val Gly Lys Pro Tyr Cys
                595                 600                 605

Leu Arg Ser Phe Lys Gly His Ile Asn Glu Lys Asn Phe Val Gly Leu
610                 615                 620

Ala Ser Asn Gly Asp Tyr Ile Ala Cys Gly Ser Glu Asn Asn Ser Leu
625                 630                 635                 640

Tyr Leu Tyr Tyr Lys Gly Leu Ser Lys Thr Leu Leu Thr Phe Lys Phe
                645                 650                 655

Asp Thr Val Lys Ser Val Leu Asp Lys Asp Arg Lys Glu Asp Asp Thr
                660                 665                 670

Asn Glu Phe Val Ser Ala Val Cys Trp Arg Ala Leu Pro Asp Gly Glu
                675                 680                 685

Ser Asn Val Leu Ile Ala Ala Asn Ser Gln Gly Thr Ile Lys Val Leu
                690                 695                 700

Glu Leu Val
705

<210> SEQ ID NO 21
<211> LENGTH: 10
<212> TYPE: PRT
<213> ORGANISM: Unknown
<220> FEATURE:
<223> OTHER INFORMATION: Description of Unknown: Transcription
      start site motif peptide

<400> SEQUENCE: 21

Asn Gly Arg Cys Trp Thr Gly Tyr Cys Tyr
1               5                   10

<210> SEQ ID NO 22
<211> LENGTH: 10
<212> TYPE: PRT
<213> ORGANISM: Unknown
<220> FEATURE:
<223> OTHER INFORMATION: Description of Unknown: Transcription
      start site motif peptide

<400> SEQUENCE: 22

Arg Gly Arg Cys Ala Trp Gly Asn Cys Tyr
```

```
<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atctgttcac ttgtgccctg act                                            23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cccttaaccc ctcctcccag aga                                            23

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cctgcttgcc acaggtctcc ccaa                                           24

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26 cccagggtc agaggcaagc aga                                             23

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctccagaaa ggacaagggt ggttggg                                        27

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcatcactgc cccctgatgg caaatg                                         26
```

```
<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gacaaagcaa atggaagtcc tg                                              22

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gctgtcagtg gggaacaaga                                                 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcagctacgg tttccgtctg                                                 20

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctcaagactg gcgctaaaag tt                                              22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctggattggc agccagactg                                                 20
```